(12) United States Patent
Cowan et al.

(10) Patent No.: US 11,998,718 B2
(45) Date of Patent: Jun. 4, 2024

(54) SYSTEM AND METHOD FOR SYRINGE PLUNGER ENGAGEMENT WITH AN INJECTOR

(71) Applicant: BAYER HEALTHCARE LLC, Whippany, NJ (US)

(72) Inventors: Kevin Cowan, Allison Park, PA (US); James Dedig, Pittsburgh, PA (US); Shahab Taheri, Kleinmachnow (DE); Abhinav Srivastava, Pittsburgh, PA (US); Barry Tucker, Verona, PA (US); Michael Swantner, Saxonburg, PA (US); Christopher Capone, Pittsburgh, PA (US); Jaroslow Wlodarczyk, Lower Burrell, PA (US); Andrew Osan, Pittsburgh, PA (US)

(73) Assignee: BAYER HEALTHCARE LLC, Whippany, NJ (US)

( * ) Notice: Subject to any disclaimer, the term of this patent is extended or adjusted under 35 U.S.C. 154(b) by 0 days.

(21) Appl. No.: 17/999,592

(22) PCT Filed: Jun. 16, 2021

(86) PCT No.: PCT/US2021/037574
§ 371 (c)(1),
(2) Date: Nov. 22, 2022

(87) PCT Pub. No.: WO2021/257667
PCT Pub. Date: Dec. 23, 2021

(65) Prior Publication Data
US 2023/0285666 A1 Sep. 14, 2023

Related U.S. Application Data

(60) Provisional application No. 62/705,265, filed on Jun. 18, 2020.

(51) Int. Cl.
*A61M 5/145* (2006.01)
*A61M 5/315* (2006.01)
*A61M 5/36* (2006.01)

(52) U.S. Cl.
CPC .... *A61M 5/14546* (2013.01); *A61M 5/31515* (2013.01); *A61M 5/365* (2013.01); *A61M 2005/14553* (2013.01)

(58) Field of Classification Search
CPC .... A61M 2005/14553; A61M 5/14546; A61M 5/31515; A61M 5/365
See application file for complete search history.

(56) References Cited

U.S. PATENT DOCUMENTS

| 1,265,537 A | 5/1918 | Shull |
| 1,687,323 A | 10/1928 | Cook |

(Continued)

FOREIGN PATENT DOCUMENTS

| AU | 317487 | 1/2008 |
| CN | 1876191 A | 12/2006 |

(Continued)

OTHER PUBLICATIONS

"International Preliminary Report on Patentability from PCT Application No. PCT/US2021/037574", dated Dec. 29, 2022.

(Continued)

*Primary Examiner* — Brandy S Lee
(74) *Attorney, Agent, or Firm* — Joseph L. Kent; James R. Stevenson; David Schramm

(57) ABSTRACT

A plunger for use with a syringe includes a plunger body defining a central longitudinal axis and having a proximal end, a distal end, and a circumferential sidewall connecting the proximal end and the distal end. The plunger further includes at least one retaining member associated with and extending proximally from the plunger body. The at least (Continued)

one retaining member has a first end connected to the plunger body, a second end proximal to the first end and radially and resiliently deflectable relative to the first end, and at least one catch on the second end. A fluid injector system includes a piston having a plunger engagement mechanism configured for interacting with the at least one retaining element of the plunger to releasably engage the plunger for reciprocally driving the plunger within a barrel of the syringe.

13 Claims, 55 Drawing Sheets

(56) References Cited

U.S. PATENT DOCUMENTS

| | | |
|---|---|---|
| 1,950,137 A | 3/1934 | Dowe |
| 1,988,480 A | 1/1935 | Campkin |
| 2,392,196 A | 1/1946 | Smith |
| 2,419,401 A | 4/1947 | Hinds |
| 2,702,547 A | 2/1955 | Glass |
| 2,842,126 A | 7/1958 | Brown |
| 3,051,173 A | 8/1962 | Johnson et al. |
| D203,730 S | 2/1966 | Porat |
| 3,270,483 A | 9/1966 | Smoyer et al. |
| 3,348,545 A | 10/1967 | Sarnoff et al. |
| 3,468,471 A | 9/1969 | Linder |
| 3,597,973 A | 8/1971 | Ryder |
| 3,604,417 A | 9/1971 | Stolzenberg et al. |
| 3,623,474 A | 11/1971 | Heilman et al. |
| 3,645,262 A | 2/1972 | Harrigan |
| 3,701,345 A | 10/1972 | Heilman et al. |
| 3,705,582 A | 12/1972 | Stumpf et al. |
| 3,719,306 A | 3/1973 | Holtzman |
| 3,720,211 A | 3/1973 | Kyrias |
| 3,738,539 A | 6/1973 | Beich |
| 3,752,145 A | 8/1973 | Runnells et al. |
| 3,796,218 A | 3/1974 | Burke et al. |
| 3,809,082 A | 5/1974 | Hurschman |
| 3,812,843 A | 5/1974 | Wootten et al. |
| 3,847,336 A | 11/1974 | Morris et al. |
| 3,902,491 A | 9/1975 | Lajus |
| 3,964,139 A | 6/1976 | Kleinmann et al. |
| 3,987,940 A | 10/1976 | Tischlinger |
| 3,998,224 A | 12/1976 | Chiquiar-Arias |
| 4,006,736 A | 2/1977 | Kranys et al. |
| 4,030,498 A | 6/1977 | Tompkins |
| 4,080,967 A | 3/1978 | O"Leary |
| 4,144,885 A | 3/1979 | Stait |
| 4,148,316 A | 4/1979 | Xanthopoulos |
| 4,155,490 A | 5/1979 | Glenn |
| 4,159,713 A | 7/1979 | Prais |
| 4,180,006 A | 12/1979 | Ross |
| 4,180,069 A | 12/1979 | Walters |
| 4,226,236 A | 10/1980 | Genese |
| 4,252,118 A | 2/1981 | Richard et al. |
| 4,278,086 A | 7/1981 | Hodgins et al. |
| 4,303,070 A | 12/1981 | Ichikawa et al. |
| 4,345,483 A | 8/1982 | Paletta et al. |
| 4,345,595 A | 8/1982 | Whitney et al. |
| 4,351,332 A | 9/1982 | Whitney et al. |
| 4,356,822 A | 11/1982 | Winstead-Hall |
| 4,384,581 A | 5/1983 | Conway |
| 4,424,720 A | 1/1984 | Bucchianeri |
| 4,452,251 A | 6/1984 | Heilman |
| 4,453,934 A | 6/1984 | Gahwiler et al. |
| 4,464,265 A | 8/1984 | Joyner |
| 4,465,472 A | 8/1984 | Urbaniak |
| 4,465,473 A | 8/1984 | Ruegg |
| 4,475,666 A | 10/1984 | Bilbrey et al. |
| 4,476,381 A | 10/1984 | Rubin |
| 4,490,256 A | 12/1984 | Nussbaumer et al. |
| 4,493,646 A | 1/1985 | Lacour et al. |
| 4,500,310 A | 2/1985 | Christinger |
| 4,529,401 A | 7/1985 | Leslie et al. |
| 4,562,844 A | 1/1986 | Carpenter et al. |
| 4,568,335 A | 2/1986 | Updike et al. |
| 4,573,978 A | 3/1986 | Reilly |
| 4,585,439 A | 4/1986 | Michel |
| 4,604,847 A | 8/1986 | Moulding, Jr. et al. |
| 4,612,010 A | 9/1986 | Hamacher et al. |
| 4,617,016 A | 10/1986 | Blomberg |
| 4,628,969 A | 12/1986 | Jurgens, Jr. et al. |
| 4,636,198 A | 1/1987 | Stade |
| 4,648,872 A | 3/1987 | Kamen |
| 4,650,475 A | 3/1987 | Smith et al. |
| 4,652,260 A | 3/1987 | Fenton, Jr. et al. |
| 4,664,128 A | 5/1987 | Lee |
| 4,676,776 A | 6/1987 | Howson |
| 4,677,980 A | 7/1987 | Reilly et al. |
| 4,677,981 A | 7/1987 | Coursant |
| 4,681,566 A | 7/1987 | Fenton, Jr. et al. |
| 4,685,903 A | 8/1987 | Cable et al. |
| 4,695,271 A | 9/1987 | Goethel |
| 4,705,509 A | 11/1987 | Stade |
| 4,718,463 A | 1/1988 | Jurgens, Jr. et al. |
| 4,722,734 A | 2/1988 | Kolln |
| 4,738,817 A | 4/1988 | Wittwer et al. |
| 4,741,732 A | 5/1988 | Crankshaw et al. |
| 4,741,736 A | 5/1988 | Brown |
| 4,749,109 A | 6/1988 | Kamen |
| 4,755,172 A | 7/1988 | Baldwin |
| 4,767,406 A | 8/1988 | Wadham et al. |
| 4,773,900 A | 9/1988 | Cochran |
| 4,791,290 A | 12/1988 | Noone et al. |
| 4,838,857 A | 6/1989 | Strowe et al. |
| 4,840,616 A | 6/1989 | Banks |
| 4,842,581 A | 6/1989 | Davis |
| RE32,974 E | 7/1989 | Porat et al. |
| 4,852,768 A | 8/1989 | Bartsch |
| 4,853,521 A | 8/1989 | Claeys et al. |
| 4,854,324 A | 8/1989 | Hirschman et al. |
| 4,863,427 A | 9/1989 | Cocchi |
| 4,869,720 A | 9/1989 | Chernack |
| 4,878,896 A | 11/1989 | Garrison et al. |
| 4,908,022 A | 3/1990 | Haber |
| 4,911,695 A | 3/1990 | Lindner |
| 4,923,443 A | 5/1990 | Greenwood et al. |
| 4,929,238 A | 5/1990 | Baum |
| 4,931,043 A | 6/1990 | Ray et al. |
| 4,932,941 A | 6/1990 | Min et al. |
| 4,936,833 A | 6/1990 | Sams |
| 4,943,279 A | 7/1990 | Samiotes et al. |
| 4,945,363 A | 7/1990 | Hoffman |
| 4,946,009 A | 8/1990 | Knutson |
| 4,950,243 A | 8/1990 | Estruch |
| 4,966,601 A | 10/1990 | Draenert |
| 4,969,874 A | 11/1990 | Michel et al. |
| 4,973,309 A | 11/1990 | Sultan |
| 4,978,335 A | 12/1990 | Arthur, III |
| 4,988,337 A | 1/1991 | Ito |
| 4,997,423 A | 3/1991 | Okuda et al. |
| 5,000,735 A | 3/1991 | Whelan |
| 5,007,904 A | 4/1991 | Densmore et al. |
| 5,019,045 A | 5/1991 | Lee |
| 5,024,663 A | 6/1991 | Yum |
| 5,033,650 A | 7/1991 | Colin et al. |
| 5,034,004 A | 7/1991 | Crankshaw |
| 5,047,014 A | 9/1991 | Mosebach et al. |
| 5,059,179 A | 10/1991 | Quatrochi et al. |
| 5,062,832 A | 11/1991 | Seghi |
| 5,066,859 A | 11/1991 | Karkar et al. |
| 5,078,683 A | 1/1992 | Sancoff et al. |
| 5,084,017 A | 1/1992 | Maffetone |
| 5,085,638 A | 2/1992 | Farbstein et al. |
| 5,085,643 A | 2/1992 | Larkin et al. |
| 5,090,962 A | 2/1992 | Landry, Jr. et al. |
| 5,093,079 A | 3/1992 | Bakaitis et al. |
| 5,094,148 A | 3/1992 | Haber et al. |
| 5,104,374 A | 4/1992 | Bishko et al. |
| 5,106,372 A | 4/1992 | Ranford |
| 5,106,379 A | 4/1992 | Leap |
| D327,008 S | 6/1992 | Friedman |

(56) References Cited

U.S. PATENT DOCUMENTS

| | | |
|---|---|---|
| 5,122,118 A | 6/1992 | Haber et al. |
| 5,135,507 A | 8/1992 | Haber et al. |
| 5,147,311 A | 9/1992 | Pickhard |
| 5,153,827 A | 10/1992 | Coutre et al. |
| 5,176,642 A | 1/1993 | Clement |
| 5,181,912 A | 1/1993 | Hammett |
| 5,226,897 A | 7/1993 | Nevens et al. |
| 5,236,416 A | 8/1993 | McDaniel et al. |
| 5,242,408 A | 9/1993 | Jhuboo et al. |
| 5,246,423 A | 9/1993 | Farkas |
| 5,254,086 A | 10/1993 | Palmer et al. |
| 5,254,101 A | 10/1993 | Trombley, III |
| 5,256,154 A | 10/1993 | Liebert et al. |
| 5,256,157 A | 10/1993 | Samiotes et al. |
| 5,269,762 A | 12/1993 | Armbruster et al. |
| 5,275,582 A | 1/1994 | Wimmer |
| 5,279,569 A | 1/1994 | Neer et al. |
| 5,282,792 A | 2/1994 | Imbert |
| 5,282,858 A | 2/1994 | Bisch et al. |
| 5,300,031 A | 4/1994 | Neer et al. |
| 5,308,330 A | 5/1994 | Grimard |
| 5,314,415 A | 5/1994 | Liebert et al. |
| 5,317,506 A | 5/1994 | Coutre et al. |
| 5,324,273 A | 6/1994 | Discko, Jr. |
| 5,336,189 A | 8/1994 | Sealfon |
| 5,338,309 A | 8/1994 | Imbert |
| 5,342,298 A | 8/1994 | Michaels et al. |
| 5,353,691 A | 10/1994 | Haber et al. |
| 5,354,287 A | 10/1994 | Wacks |
| 5,356,375 A | 10/1994 | Higley |
| 5,356,393 A | 10/1994 | Haber et al. |
| 5,373,684 A | 12/1994 | Vacca |
| 5,380,285 A | 1/1995 | Jenson |
| 5,383,858 A | 1/1995 | Reilly et al. |
| 5,389,075 A | 2/1995 | Vladimirsky |
| 5,397,313 A | 3/1995 | Gross |
| 5,411,488 A | 5/1995 | Pagay et al. |
| 5,413,563 A | 5/1995 | Basile et al. |
| 5,425,716 A | 6/1995 | Kawasaki et al. |
| 5,429,602 A | 7/1995 | Hauser |
| 5,429,611 A | 7/1995 | Rait |
| 5,431,627 A | 7/1995 | Pastrone et al. |
| 5,433,712 A | 7/1995 | Stiles et al. |
| 5,439,452 A | 8/1995 | McCarty |
| 5,445,622 A | 8/1995 | Brown |
| 5,451,211 A | 9/1995 | Neer et al. |
| 5,456,670 A | 10/1995 | Neer et al. |
| 5,461,239 A | 10/1995 | Atherton |
| D364,461 S | 11/1995 | Liebert et al. |
| 5,478,314 A | 12/1995 | Malenchek |
| 5,484,413 A | 1/1996 | Gevorgian |
| 5,512,054 A | 4/1996 | Morningstar |
| 5,520,653 A | 5/1996 | Reilly et al. |
| 5,531,698 A | 7/1996 | Olsen |
| 5,531,710 A | 7/1996 | Dang et al. |
| 5,533,981 A | 7/1996 | Mandro et al. |
| 5,535,746 A | 7/1996 | Hoover et al. |
| 5,540,660 A | 7/1996 | Jenson |
| 5,545,140 A | 8/1996 | Conero et al. |
| 5,573,515 A | 11/1996 | Wilson et al. |
| 5,593,386 A | 1/1997 | Helldin |
| 5,624,408 A | 4/1997 | Helldin |
| D379,640 S | 6/1997 | Gilbert |
| 5,658,261 A | 8/1997 | Neer et al. |
| 5,662,612 A | 9/1997 | Niehoff |
| 5,681,285 A | 10/1997 | Ford et al. |
| 5,681,286 A | 10/1997 | Niehoff |
| 5,683,367 A | 11/1997 | Jordan et al. |
| 5,688,252 A | 11/1997 | Matsuda et al. |
| 5,695,477 A | 12/1997 | Sfikas |
| 5,722,951 A | 3/1998 | Marano |
| 5,735,825 A | 4/1998 | Stevens et al. |
| 5,738,655 A | 4/1998 | Vallelunga et al. |
| 5,738,659 A | 4/1998 | Neer et al. |
| 5,741,227 A | 4/1998 | Sealfon |
| 5,741,232 A | 4/1998 | Reilly et al. |
| 5,779,675 A | 7/1998 | Reilly et al. |
| 5,782,803 A | 7/1998 | Jentzen |
| 5,785,682 A | 7/1998 | Grabenkort |
| 5,795,333 A | 8/1998 | Reilly et al. |
| 5,795,337 A | 8/1998 | Grimard |
| 5,806,519 A | 9/1998 | Evans, III et al. |
| 5,807,321 A | 9/1998 | Stoker et al. |
| 5,807,334 A | 9/1998 | Hodosh et al. |
| 5,808,203 A | 9/1998 | Nolan, Jr. et al. |
| 5,827,219 A | 10/1998 | Uber, III et al. |
| 5,827,262 A | 10/1998 | Neftel et al. |
| 5,840,026 A | 11/1998 | Uber, III et al. |
| RE35,979 E | 12/1998 | Reilly et al. |
| 5,843,037 A | 12/1998 | Uber, III |
| D403,762 S | 1/1999 | Gabbard et al. |
| 5,858,239 A | 1/1999 | Kenley et al. |
| 5,865,805 A | 2/1999 | Ziemba |
| 5,873,861 A * | 2/1999 | Hitchins ............ A61M 5/14546 604/152 |
| D407,362 S | 3/1999 | Schardt |
| 5,879,336 A | 3/1999 | Brinon |
| 5,882,343 A | 3/1999 | Wilson et al. |
| 5,899,885 A | 5/1999 | Reilly et al. |
| 5,902,276 A | 5/1999 | Namey, Jr. |
| 5,913,844 A | 6/1999 | Ziemba et al. |
| 5,916,197 A | 6/1999 | Reilly et al. |
| 5,919,167 A | 7/1999 | Mulhauser et al. |
| 5,928,197 A | 7/1999 | Niehoff |
| D412,635 S | 8/1999 | Eiling |
| 5,938,637 A | 8/1999 | Austin et al. |
| 5,938,639 A | 8/1999 | Reilly et al. |
| 5,944,694 A | 8/1999 | Hitchins et al. |
| 5,947,929 A | 9/1999 | Trull |
| 5,947,935 A | 9/1999 | Rhinehart et al. |
| 5,954,697 A | 9/1999 | Srisathapat et al. |
| 5,954,700 A | 9/1999 | Kovelman |
| 5,997,502 A | 12/1999 | Reilly et al. |
| 5,997,511 A | 12/1999 | Curie et al. |
| 6,004,292 A | 12/1999 | Battiato et al. |
| 6,004,300 A | 12/1999 | Butcher et al. |
| 6,017,330 A | 1/2000 | Hitchins et al. |
| 6,019,745 A | 2/2000 | Gray |
| 6,042,565 A | 3/2000 | Hirschman et al. |
| 6,048,334 A | 4/2000 | Hirschman et al. |
| D424,198 S | 5/2000 | Shepherd et al. |
| 6,059,756 A | 5/2000 | Yeh |
| 6,080,136 A | 6/2000 | Trull et al. |
| 6,083,197 A | 7/2000 | Umbaugh |
| 6,083,200 A | 7/2000 | Grimm et al. |
| 6,090,064 A | 7/2000 | Reilly et al. |
| 6,099,502 A | 8/2000 | Duchon et al. |
| 6,129,712 A | 10/2000 | Sudo et al. |
| 6,142,976 A | 11/2000 | Kubo |
| 6,162,200 A | 12/2000 | Sawa et al. |
| 6,190,363 B1 | 2/2001 | Gabbard et al. |
| 6,196,999 B1 | 3/2001 | Goethel et al. |
| 6,221,045 B1 | 4/2001 | Duchon et al. |
| 6,221,051 B1 | 4/2001 | Hjertman et al. |
| 6,224,577 B1 | 5/2001 | Dedola et al. |
| 6,267,749 B1 | 7/2001 | Miklos et al. |
| D447,799 S | 9/2001 | Jun |
| 6,290,678 B1 | 9/2001 | Aydelotte et al. |
| 6,312,410 B1 | 11/2001 | Yamamoto |
| 6,315,758 B1 | 11/2001 | Neer et al. |
| 6,322,535 B1 | 11/2001 | Hitchins et al. |
| RE37,487 E | 12/2001 | Reilly et al. |
| 6,332,877 B1 | 12/2001 | Michels |
| 6,336,913 B1 | 1/2002 | Spohn et al. |
| 6,339,718 B1 | 1/2002 | Zatezalo et al. |
| 6,345,262 B1 | 2/2002 | Madden |
| 6,368,307 B1 | 4/2002 | Ziemba et al. |
| 6,432,089 B1 | 8/2002 | Kakimi et al. |
| 6,447,487 B1 | 9/2002 | Cane' |
| 6,511,459 B1 | 1/2003 | Fago |
| 6,517,516 B1 | 2/2003 | Caizza |
| 6,533,183 B2 | 3/2003 | Aasmul et al. |
| 6,533,758 B1 | 3/2003 | Staats et al. |
| 6,569,127 B1 | 5/2003 | Fago et al. |

(56) References Cited

U.S. PATENT DOCUMENTS

| | | |
|---|---|---|
| 6,582,399 B1 | 6/2003 | Smith et al. |
| 6,585,700 B1 | 7/2003 | Trocki et al. |
| 6,626,862 B1 | 9/2003 | Duchon et al. |
| 6,652,489 B2 | 11/2003 | Trocki et al. |
| 6,659,979 B2 | 12/2003 | Neer et al. |
| 6,669,663 B1 | 12/2003 | Thompson |
| 6,676,635 B2 | 1/2004 | Nemoto |
| 6,726,657 B1 | 4/2004 | Dedig et al. |
| 6,733,477 B2 | 5/2004 | Cowan et al. |
| 6,733,478 B2 | 5/2004 | Reilly et al. |
| 6,743,202 B2 | 6/2004 | Hirschman et al. |
| 6,752,789 B2 | 6/2004 | Duchon et al. |
| 6,764,466 B1 | 7/2004 | Staats et al. |
| 6,808,513 B2 | 10/2004 | Reilly et al. |
| 6,817,990 B2 | 11/2004 | Yap et al. |
| 6,958,053 B1 | 10/2005 | Reilly |
| 7,018,363 B2 | 3/2006 | Cowan et al. |
| 7,025,757 B2 | 4/2006 | Reilly et al. |
| 7,029,459 B2 | 4/2006 | Reilly |
| 7,094,216 B2 | 8/2006 | Trombley, III et al. |
| 7,101,352 B2 | 9/2006 | Dochon et al. |
| 7,240,882 B2 | 7/2007 | Degentesh et al. |
| 7,264,612 B2 | 9/2007 | Nemoto |
| D555,802 S | 11/2007 | Coulling et al. |
| 7,300,417 B1 | 11/2007 | Goethel et al. |
| 7,337,538 B2 | 3/2008 | Moutafis et al. |
| 7,344,520 B2 | 3/2008 | Nemoto |
| 7,393,341 B2 | 7/2008 | Nemoto |
| 7,399,293 B2 | 7/2008 | Oyibo et al. |
| 7,419,478 B1 | 9/2008 | Reilly et al. |
| 7,455,659 B2 | 11/2008 | Nemoto et al. |
| 7,462,166 B2 | 12/2008 | Kowan et al. |
| 7,465,290 B2 | 12/2008 | Reilly |
| 7,497,843 B1 | 3/2009 | Castillo et al. |
| 7,501,092 B2 | 3/2009 | Chen |
| 7,503,906 B2 | 3/2009 | Nemoto |
| 7,540,856 B2 | 6/2009 | Hitchins |
| 7,549,977 B2 | 6/2009 | Schriver et al. |
| 7,553,294 B2 | 6/2009 | Lazzaro et al. |
| 7,556,619 B2 | 7/2009 | Spohn et al. |
| 7,566,326 B2 | 7/2009 | Duchon et al. |
| 7,666,169 B2 | 2/2010 | Cowan et al. |
| 7,682,345 B2 | 3/2010 | Savage |
| 7,691,085 B2 | 4/2010 | Dedig et al. |
| 7,695,457 B2 | 4/2010 | Nemoto |
| 7,753,885 B2 | 7/2010 | Duchon et al. |
| 7,775,990 B2 | 8/2010 | DeHart |
| 7,803,134 B2 | 9/2010 | Sharifi et al. |
| 7,854,726 B2 | 12/2010 | Fago et al. |
| 7,875,005 B2 | 1/2011 | Nemoto |
| D632,389 S | 2/2011 | Maeda et al. |
| D632,784 S | 2/2011 | Maeda et al. |
| D637,492 S | 5/2011 | Baird et al. |
| 7,937,134 B2 | 5/2011 | Uber et al. |
| 7,972,306 B2 | 7/2011 | Shearn |
| 7,998,133 B2 | 8/2011 | Fago et al. |
| 8,012,124 B1 | 9/2011 | Fago et al. |
| 8,012,125 B1 | 9/2011 | Fago et al. |
| 8,038,656 B2 | 10/2011 | Lloyd et al. |
| 8,070,732 B2 | 12/2011 | Rochette |
| 8,105,293 B2 | 1/2012 | Pickhard |
| 8,133,203 B2 | 3/2012 | Hack |
| 8,147,464 B2 | 4/2012 | Spohn et al. |
| 8,172,796 B2 | 5/2012 | Schriver et al. |
| 8,172,814 B2 | 5/2012 | Cane et al. |
| 8,173,995 B2 | 5/2012 | Ramakrishnan et al. |
| 8,177,757 B2 | 5/2012 | Nemoto et al. |
| D665,498 S | 8/2012 | Tamura et al. |
| 8,262,644 B2 | 9/2012 | Fago et al. |
| D668,331 S | 10/2012 | Ren et al. |
| 8,308,689 B2 | 11/2012 | Lewis |
| 8,337,456 B2 | 12/2012 | Schriver et al. |
| 8,353,879 B2 | 1/2013 | Goethel et al. |
| 8,403,909 B2 | 3/2013 | Spohn et al. |
| 8,454,560 B2 | 6/2013 | Strobl |
| D686,322 S | 7/2013 | Maeda et al. |
| 8,475,415 B2 | 7/2013 | Schiller et al. |
| 8,480,631 B2 | 7/2013 | Wotton et al. |
| 8,506,523 B2 | 8/2013 | Miyazaki et al. |
| 8,574,200 B2 | 11/2013 | Hack |
| 8,585,658 B2 | 11/2013 | Forstreuter |
| 8,597,246 B1 | 12/2013 | Fago et al. |
| 8,613,730 B2 | 12/2013 | Hieb et al. |
| 8,628,495 B2 | 1/2014 | Horton et al. |
| 8,721,596 B2 | 5/2014 | Trocki et al. |
| 8,740,854 B2 | 6/2014 | Schiller et al. |
| 8,740,856 B2 | 6/2014 | Quinn et al. |
| 8,740,877 B2 | 6/2014 | Borlaug et al. |
| 8,800,071 B2 | 8/2014 | Sanchez Moreno |
| 8,845,596 B2 | 9/2014 | Berman et al. |
| 8,851,866 B2 | 10/2014 | Moutafis et al. |
| 8,857,674 B2 | 10/2014 | Nighy et al. |
| 8,864,712 B1 | 10/2014 | Fago et al. |
| 8,926,569 B2 | 1/2015 | Bisegna et al. |
| 8,932,255 B1 | 1/2015 | Fago et al. |
| 8,945,051 B2 | 2/2015 | Schriver et al. |
| 9,173,995 B1 | 11/2015 | Tucker et al. |
| 9,174,003 B2 | 11/2015 | Cowan et al. |
| D745,668 S | 12/2015 | Shiraishi et al. |
| 9,199,033 B1 | 12/2015 | Cowan et al. |
| 9,566,381 B2 | 2/2017 | Barron et al. |
| D787,668 S | 5/2017 | Ishida et al. |
| D788,296 S | 5/2017 | Ishida et al. |
| D788,297 S | 5/2017 | Ishida et al. |
| 9,636,452 B2 | 5/2017 | Trocki et al. |
| D788,912 S | 6/2017 | Ishida et al. |
| D792,206 S | 7/2017 | Baiz et al. |
| 9,694,131 B2 | 7/2017 | Cowan et al. |
| D793,220 S | 8/2017 | Baiz et al. |
| D793,854 S | 8/2017 | Baiz et al. |
| 9,844,622 B2 | 12/2017 | Savage |
| 10,022,493 B2 | 7/2018 | Shearer, Jr. et al. |
| D826,397 S | 8/2018 | Green |
| D848,756 S | 5/2019 | Ren |
| 10,286,152 B2 | 5/2019 | Cowan et al. |
| 10,420,902 B2 | 9/2019 | Cowan et al. |
| 10,507,319 B2 | 12/2019 | Haury et al. |
| 10,512,721 B2 | 12/2019 | Swantner et al. |
| 10,532,166 B2 | 1/2020 | Schriver et al. |
| 11,351,306 B2 | 6/2022 | Swantner |
| 2002/0071920 A1 | 6/2002 | Obeshaw |
| 2003/0004468 A1 | 1/2003 | Righi et al. |
| 2003/0009133 A1 | 1/2003 | Ramey |
| 2003/0065287 A1 | 4/2003 | Spohn et al. |
| 2003/0120219 A1 | 6/2003 | Nielsen et al. |
| 2003/0153877 A1 | 8/2003 | Huang et al. |
| 2003/0163089 A1 | 8/2003 | Bynum |
| 2003/0216683 A1 | 11/2003 | Shekalim |
| 2003/0236800 A1 | 12/2003 | Goeltzenleuchter et al. |
| 2004/0006314 A1 | 1/2004 | Campbell et al. |
| 2004/0039368 A1 | 2/2004 | Reilly et al. |
| 2004/0074453 A1 | 4/2004 | Roelle et al. |
| 2004/0116861 A1 | 6/2004 | Trocki et al. |
| 2004/0122370 A1 | 6/2004 | Joyce et al. |
| 2004/0133153 A1 | 7/2004 | Trocki et al. |
| 2004/0133183 A1 | 7/2004 | Trocki et al. |
| 2004/0186437 A1 | 9/2004 | Frenette et al. |
| 2004/0243022 A1 | 12/2004 | Carney et al. |
| 2004/0243067 A1 | 12/2004 | Sibbitt |
| 2005/0063857 A1 | 3/2005 | Alheidt et al. |
| 2005/0080384 A1 | 4/2005 | Green, Jr. |
| 2005/0240149 A1 | 10/2005 | Lu |
| 2006/0084925 A1 | 4/2006 | Ramsahoye |
| 2006/0129104 A1 | 6/2006 | Cowan et al. |
| 2006/0173411 A1 | 8/2006 | Barere |
| 2007/0123830 A1 | 5/2007 | Johannes Fierkens, Sr. et al. |
| 2007/0191785 A1 | 8/2007 | Barere et al. |
| 2007/0203460 A1 | 8/2007 | Nemoto et al. |
| 2008/0086087 A1 | 4/2008 | Spohn et al. |
| 2008/0167615 A1 | 7/2008 | Niehoff |
| 2008/0306443 A1 | 12/2008 | Neer et al. |
| 2009/0124995 A1 | 5/2009 | Bruce |
| 2009/0188311 A1 | 7/2009 | Cadieux et al. |
| 2009/0247957 A1 | 10/2009 | Heutschi |

(56) References Cited

U.S. PATENT DOCUMENTS

| | | | |
|---|---|---|---|
| 2010/0013096 A1 | 1/2010 | Irumata et al. |
| 2010/0016796 A1 | 1/2010 | Derichs |
| 2010/0130961 A1 | 5/2010 | Tucker |
| 2010/0280370 A1 | 11/2010 | Namey, Jr. |
| 2010/0318030 A1 | 12/2010 | Jenkins |
| 2011/0056290 A1 | 3/2011 | Bryant et al. |
| 2011/0106015 A1 | 5/2011 | Liscio et al. |
| 2011/0178500 A1 | 7/2011 | Shang et al. |
| 2011/0208350 A1 | 8/2011 | Eliuk et al. |
| 2011/0224611 A1 | 9/2011 | Lum et al. |
| 2012/0039809 A1 | 2/2012 | Levinson et al. |
| 2012/0104256 A1 | 5/2012 | Rapoport et al. |
| 2012/0127290 A1 | 5/2012 | Tojo et al. |
| 2012/0172817 A1 | 7/2012 | Bruggemann et al. |
| 2012/0184920 A1 | 7/2012 | Okihara et al. |
| 2012/0286187 A1 | 11/2012 | Spolski |
| 2013/0150806 A1 | 6/2013 | Fangrow, Jr. |
| 2013/0150821 A1 | 6/2013 | Bollish et al. |
| 2013/0211325 A1 | 8/2013 | Wang et al. |
| 2013/0310756 A1 | 11/2013 | Whalley et al. |
| 2013/0317427 A1 | 11/2013 | Brereton et al. |
| 2013/0317480 A1 | 11/2013 | Reber et al. |
| 2013/0338605 A1 | 12/2013 | Chen |
| 2014/0027009 A1 | 1/2014 | Riley et al. |
| 2014/0031763 A1 | 1/2014 | Soma et al. |
| 2014/0045668 A1 | 2/2014 | Case et al. |
| 2014/0200483 A1 | 7/2014 | Fojtik |
| 2014/0330216 A1 | 11/2014 | Weaver et al. |
| 2018/0296754 A1 | 10/2018 | Shearer, Jr. et al. |
| 2019/0314573 A1 | 10/2019 | Cowan et al. |
| 2020/0046894 A1 | 2/2020 | Cowan et al. |

FOREIGN PATENT DOCUMENTS

| | | | |
|---|---|---|---|
| CN | 101801442 A | 8/2010 |
| DE | 2919978 A1 | 11/1980 |
| DE | 3227417 A1 | 2/1983 |
| DE | 4017920 A1 | 12/1991 |
| DE | 4319115 A1 | 12/1994 |
| DE | 19601214 A1 | 8/1996 |
| DE | 19633530 A1 | 2/1998 |
| EP | 0111724 A2 | 6/1984 |
| EP | 0160303 A2 | 11/1985 |
| EP | 0164904 A2 | 12/1985 |
| EP | 0308380 A2 | 3/1989 |
| EP | 0319275 A1 | 6/1989 |
| EP | 0320168 A1 | 6/1989 |
| EP | 0323321 A1 | 7/1989 |
| EP | 0346950 A2 | 12/1989 |
| EP | 0364010 A2 | 4/1990 |
| EP | 0384657 A1 | 8/1990 |
| EP | 0482677 A1 | 4/1992 |
| EP | 0523343 A1 | 1/1993 |
| EP | 0523434 A1 | 1/1993 |
| EP | 0567944 A1 | 11/1993 |
| EP | 0567945 A1 | 11/1993 |
| EP | 0584531 A2 | 3/1994 |
| EP | 0736306 A1 | 10/1996 |
| EP | 0749757 A2 | 12/1996 |
| EP | 0900573 A2 | 3/1999 |
| EP | 0919251 A2 | 6/1999 |
| EP | 0951306 A2 | 10/1999 |
| EP | 1002551 A2 | 5/2000 |
| EP | 1166807 A1 | 1/2002 |
| EP | 1932555 A1 | 6/2008 |
| EP | 2327431 A1 | 6/2011 |
| GB | 847914 A | 9/1960 |
| GB | 1380873 A | 1/1975 |
| GB | 2108852 A | 5/1983 |
| JP | S61500415 A | 3/1986 |
| JP | S6327770 A | 2/1988 |
| JP | S6368177 A | 3/1988 |
| JP | 2001029466 A | 2/2001 |
| JP | 4462798 B2 | 5/2010 |
| JP | D1398129 | 10/2010 |
| JP | D1398130 | 10/2010 |
| JP | D1400385 | 11/2010 |
| JP | D1400386 | 11/2010 |
| JP | D1400551 | 11/2010 |
| JP | D1400552 | 11/2010 |
| TW | 358742 B | 5/1999 |
| WO | 8002376 A1 | 11/1980 |
| WO | 8500292 A1 | 1/1985 |
| WO | 8502256 A1 | 5/1985 |
| WO | 8906145 A1 | 7/1989 |
| WO | 8909071 A1 | 10/1989 |
| WO | 8911310 A1 | 11/1989 |
| WO | 9001962 A1 | 3/1990 |
| WO | 9104759 A1 | 4/1991 |
| WO | 9221391 A1 | 12/1992 |
| WO | 9413336 A1 | 6/1994 |
| WO | 9425089 A1 | 11/1994 |
| WO | 9632975 A1 | 10/1996 |
| WO | 9707841 A2 | 3/1997 |
| WO | 9736635 A1 | 10/1997 |
| WO | 9800187 A1 | 1/1998 |
| WO | 9820920 A2 | 5/1998 |
| WO | 9910032 A1 | 3/1999 |
| WO | 9965548 A1 | 12/1999 |
| WO | 0108727 A1 | 2/2001 |
| WO | 0137903 A2 | 5/2001 |
| WO | 0137905 A2 | 5/2001 |
| WO | 0204049 A1 | 1/2002 |
| WO | 02056934 A2 | 7/2002 |
| WO | 02081011 A1 | 10/2002 |
| WO | 03101527 A1 | 12/2003 |
| WO | 2004035289 A1 | 4/2004 |
| WO | 2005053771 A2 | 6/2005 |
| WO | 2007064234 A1 | 6/2007 |
| WO | 2007130061 A1 | 11/2007 |
| WO | 2008011401 A2 | 1/2008 |
| WO | 2008051576 A2 | 5/2008 |
| WO | 2008059448 A2 | 5/2008 |
| WO | 2009025996 A1 | 2/2009 |
| WO | 2009036496 A2 | 3/2009 |
| WO | 2009038955 A1 | 3/2009 |
| WO | 2010139793 A1 | 12/2010 |
| WO | 2011129175 A1 | 10/2011 |
| WO | 2012124028 A1 | 9/2012 |
| WO | 2012155035 A1 | 11/2012 |
| WO | 2014160326 A1 | 10/2014 |
| WO | 2015006430 A1 | 1/2015 |
| WO | 2016045699 A1 | 3/2016 |
| WO | 2016069711 A1 | 5/2016 |
| WO | 2016069714 A1 | 5/2016 |
| WO | 2019168776 A1 | 9/2019 |
| WO | 2021050507 A1 | 3/2021 |
| WO | 2021173743 A1 | 9/2021 |

OTHER PUBLICATIONS

Brochure for "Angiomat 6000" of Liebel-Farsheim, 2111 E. Galbraith Road, Cincinnati, OH 45215, © 1987.
Brochure for "Angiomat CT" of Liebel-Farsheim, 2111 E. Galbraith Road, Cincinnati, OH 45215, © 1988.
Brochure for "Cordis Lymphography Injector," Cordis Corporation, Miami, FL 33137 (1972).
Brochure for "PercuPump 1A" of E-Z-Em, Inc, 717 Main Street, Westbury, NY 11590, © 1990.
Brochure for the "The First and Only True Injection System, "Medrad Mark V System, Control No. 85106-00-BA-02, Nov. 1988.
Comar., "Oral Syringes", Jul. 2015.
Human; Engineering Branch., "Field Study Of Detectability Of Colored Targets At Sea", U.S. Naval Medical Research aboratory, May 26, 1955, vol. XIV, No. 5.
Injektron 82 MRT User Instructions, Version MR2, CEO535, Med-Tron GmbH(Mar. 10, 1999).
Italian Patent Application No. 101995900431047 filed Mar. 28, 1995 and published Sep. 28, 1996 entitled "Syringe Actuator Gun".

(56) References Cited

OTHER PUBLICATIONS

Italian Patent Application No. 101995900437124 filed Apr. 27, 1995 and published Oct. 27, 1996 entitled "Syringe for the Injection of Large Quantities of Liquid, Such as Disinfectant, Preservative, Medicinal Liquids or the Like".

Italian Patent Application No. 101997900585879 filed Mar. 28, 1997 and published Sep. 28, 1998 entitled "Bayonet Connection Between a Spray Pump and a Bottle of a Substance Tobe Sprayed".

Italian Patent Application No. 101999900781373 filed Aug. 13, 1999 and published Feb. 13, 2001, entitled "Device for the Infusion of Drugs".

Italian Patent Application No. 101999900809451 filed Dec. 21, 1999 and published Jun. 21, 2001, entitled "Syringe for the Infusion of Drugs".

Italian Patent Application No. 201998900725470 filed Dec. 18, 1998 and published Jun. 18, 2000 entitled "Solenoid Valve With Sleeve Provided With Bayonet Mount and Means to Lockit in Position".

Liebel-Flarsheim company—Angiomat 6000 Digital Injection System Operator's Manual, 600950 Rev 1 (1990); p. 3-6 to 3-8, 4-52 to 4-56.

Mallinckrodt; Pharmaceuticals., "Power Injectors for Diagnostic Imaging", 2013.

Marc; Green PhD, "Visual Expert Human Factors: Color Functionality in Tradedress: A Case Example", 2013.

Medrad Envision CT Injector Operation Manual, EOM 700E, 92401-T-123 Rev E, Copyright 1995.

Medrad Envision CT Injector Operation Manual, EOM 700E, 92401-T-123 Rev E, pp. 2-10 to 2-11 and pp. 2-30 to 2-35(Copyright 1995).

Medrad, Mark V/Mark V Plus Injector Operation Manual, KMP 805P Rev. B (1990); pp. 1-18 to 1-28, 3-7 to 3-13, 14-1 to 14-4.

Medtron; Ag., "Injektron CT 2, Computer Tomography", 2004.

Sidam; Medical Devices., "Injector Syringe With Automatic Three-Way Valve (received Jul. 9, 2014)".

* cited by examiner

SYSTEM AND METHOD FOR SYRINGE PLUNGER ENGAGEMENT WITH AN INJECTOR

CROSS-REFERENCE TO RELATED APPLICATION

The present application is a U.S. national phase application under 35 U.S.C. § 371 of PCT International Application No. PCT/US2021/037574, filed Jun. 16, 2021, and claims priority to U.S. Provisional Application No. 62/705,265, filed on Jun. 18, 2020, the disclosures of which are incorporated by reference herein in their entireties.

BACKGROUND OF THE DISCLOSURE

Field of the Disclosure

The present disclosure relates generally to a system including a front-loading syringe and/or pressure jacket for use with a fluid injector and, further, to a connection interface for securing a syringe plunger to a piston of the fluid injector and to a method for engaging and disengaging the syringe plunger to and from the piston of the fluid injector.

Description of Related Art

In many medical diagnostic and therapeutic procedures, a medical practitioner injects a patient with one or more medical fluids. A number of injector-actuated syringes and fluid injectors for pressurized injection of fluids, such as a contrast solution (often referred to simply as "contrast"), a flushing agent (such as saline, or Ringer's lactate), and other medical fluids have been developed for use in contrast enhanced imaging procedures such as angiography, computed tomography (CT), ultrasound, magnetic resonance imaging (MRI), positron emission tomography (PET), and other imaging procedures. In general, these fluid injectors are designed to deliver a preset amount of one or more fluids at a preset flow rate.

Typically, fluid injectors have at least one drive member, such as a piston, that connects to a syringe, for example, via connection with a plunger or an engagement feature on a proximal end wall of the syringe. The syringe may include a rigid barrel with the syringe plunger being slidably disposed within the barrel. The at least one drive member is configured to drive the plunger in a proximal and/or distal direction relative to a longitudinal axis of the barrel to draw fluid into or deliver the fluid from the syringe barrel.

Various connection interfaces have been developed to facilitate the engagement of a syringe plunger to and from a piston of the fluid injector. In some embodiments, the syringe having a retention feature is inserted into a syringe port on the fluid injector by aligning the syringe with a corresponding locking feature provided on the fluid injector. Such alignment also aligns the plunger in the syringe with the piston on the fluid injector such that the piston can engage the plunger and reciprocally drive the plunger through the syringe barrel to withdraw fluid into the syringe barrel or deliver fluid from and into the syringe barrel. In other embodiments, upon initial engagement with the plunger, the piston is rotated, in a clockwise or counter-clockwise direction, until the piston engages a catch on the plunger. In further embodiments, the piston has radially-extendable pins that engage a lip on the plunger.

Many of the existing connection interfaces have construction that requires a complex piston head with various sensor elements and active engagement structures. There is a need in the art for an improved connection interface that allows for a simpler and easier engagement and disengagement of the syringe plunger to and from the piston of the fluid injector. There is a further need in the art for reducing or eliminating the need for the operator to rotationally align the syringe with the fluid injector prior to engagement of the syringe plunger with the piston of the fluid injector. While various syringe connection interfaces and methods are known in the medical field, improved connection interfaces between the syringe plunger and the piston of the fluid injector and methods for engaging and disengaging the syringe plunger to and from the piston of the fluid injector continue to be in demand.

SUMMARY OF DISCLOSURE

There is need in the art for an improved connection interface between a syringe plunger and a piston of a fluid injector that overcomes the deficiencies of the prior art. There is additional need for improved methods for engaging and disengaging a syringe plunger to and from a piston of a fluid injector to allow ready loading or removal of a syringe to and from a fluid injector.

In accordance with some embodiments, a plunger for use with a syringe may include a plunger body defining a central longitudinal axis and having a proximal end, a distal end, and a circumferential sidewall connecting the proximal end and the distal end; and at least one retaining member associated with and extending proximally from the plunger body, the at least one retaining member comprising: a first end connected to the plunger body; a second end proximal to the first end and radially and resiliently deflectable relative to the first end; and at least one catch on the second end, wherein the at least one retaining member may have an outer surface configured to engage a plunger engagement sleeve of a plunger engagement mechanism on a piston of a fluid injector system when the plunger may be in a locked state with the piston, wherein the at least one retaining member may have an inner surface configured to engage a plunger engagement post of the plunger engagement mechanism when the plunger may be in the locked state with the piston, wherein the at least one catch may be configured to engage a locking feature on one of the plunger engagement sleeve and the plunger engagement post when the plunger may be in the locked state with the piston to prevent axial movement of the plunger relative to the piston, and wherein the at least one catch may be configured to radially deflect the second end of the at least one retaining member upon axial movement of the piston relative to the plunger in an unlocked state of the plunger from the piston due to engagement of the at least one catch with the locking feature on one of the plunger engagement sleeve and the plunger engagement post.

In accordance with some embodiments, the at least one retaining member may include a plurality of retaining members spaced apart around the central longitudinal axis. The plurality of retaining members may be spaced apart at equal intervals around the central longitudinal axis. The at least one retaining member may extends proximally in a direction parallel with the central longitudinal axis, or in a direction angled relative to the central longitudinal axis. The at least one retaining member may be linearly or curvilinearly contiguous between the first end and the second end. The plunger may be configured to engage the plunger engagement mechanism regardless of angular orientation of the plunger relative to the piston of the fluid injector.

In accordance with some embodiments, the at least one catch may have a first surface at a proximal end of the at least one catch configured for engaging a distal end of the locking feature on one of the plunger engagement sleeve and the plunger engagement post during engagement of the plunger to the piston, and a second surface at a distal end of the at least one catch configured for engaging a proximal end of the locking feature on one of the plunger engagement sleeve and the plunger engagement post during disengagement of the plunger from the piston.

In accordance with some embodiments, the at least one catch may protrude radially inward from the inner surface of the at least one retaining member in a direction toward the central longitudinal axis or radially outward from the outer surface of the at least one retaining member in a direction away from the central longitudinal axis. The at least one catch may define a locking recess for receiving at least a portion of the plunger engagement mechanism when the plunger is connected to the piston. The at least one catch may protrude radially inward from the inner surface of the at least one retaining member in a direction toward the central longitudinal axis, and the at least one catch may be configured to be received within the locking feature that may be shaped as a locking groove protruding radially inward from an outer surface of the plunger engagement post when the plunger may be in the locked state with the piston.

In accordance with some embodiments, the plunger body may have conical-shaped portion at the distal end and a cylindrical-shaped portion at the proximal end. The at least one retaining member may protrude proximally from an inner surface of the conical-shaped portion. A plurality of release tabs may protrude radially inward from an inner surface of the cylindrical-shaped portion or proximally from the inner surface of the cylindrical-shaped portion, each of the plurality of release tabs configured for interacting with the plunger engagement sleeve to effect a release of the plunger from the piston upon rotation of the plunger about the central longitudinal axis. A proximal end of each of the plurality of release tabs may have a pointed guide surface.

In accordance with some embodiments, a plunger cover may cover at least a portion of a distal surface of the plunger body and may include a seal disposed around at least a portion of the circumferential sidewall of the plunger body.

In accordance with some embodiments, the plunger may be configured to be slidably positioned within a barrel of a syringe. The plunger may be configured for reciprocal movement within the barrel of the syringe.

In accordance with some embodiments, a fluid injector system may include at least one reciprocally operable piston having a piston head; and a plunger engagement mechanism associated with the piston head and configured for engaging a plunger of a syringe connected to the fluid injector system for reciprocally driving the plunger in the syringe due to movement of the at least one piston, the plunger engagement mechanism may include: a plunger engagement sleeve having a hollow body; a plunger engagement post receivable within the hollow body of the plunger engagement sleeve; and an actuator operatively connected to one of the plunger engagement sleeve and the plunger engagement post, and configured for moving one of the plunger engagement sleeve and the plunger engagement post between an engaged position and a disengaged position, wherein, in the engaged position, the plunger engagement post may be positioned within the hollow body of the plunger engagement sleeve to capture at least one resiliently flexible retaining member associated with the plunger in a receiving space between the plunger engagement collar and the plunger engagement post, and wherein, in the disengaged position, the plunger engagement post may be positioned at least partially outside of the hollow body of the plunger engagement sleeve to permit flexible insertion or removal of the at least one resiliently flexible retaining member of the plunger from the receiving space.

In accordance with some embodiments, the actuator may be a rotary electric motor, a linear electric motor, a linear actuator, or a solenoid. In accordance with some embodiments, the actuator may be manually operated. The actuator may have an engaged state for moving one of the plunger engagement sleeve and the plunger engagement post to the engaged position and a disengaged state for moving one of the plunger engagement sleeve and the plunger engagement post to the disengaged position. The actuator may be automatically moved to the disengaged state during power loss to the actuator. The actuator may be in the engaged state only during proximal movement of the at least one piston. At least one biasing element may be provided for moving the actuator from the engaged state to the disengaged state.

In accordance with some embodiments, rotational movement of the actuator may move one of the plunger engagement sleeve and the plunger engagement post proximally or distally in a linear direction. In accordance with some embodiments, linear movement of the actuator may move one of the plunger engagement sleeve and the plunger engagement post proximally or distally in a linear direction. The actuator may be operatively connected to a controller configured for controlling actuation of the actuator.

In accordance with some embodiments, one of the plunger engagement sleeve and the plunger engagement sleeve may be linearly or rotatably movable relative to the piston, while the other of the plunger engagement sleeve and the plunger engagement sleeve may be stationary relative to the piston. The plunger engagement post and the plunger engagement collar may be linearly or rotatably movable relative to the piston.

In accordance with some embodiments, at least one sensor may be configured for detecting a position of at least one of the plunger engagement collar and the plunger engagement post between the engaged position and the disengaged position. A plunger detection sensor may be configured for detecting a presence of the at least one retaining member of the plunger in the receiving space between the plunger engagement collar and the plunger engagement post.

In accordance with some embodiments, the hollow body of the plunger engagement sleeve may have an opening with a stepped inner diameter that decreases in a direction from a distal end of the plunger engagement sleeve to a proximal end of the plunger engagement sleeve. The plunger engagement post may include a locking groove protruding radially inward from an outer surface of the plunger engagement post, and the locking groove may be configured for receiving at least one catch on the at least retaining member of the plunger. A distal edge of the locking groove may be configured for flexibly deflecting the at least retaining member of the plunger during axial movement of the plunger relative to the piston to move the at least one catch of the at least one retaining member out of engagement with the locking groove when one of the plunger engagement sleeve and the plunger engagement post may be moved to the disengaged position. The plunger engagement post may have a body with a stepped outer diameter that decreases in a direction from a distal end of the plunger engagement post to a proximal end of the plunger engagement post.

In accordance with some embodiments, the plunger engagement collar may include a locking feature protruding radially inward from an inner surface of the plunger engagement collar. The locking feature may be configured for engaging at least one catch on the at least retaining member of the plunger when one of the plunger engagement sleeve and the plunger engagement post may be moved to the engaged position. The locking feature may be configured for flexibly deflecting the at least retaining member of the plunger during axial movement of the plunger relative to the piston to move the at least one catch of the at least one retaining member out of engagement with the locking feature when one of the plunger engagement sleeve and the plunger engagement post may be moved to the disengaged position.

In accordance with some embodiments, the fluid injector system further may include the syringe, the syringe having a barrel having a barrel proximal end, a barrel distal end having a discharge nozzle, and a barrel sidewall extending between the barrel proximal end and the barrel distal end; and the plunger slidably disposed within the barrel and reciprocally movable between the barrel proximal end and the barrel distal end.

In accordance with some embodiments, the plunger may include: a plunger body defining a central longitudinal axis and having a proximal end, a distal end, and a circumferential sidewall connecting the proximal end and the distal end; and the at least one retaining member associated with and extending proximally from the plunger body.

In accordance with some embodiments, the at least one retaining member may include a first end connected to the plunger body; a second end proximal to the first end and radially and resiliently deflectable relative to the first end; and at least one catch on the second end, wherein the at least one retaining member may have an outer surface configured to engage the plunger engagement sleeve when the plunger may be engaged with the piston, wherein the at least one retaining member may have an inner surface configured to engage the plunger engagement post when the plunger may be engaged with the piston, wherein the at least one catch may be configured to engage a locking feature on one of the plunger engagement sleeve and the plunger engagement post when the plunger may be engaged with the piston to prevent axial movement of the plunger relative to the piston, and wherein the at least one catch may be configured to radially deflect the second end of the at least one retaining member upon axial movement of the piston relative to the plunger in a disengaged state of the plunger due to contact of the at least one catch with the locking feature.

In accordance with some embodiments, the plunger may be configured to engage the plunger engagement mechanism regardless of angular orientation of the plunger relative to the piston of the fluid injector. The at least one catch may protrude radially inward from the inner surface of the at least one retaining member in a direction toward the central longitudinal axis. The at least one catch may be configured to be received within the locking feature that may be shaped as a locking groove protruding radially inward from an outer surface of the plunger engagement post when the plunger may be in the locked state with the piston.

In accordance with some embodiments, the at least one catch may protrude radially inward from the inner surface of the at least one retaining member in a direction toward the central longitudinal axis. In accordance with some embodiments, the at least one catch may protrude radially outward from the outer surface of the at least one retaining member in a direction away from the central longitudinal axis.

In accordance with some embodiments, the plunger body may have conical-shaped portion at the distal end and a cylindrical-shaped portion at the proximal end. The at least one retaining member may protrude proximally from an inner surface of the conical-shaped portion. A plurality of release tabs may protrude radially inward from an inner surface of the cylindrical-shaped portion, each of the plurality of release tabs configured for interacting with the plunger engagement sleeve to effect a release of the plunger from the piston upon rotation of the plunger about the central longitudinal axis. A proximal end of each of the plurality of release tabs may have a pointed guide surface.

In accordance with some embodiments, a fluid injector system may include: at least one reciprocally operable piston having a piston head; and a plunger engagement mechanism associated with the piston head and configured for engaging a plunger of a syringe connected to the fluid injector system for reciprocally driving the plunger in the syringe due to movement of the at least one piston, the plunger engagement mechanism comprising: a plunger engagement sleeve having a hollow body with a longitudinal axis; a plunger engagement post receivable within the hollow body of the plunger engagement sleeve and axially movable relative to the plunger engagement sleeve between an engaged position and a disengaged position, wherein the plunger engagement sleeve may be rotatable about the longitudinal axis between a first position and a second position, wherein the plunger engagement post may be movable axially along the longitudinal axis from the engaged position to the disengaged position via rotation of the plunger engagement sleeve.

In accordance with some embodiments, the plunger engagement post may be movable axially from a proximal end of the piston toward a distal end of the piston. The plunger release sleeve may include a plurality of plunger release teeth protruding radially outward from an outer surface of the hollow body. The plurality of plunger release teeth may be configured to engage a plurality of release tabs on the plunger such that rotation of the plunger about a plunger longitudinal axis causes a rotation of the plunger engagement sleeve about the longitudinal axis.

In accordance with some embodiments, a plunger release sleeve may surround at least a portion of the plunger engagement sleeve, wherein the plunger release sleeve may be configured to rotate about the longitudinal axis with rotation of the plunger engagement sleeve. The plunger release sleeve may include an opening having a ramped surface that may be angled relative to a direction of the longitudinal axis in a direction from a distal end of the plunger release sleeve toward a proximal end of the plunger release sleeve.

In accordance with some embodiments, the plunger engagement post may have a guiding pin extending in a direction perpendicular to the longitudinal axis, and wherein the guiding pin may be received within the opening of the plunger release sleeve. Rotation of the plunger engagement sleeve may cause a corresponding rotation of the plunger release sleeve. The guiding pin may be guided along the ramped surface from a proximal end toward a distal end of the ramped surface, thereby moving the plunger engagement post from the engaged position to the disengaged position.

In accordance with some embodiments, a biasing member may be operatively connected to the plunger engagement sleeve and the plunger engagement post. The biasing member may be configured to bias the plunger engagement sleeve to the first position.

In accordance with some embodiments, an actuator operatively connected to the plunger engagement post and configured for moving the plunger engagement post between the engaged position and the disengaged position. In the engaged position, the plunger engagement post may be positioned within the hollow body of the plunger engagement sleeve and may be configured to capture at least one resiliently flexible retaining member associated with the plunger in a receiving space between the plunger engagement collar and the plunger engagement post. In the disengaged position, the plunger engagement post may be positioned at least partially outside of the hollow body of the plunger engagement sleeve to permit flexible insertion or removal of the at least one resiliently flexible retaining member of the plunger from the receiving space.

In accordance with some embodiments, the actuator may be a rotary electric motor, a linear electric motor, a linear actuator, or a solenoid. In accordance with some embodiments, the actuator may be manually operated. The actuator may have engaged state for moving one of the plunger engagement sleeve and the plunger engagement post to the engaged position and a disengaged state for moving one of the plunger engagement sleeve and the plunger engagement post to the disengaged position. The actuator may be automatically moved to the disengaged state during power loss to the actuator. The actuator may be in the engaged state only during proximal movement of the at least one piston.

In accordance with some embodiments, at least one biasing element for moving the actuator from the engaged state to the disengaged state. Rotational or linear movement of the actuator moves one of the plunger engagement sleeve and the plunger engagement post proximally or distally in a linear direction. The actuator may be operatively connected to a controller configured for controlling actuation of the actuator.

In accordance with some embodiments, at least one sensor may be configured for detecting a position of at least one of the plunger engagement collar and the plunger engagement post between the engaged position and the disengaged position. A plunger detection sensor may be configured for detecting a presence of the at least one retaining member of the plunger in the receiving space between the plunger engagement collar and the plunger engagement post.

In accordance with some embodiments, the hollow body of the plunger engagement sleeve may have an opening with a stepped inner diameter that decreases in a direction from a distal end of the plunger engagement sleeve to a proximal end of the plunger engagement sleeve. The plunger engagement post may include a locking groove protruding radially inward from an outer surface of the plunger engagement post, and wherein the locking groove may be configured for receiving at least one catch on at least retaining member of the plunger. A distal edge of the locking groove may be configured for flexibly deflecting the at least retaining member of the plunger during axial movement of the plunger relative to the piston to move the at least one catch of the at least one retaining member out of engagement with the locking groove when one of the plunger engagement sleeve and the plunger engagement post may be moved to the disengaged position.

In accordance with some embodiments, the fluid injector system further may include the syringe, the syringe having: a barrel having a barrel proximal end, a barrel distal end having a discharge nozzle, and a barrel sidewall extending between the barrel proximal end and the barrel distal end; and the plunger slidably disposed within the barrel and reciprocally movable between the barrel proximal end and the barrel distal end.

In accordance with some embodiments, the plunger may include: a plunger body defining a central longitudinal is and having a proximal end, a distal end, and a circumferential sidewall connecting the proximal end and the distal end; and the at least one retaining member associated with and extending proximally from the plunger body.

In accordance with some embodiments, the at least one retaining member may include: a first end connected to the plunger body; a second end proximal to the first end and radially and resiliently deflectable relative to the first end; and at least one catch on the second end, wherein the at least one retaining member may have an outer surface configured to engage the plunger engagement sleeve when the plunger may be engaged with the piston, wherein the at least one retaining member may have an inner surface configured to engage the plunger engagement post when the plunger may be engaged with the piston, wherein the at least one catch may be configured to engage a locking feature on one of the plunger engagement sleeve and the plunger engagement post when the plunger may be engaged with the piston to prevent axial movement of the plunger relative to the piston, and wherein the at least one catch may be configured to radially deflect the second end of the at least one retaining member upon axial movement of the piston relative to the plunger in a disengaged state of the plunger due to contact of the at least one catch with the locking feature.

In accordance with some embodiments, the plunger may be configured to engage the plunger engagement mechanism regardless of angular orientation of the plunger relative to the piston of the fluid injector.

In accordance with some embodiments, the at least one catch may protrude radially inward from the inner surface of the at least one retaining member in a direction toward the central longitudinal axis, and the at least one catch may be configured to be received within the locking feature that may be shaped as a locking groove protruding radially inward from an outer surface of the plunger engagement post when the plunger may be in the locked state with the piston.

In accordance with some embodiments, the at least one catch may protrude radially inward from the inner surface of the at least one retaining member in a direction toward the central longitudinal axis, or the at least one catch may protrude radially outward from the outer surface of the at least one retaining member in a direction away from the central longitudinal axis. The at least one catch may define a locking recess for receiving at least a portion of the plunger engagement mechanism when the plunger may be connected to the piston.

In accordance with some embodiments, the plunger body may have conical-shaped portion at the distal end and a cylindrical-shaped portion at the proximal end. The at least one retaining member may protrude proximally from an inner surface of the conical-shaped portion. A plurality of release tabs may protrude radially inward from an inner surface of the cylindrical-shaped portion or proximally from the inner surface of the cylindrical-shaped portion, each of the plurality of release tabs configured for interacting with the plunger engagement sleeve to effect a release of the plunger from the piston upon rotation of the plunger about the central longitudinal axis. A proximal end of each of the plurality of release tabs may have a pointed guide surface.

Further embodiments or aspects of the present disclosure are described in the following numbered clauses:

Clause 1: A plunger for use with a syringe, the plunger comprising: a plunger body defining a central longitudinal axis and having a proximal end, a distal end, and a circumferential sidewall connecting the proximal end and the distal end; and at least one retaining member associated with and extending proximally from the plunger body, the at least one retaining member comprising: a first end connected to the plunger body; a second end proximal to the first end and radially and resiliently deflectable relative to the first end; and at least one catch on the second end, wherein the at least one retaining member has an outer surface configured to engage a plunger engagement sleeve of a plunger engagement mechanism on a piston of a fluid injector system when the plunger is in a locked state with the piston, wherein the at least one retaining member has an inner surface configured to engage a plunger engagement post of the plunger engagement mechanism when the plunger is in the locked state with the piston, wherein the at least one catch is configured to engage a locking feature on one of the plunger engagement sleeve and the plunger engagement post when the plunger is in the locked state with the piston to prevent axial movement of the plunger relative to the piston, and wherein the at least one catch is configured to radially deflect the second end of the at least one retaining member upon axial movement of the piston relative to the plunger in an unlocked state of the plunger from the piston due to engagement of the at least one catch with the locking feature on one of the plunger engagement sleeve and the plunger engagement post.

Clause 2. The plunger according to clause 1, wherein the at least one retaining member comprises a plurality of retaining members spaced apart around the central longitudinal axis.

Clause 3. The plunger according to clause 2, wherein the plurality of retaining members are spaced apart at equal intervals around the central longitudinal axis.

Clause 4. The plunger according to any of clauses 1 to 3, wherein the at least one retaining member extends proximally in a direction parallel with the central longitudinal axis.

Clause 5. The plunger according to any of clauses 1 to 3, wherein the at least one retaining member extends proximally in a direction angled relative to the longitudinal axis.

Clause 6. The plunger according to any of clauses 1 to 5, wherein the at least one retaining member is linearly contiguous between the first end and the second end.

Clause 7. The plunger according to any of clauses 1 to 5, wherein the at least one retaining member is curvilinearly contiguous between the first end and the second end.

Clause 8. The plunger according to any of clauses 1 to 7, wherein the plunger is configured to engage the plunger engagement mechanism regardless of angular orientation of the plunger relative to the piston of the fluid injector.

Clause 9. The plunger according to any of clauses 1 to 8, wherein the at least one catch has a first surface at a proximal end of the at least one catch configured for engaging a distal end of the locking feature on one of the plunger engagement sleeve and the plunger engagement post during engagement of the plunger to the piston, and a second surface at a distal end of the at least one catch configured for engaging a proximal end of the locking feature on one of the plunger engagement sleeve and the plunger engagement post during disengagement of the plunger from the piston.

Clause 10. The plunger according to any of clauses 1 to 9, wherein the at least one catch protrudes radially inward from the inner surface of the at least one retaining member in a direction toward the central longitudinal axis.

Clause 11. The plunger according to any of clauses 1 to 10, wherein the at least one catch protrudes radially outward from the outer surface of the at least one retaining member in a direction away from the central longitudinal axis.

Clause 12. The plunger according to any of clauses 1 to 11, wherein the at least one catch defines a locking recess for receiving at least a portion of the plunger engagement mechanism when the plunger is connected to the piston.

Clause 13. The plunger according to any of clauses 1 to 12, wherein the at least one catch protrudes radially inward from the inner surface of the at least one retaining member in a direction toward the central longitudinal axis, and wherein the at least one catch is configured to be received within the locking feature that is shaped as a locking groove protruding radially inward from an outer surface of the plunger engagement post when the plunger is in the locked state with the piston.

Clause 14. The plunger according to any of clauses 1 to 13, wherein the plunger body has conical-shaped portion at the distal end and a cylindrical-shaped portion at the proximal end.

Clause 15. The plunger according to clause 14, wherein the at least one retaining member protrudes proximally from an inner surface of the conical-shaped portion.

Clause 16. The plunger according to clause 14 or 15, further comprising a plurality of release tabs protruding radially inward from an inner surface of the cylindrical-shaped portion or proximally from the inner surface of the cylindrical-shaped portion, each of the plurality of release tabs configured for interacting with the plunger engagement sleeve to effect a release of the plunger from the piston upon rotation of the plunger about the central longitudinal axis Clause 17. The plunger according to clause 16, wherein a proximal end of each of the plurality of release tabs has a pointed guide surface.

Clause 18. The plunger according to any of clauses 1 to 17, further comprising a plunger cover covering at least a portion of a distal surface of the plunger body and comprising a seal disposed around at least a portion of the circumferential sidewall of the plunger body.

Clause 19. The plunger according to any of clauses 1 to 18, wherein the plunger is configured to be slidably positioned within a barrel of a syringe.

Clause 20. The plunger according to clause 19, wherein the plunger is configured for reciprocal movement within the barrel of the syringe.

Clause 21. A fluid injector system comprising: at least one reciprocally operable piston having a piston head; and a plunger engagement mechanism associated with the piston head and configured for engaging a plunger of a syringe connected to the fluid injector system for reciprocally driving the plunger in the syringe due to movement of the at least one piston, the plunger engagement mechanism comprising: a plunger engagement sleeve having a hollow body; a plunger engagement post receivable within the hollow body of the plunger engagement sleeve; and an actuator operatively connected to one of the plunger engagement sleeve and the plunger engagement post, and configured for moving one of the plunger engagement sleeve and the plunger engagement post between an engaged position and a disengaged position, wherein, in the engaged position, the plunger engagement post is positioned within the hollow body of the plunger engagement sleeve to capture at least one resiliently flexible retaining member associated with the plunger in a receiving space between the plunger engagement collar and the plunger engagement post, and wherein, in the disengaged position, the plunger engagement post is positioned at least partially outside of the hollow body of the plunger engagement sleeve to permit flexible insertion or removal of the at least one resiliently flexible retaining member of the plunger from the receiving space.

Clause 22. The fluid injector system according to clause 21, wherein the actuator is a rotary electric motor, a linear electric motor, a linear actuator, or a solenoid.

Clause 23. The fluid injector system according to clause 21, wherein the actuator is manually operated.

Clause 24. The fluid injector system according to any of clauses 21 to 23, wherein the actuator has engaged state for moving one of the plunger engagement sleeve and the plunger engagement post to the engaged position and a disengaged state for moving one of the plunger engagement sleeve and the plunger engagement post to the disengaged position.

Clause 25. The fluid injector system according to any of clauses 21 to 24, wherein the actuator is automatically moved to the disengaged state during power loss to the actuator.

Clause 26. The fluid injector system according to any of clauses 21 to 25, wherein the actuator is in the engaged state only during proximal movement of the at least one piston.

Clause 27. The fluid injector system according to any of clauses 21 to 26, further comprising at least one biasing element for moving the actuator from the engaged state to the disengaged state.

Clause 28. The fluid injector system according to any of clauses 21 to 27, wherein rotational movement of the actuator moves one of the plunger engagement sleeve and the plunger engagement post proximally or distally in a linear direction.

Clause 29. The fluid injector system according to any of clauses 21 to 28, wherein linear movement of the actuator moves one of the plunger engagement sleeve and the plunger engagement post proximally or distally in a linear direction.

Clause 30. The fluid injector system according to any of clauses 21 to 29, wherein the actuator is operatively connected to a controller configured for controlling actuation of the actuator.

Clause 31. The fluid injector system according to any of clauses 21 to 30, wherein one of the plunger engagement sleeve and the plunger engagement sleeve is linearly or rotatably movable relative to the piston, while the other of the plunger engagement sleeve and the plunger engagement sleeve is stationary relative to the piston.

Clause 32. The fluid injector system according to any of clauses 21 to 31, wherein the plunger engagement post and the plunger engagement collar are linearly or rotatably movable relative to the piston.

Clause 33. The fluid injector system according to any of clauses 21 to 32, further comprising at least one sensor configured for detecting a position of at least one of the plunger engagement collar and the plunger engagement post between the engaged position and the disengaged position.

Clause 34. The fluid injector system according to any of clauses 21 to 33, further comprising a plunger detection sensor configured for detecting a presence of the at least one retaining member of the plunger in the receiving space between the plunger engagement collar and the plunger engagement post.

Clause 35. The fluid injector system according to any of clauses 21 to 34, wherein the hollow body of the plunger engagement sleeve has an opening with a stepped inner diameter that decreases in a direction from a distal end of the plunger engagement sleeve to a proximal end of the plunger engagement sleeve.

Clause 36. The fluid injector system according to any of clauses 21 to 35, wherein the plunger engagement post comprises a locking groove protruding radially inward from an outer surface of the plunger engagement post, and wherein the locking groove is configured for receiving at least one catch on the at least retaining member of the plunger.

Clause 37. The fluid injector system according to clause 36, wherein a distal edge of the locking groove is configured for flexibly deflecting the at least retaining member of the plunger during axial movement of the plunger relative to the piston to move the at least one catch of the at least one retaining member out of engagement with the locking groove when one of the plunger engagement sleeve and the plunger engagement post is moved to the disengaged position.

Clause 38. The fluid injector system according to any of clauses 21 to 37, wherein the plunger engagement post has a body with a stepped outer diameter that decreases in a direction from a distal end of the plunger engagement post to a proximal end of the plunger engagement post.

Clause 39. The fluid injector system according to any of clauses 21 to 38, wherein the plunger engagement collar comprises a locking feature protruding radially inward from an inner surface of the plunger engagement collar, and wherein the locking feature is configured for engaging at least one catch on the at least retaining member of the plunger when one of the plunger engagement sleeve and the plunger engagement post is moved to the engaged position.

Clause 40. The fluid injector system according to clause 39, wherein the locking feature is configured for flexibly deflecting the at least retaining member of the plunger during axial movement of the plunger relative to the piston to move the at least one catch of the at least one retaining member out of engagement with the locking feature when one of the plunger engagement sleeve and the plunger engagement post is moved to the disengaged position.

Clause 41. The fluid injector system according to any of clauses 21 to 39, further comprising the syringe, the syringe comprising: a barrel having a barrel proximal end, a barrel distal end having a discharge nozzle, and a barrel sidewall extending between the barrel proximal end and the barrel distal end; and the plunger slidably disposed within the barrel and reciprocally movable between the barrel proximal end and the barrel distal end.

Clause 42. The fluid injector system according to clause 41, wherein the plunger comprises a plunger body defining a central longitudinal axis and having a proximal end, a distal end, and a circumferential sidewall connecting the proximal end and the distal end; and the at least one retaining member associated with and extending proximally from the plunger body.

Clause 43. The fluid injector system according to clause 41 or 42, wherein the at least one retaining member comprises: a first end connected to the plunger body; a second end proximal to the first end and radially and resiliently deflectable relative to the first end; and at least one catch on the second end, wherein the at least one retaining member has an outer surface configured to engage the plunger engagement sleeve when the plunger is engaged with the piston, wherein the at least one retaining member has an inner surface configured to engage the plunger engagement post when the plunger is engaged with the piston, wherein the at least one catch is configured to engage a locking feature on one of the plunger engagement sleeve and the plunger engagement post when the plunger is engaged with the piston to prevent axial movement of the plunger relative to the piston, and wherein the at least one catch is configured to radially deflect the second end of the at least one retaining member upon axial movement of the piston relative to the plunger in a disengaged state of the plunger due to contact of the at least one catch with the locking feature.

Clause 44. The fluid injector system according to any of clauses 41 to 43, wherein the plunger is configured to engage the plunger engagement mechanism regardless of angular orientation of the plunger relative to the piston of the fluid injector.

Clause 45. The fluid injector system according to any of clauses 41 to 44, wherein the at least one catch protrudes radially inward from the inner surface of the at least one retaining member in a direction toward the central longitudinal axis, and wherein the at least one catch is configured to be received within the locking feature that is shaped as a locking groove protruding radially inward from an outer surface of the plunger engagement post when the plunger is in the locked state with the piston.

Clause 46. The fluid injector system according to any of clauses 41 to 45, wherein the at least one catch protrudes radially inward from the inner surface of the at least one retaining member in a direction toward the central longitudinal axis, or wherein the at least one catch protrudes radially outward from the outer surface of the at least one retaining member in a direction away from the central longitudinal axis.

Clause 47. The fluid injector system according to any of clauses 41 to 46, wherein the plunger body has conical-shaped portion at the distal end and a cylindrical-shaped portion at the proximal end.

Clause 48. The fluid injector system according to clause 47, wherein the at least one retaining member protrudes proximally from an inner surface of the conical-shaped portion.

Clause 49. The fluid injector system according to clause 47 or 48, further comprising a plurality of release tabs protruding radially inward from an inner surface of the cylindrical-shaped portion, each of the plurality of release tabs configured for interacting with the plunger engagement sleeve to effect a release of the plunger from the piston upon rotation of the plunger about the central longitudinal axis.

Clause 50. The fluid injector system according to clause 49, wherein a proximal end of each of the plurality of release tabs has a pointed guide surface.

Clause 51. A fluid injector system comprising: at least one reciprocally operable piston having a piston head; and a plunger engagement mechanism associated with the piston head and configured for engaging a plunger of a syringe connected to the fluid injector system for reciprocally driving the plunger in the syringe due to movement of the at least one piston, the plunger engagement mechanism comprising: a plunger engagement sleeve having a hollow body with a longitudinal axis; a plunger engagement post receivable within the hollow body of the plunger engagement sleeve and axially movable relative to the plunger engagement sleeve between an engaged position and a disengaged position, wherein the plunger engagement sleeve is rotatable about the longitudinal axis between a first position and a second position, wherein the plunger engagement post is movable axially along the longitudinal axis from the engaged position to the disengaged position via rotation of the plunger engagement sleeve.

Clause 52. The fluid injector system according to clause 51, wherein the plunger engagement post is movable axially from a proximal end of the piston toward a distal end of the piston.

Clause 53. The fluid injector system according to 51 or 52, wherein the plunger release sleeve comprises a plurality of plunger release teeth protruding radially outward from an outer surface of the hollow body.

Clause 54. The fluid injector system according to clause 53, wherein the plurality of plunger release teeth are configured to engage a plurality of release tabs on the plunger such that rotation of the plunger about a plunger longitudinal axis causes a rotation of the plunger engagement sleeve about the longitudinal axis.

Clause 55. The fluid injector system according to any of clauses 51 to 54, further comprising a plunger release sleeve surrounding at least a portion of the plunger engagement sleeve, wherein the plunger release sleeve is configured to rotate about the longitudinal axis with rotation of the plunger engagement sleeve.

Clause 56. The fluid injector system according to any of clauses 51 to 55, wherein the plunger release sleeve comprises an opening having a ramped surface that is angled relative to a direction of the longitudinal axis in a direction from a distal end of the plunger release sleeve toward a proximal end of the plunger release sleeve.

Clause 57. The fluid injector system according to clause 56, wherein the plunger engagement post has a guiding pin extending in a direction perpendicular to the longitudinal axis, and wherein the guiding pin is received within the opening of the plunger release sleeve.

Clause 58. The fluid injector system according to clause 57, wherein rotation of the plunger engagement sleeve causes a corresponding rotation of the plunger release sleeve, and wherein the guiding pin is guided along the ramped surface from a proximal end toward a distal end of the ramped surface, thereby moving the plunger engagement post from the engaged position to the disengaged position.

Clause 59. The fluid injector system according to any of clauses 51 to 58, further comprising a biasing member operatively connected to the plunger engagement sleeve and the plunger engagement post.

Clause 60. The fluid injector system according to clause 59, wherein the biasing member is configured to bias the plunger engagement sleeve to the first position.

Clause 61. The fluid injector system according to any of clauses 51 to 60, further comprising an actuator operatively connected to the plunger engagement post and configured for moving the plunger engagement post between the engaged position and the disengaged position.

Clause 62. The fluid injector system according to clause 61, wherein, in the engaged position, the plunger engagement post is positioned within the hollow body of the plunger engagement sleeve and is configured to capture at least one resiliently flexible retaining member associated with the plunger in a receiving space between the plunger engagement collar and the plunger engagement post, and wherein, in the disengaged position, the plunger engagement post is positioned at least partially outside of the hollow body of the plunger engagement sleeve to permit flexible insertion or removal of the at least one resiliently flexible retaining member of the plunger from the receiving space.

Clause 63. The fluid injector system according to clause 61 or 62, wherein the actuator is a rotary electric motor, a linear electric motor, a linear actuator, or a solenoid.

Clause 64. The fluid injector system according to any of clauses 61 to 63, wherein the actuator is manually operated.

Clause 65. The fluid injector system according to any of clauses 61 to 63, wherein the actuator has engaged state for moving one of the plunger engagement sleeve and the plunger engagement post to the engaged position and a disengaged state for moving one of the plunger engagement sleeve and the plunger engagement post to the disengaged position.

Clause 66. The fluid injector system according to any of clauses 61 to 65, wherein the actuator is automatically moved to the disengaged state during power loss to the actuator.

Clause 67. The fluid injector system according to any of clauses 61 to 66, wherein the actuator is in the engaged state only during proximal movement of the at least one piston.

Clause 68. The fluid injector system according to any of clauses 61 to 67, further comprising at least one biasing element for moving the actuator from the engaged state to the disengaged state.

Clause 69. The fluid injector system according to any of clauses 61 to 68, wherein rotational movement of the actuator moves one of the plunger engagement sleeve and the plunger engagement post proximally or distally in a linear direction.

Clause 70. The fluid injector system according to any of clauses 61 to 69, wherein linear movement of the actuator moves one of the plunger engagement sleeve and the plunger engagement post proximally or distally in a linear direction.

Clause 71. The fluid injector system according to any of clauses 61 to 70, wherein the actuator is operatively connected to a controller configured for controlling actuation of the actuator.

Clause 72. The fluid injector system according to any of clauses 51 to 71, further comprising at least one sensor configured for detecting a position of at least one of the plunger engagement collar and the plunger engagement post between the engaged position and the disengaged position.

Clause 73. The fluid injector system according to any of clauses 51 to 72, further comprising a plunger detection sensor configured for detecting a presence of the at least one retaining member of the plunger in the receiving space between the plunger engagement collar and the plunger engagement post.

Clause 74. The fluid injector system according to any of clauses 51 to 73, wherein the hollow body of the plunger engagement sleeve has an opening with a stepped inner diameter that decreases in a direction from a distal end of the plunger engagement sleeve to a proximal end of the plunger engagement sleeve.

Clause 75. The fluid injector system according to any of clauses 51 to 74, wherein the plunger engagement post comprises a locking groove protruding radially inward from an outer surface of the plunger engagement post, and wherein the locking groove is configured for receiving at least one catch on at least retaining member of the plunger.

Clause 76. The fluid injector system according to clause 75, wherein a distal edge of the locking groove is configured for flexibly deflecting the at least retaining member of the plunger during axial movement of the plunger relative to the piston to move the at least one catch of the at least one retaining member out of engagement with the locking groove when one of the plunger engagement sleeve and the plunger engagement post is moved to the disengaged position.

Clause 77. The fluid injector system according to any of clauses 51 to 76, further comprising the syringe, the syringe comprising: a barrel having a barrel proximal end, a barrel distal end having a discharge nozzle, and a barrel sidewall extending between the barrel proximal end and the barrel distal end; and the plunger slidably disposed within the barrel and reciprocally movable between the barrel proximal end and the barrel distal end.

Clause 78. The fluid injector system according to clause 77, wherein the plunger comprises: a plunger body defining a central longitudinal axis and having a proximal end, a distal end, and a circumferential sidewall connecting the proximal end and the distal end; and the at least one retaining member associated with and extending proximally from the plunger body.

Clause 79. The fluid injector system according to clause 77 or 78, wherein the at least one retaining member comprises: a first end connected to the plunger body; a second end proximal to the first end and radially and resiliently deflectable relative to the first end; and at least one catch on the second end, wherein the at least one retaining member has an outer surface configured to engage the plunger engagement sleeve when the plunger is engaged with the piston, wherein the at least one retaining member has an inner surface configured to engage the plunger engagement post when the plunger is engaged with the piston, wherein the at least one catch is configured to engage a locking feature on one of the plunger engagement sleeve and the plunger engagement post when the plunger is engaged with the piston to prevent axial movement of the plunger relative to the piston, and wherein the at least one catch is configured to radially deflect the second end of the at least one retaining member upon axial movement of the piston relative to the plunger in a disengaged state of the plunger due to contact of the at least one catch with the locking feature.

Clause 80. The fluid injector system according to any of clauses 77 to 79, wherein the plunger is configured to engage the plunger engagement mechanism regardless of angular orientation of the plunger relative to the piston of the fluid injector.

Clause 81. The fluid injector system according to any of clauses 77 to 80, wherein the at least one catch protrudes radially inward from the inner surface of the at least one retaining member in a direction toward the central longitudinal axis, and wherein the at least one catch is configured to be received within the locking feature that is shaped as a locking groove protruding radially inward from an outer surface of the plunger engagement post when the plunger is in the locked state with the piston.

Clause 82. The fluid injector system according to any of clauses 77 to 81, wherein the at least one catch protrudes radially inward from the inner surface of the at least one retaining member in a direction toward the central longitudinal axis, or wherein the at least one catch protrudes radially outward from the outer surface of the at least one retaining member in a direction away from the central longitudinal axis.

Clause 83. The fluid injector system according to any of clauses 77 to 82, wherein the at least one catch defines a locking recess for receiving at least a portion of the plunger engagement mechanism when the plunger is connected to the piston.

Clause 84. The fluid injector system according to any of clauses 77 to 83, wherein the plunger body has conical-shaped portion at the distal end and a cylindrical-shaped portion at the proximal end.

Clause 85. The fluid injector system according to clause 84, wherein the at least one retaining member protrudes proximally from an inner surface of the conical-shaped portion.

Clause 86. The fluid injector system according to clause 84 or 85, further comprising a plurality of release tabs protruding radially inward from an inner surface of the cylindrical-shaped portion or proximally from the inner surface of the cylindrical-shaped portion, each of the plurality of release tabs configured for interacting with the plunger engagement sleeve to effect a release of the plunger from the piston upon rotation of the plunger about the central longitudinal axis.

Clause 87. The fluid injector system according to clause 86, wherein a proximal end of each of the plurality of release tabs has a pointed guide surface.

These and other features and characteristics of syringes, syringe plungers, pressure jackets and systems having syringes and/or syringe plungers, as well as the methods of operation and functions of the related elements of structures and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only.

DETAILED DESCRIPTION

Figure 1:
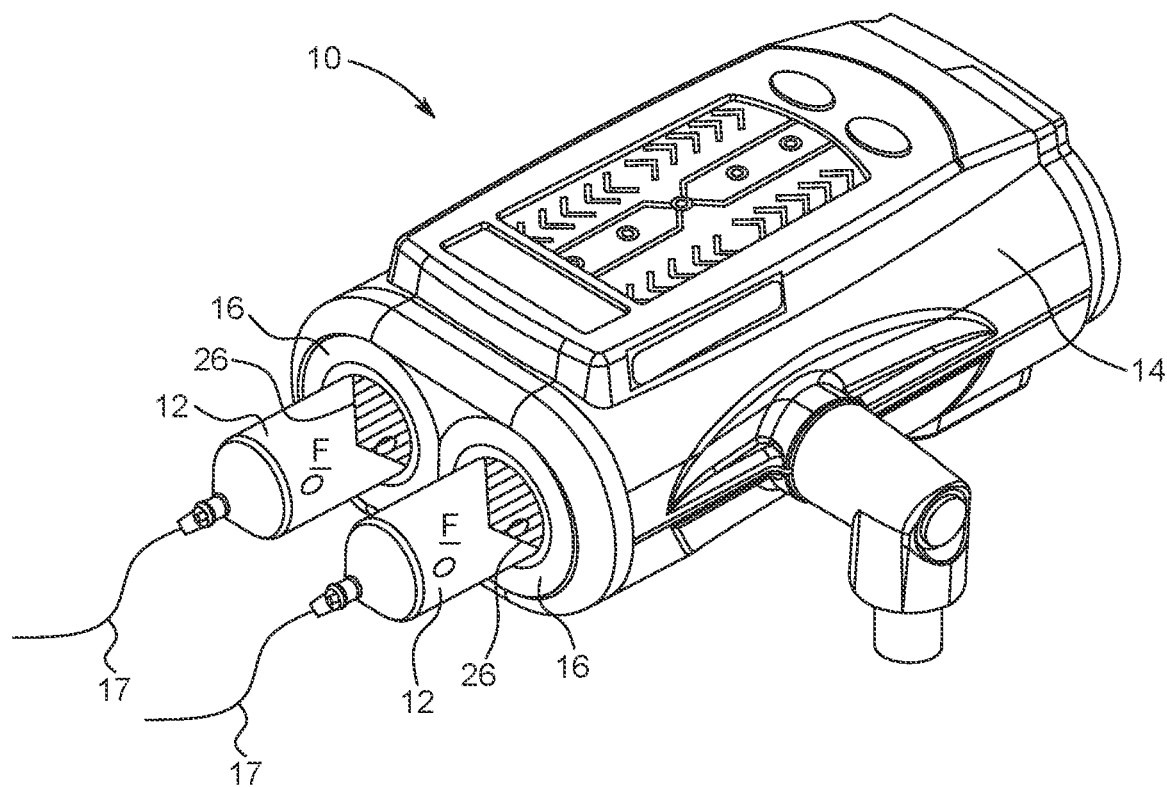
FIG. 1 is a perspective view of a fluid injector system according to one embodiment of the present disclosure.

For purposes of the description hereinafter, the terms "upper", "lower", "right", "left", "vertical", "horizontal", "top", "bottom", "lateral", "longitudinal", and derivatives thereof shall relate to the disclosure as it is oriented in the drawing figures. Spatial or directional terms, such as "left", "right", "inner", "outer", "above", "below", and the like, are not to be considered as limiting as the embodiments described herein can assume various alternative orientations.

As used herein, the singular form of "a", "an", and "the" include plural referents unless the context clearly dictates otherwise. All numbers used in the specification and claims are to be understood as being modified in all instances by the term "about". The terms "approximately", "about", and "substantially" mean a range of plus or minus ten percent of the stated value.

Unless otherwise indicated, all ranges or ratios disclosed herein are to be understood to encompass the beginning and ending values and any and all subranges or subratios subsumed therein. For example, a stated range or ratio of "1 to 10" should be considered to include any and all subranges or subratios between (and inclusive of) the minimum value of 1 and the maximum value of 10; that is, all subranges or subratios beginning with a minimum value of 1 or more and ending with a maximum value of 10 or less. The ranges and/or ratios disclosed herein represent the average values over the specified range and/or ratio.

As used herein, the term "at least one of" is synonymous with "one or more of". For example, the phrase "at least one of A, B, and C" means any one of A, B, and C, or any combination of any two or more of A, B, and C. For example, "at least one of A, B, and C" includes one or more of A alone; or one or more B alone; or one or more of C alone; or one or more of A and one or more of B; or one or more of A and one or more of C; or one or more of B and one or more of C; or one or more of all of A, B, and C. Similarly, as used herein, the term "at least two of" is synonymous with "two or more of". For example, the phrase "at least two of D, E, and F" means any combination of any two or more of D, E, and F. For example, "at least two of D, E, and F" includes one or more of D and one or more of E; or one or more of D and one or more of F; or one or more of E and one or more of F; or one or more of all of D, E, and F.

The terms "first", "second", and the like are not intended to refer to any particular order or chronology, but refer to different conditions, properties, or elements. All documents referred to herein are "incorporated by reference" in their entirety. The term "at least" is synonymous with "greater than or equal to". The term "not greater than" is synonymous with "less than or equal to".

It is to be understood that the disclosure may assume alternative variations and step sequences, except where expressly specified to the contrary. It is also to be understood that the specific devices and processes illustrated in the attached drawings, and described in the following specification, are simply exemplary aspects of the disclosure. Hence, specific dimensions and other physical characteristics related to the examples disclosed herein are not to be considered as limiting.

As used herein, the terms "parallel" or "substantially parallel" mean a relative angle as between two objects (if extended to theoretical intersection), such as elongated objects and including reference lines, that is from 0° to 5°, or from 0° to 3°, or from 0° to 2°, or from 0° to 1°, or from 0° to 0.5°, or from 0° to 0.25°, or from 0° to 0.1°, inclusive of the recited values.

As used herein, the terms "perpendicular" or "substantially perpendicular" mean a relative angle as between two objects at their real or theoretical intersection is from 85° to 90°, or from 87° to 90°, or from 88° to 90°, or from 89° to 90°, or from 89.5° to 90°, or from 89.75° to 90°, or from 89.9° to 90°, inclusive of the recited values.

When used in relation to a component of a fluid delivery system, such as a fluid reservoir, a syringe, a pressure jacket, or a fluid line, the term "distal" refers to a portion of said component nearest to a patient. When used in relation to a component of an injector system, such as a fluid reservoir, a syringe, a pressure jacket, or a fluid line, the term "proximal" refers to a portion of said component nearest to the injector of the injector system (i.e. the portion of said component farthest from the patient). When used in relation to a component of a fluid delivery system, such as a fluid line, the term "upstream" refers to a direction away from the patient and towards the injector of the injector system. For example, if a first component is referred to as being "upstream" of a second component, the first component is located nearer to the injector than the second component is to the injector. When used in relation to a component of a fluid delivery system such as a fluid line, the term "downstream" refers to a direction towards the patient and away from the injector of the fluid delivery system. For example, if a first component is referred to as being "downstream" of a second component, the first component is located nearer to the patient than the second component is to the patient.

When used in relation to movement of components of a fluid delivery system, such as one or more components of a plunger engagement mechanism associated with a piston, the terms "automatic" or "automatically" refer to movement of the one or more components without manual assistance.

While the systems and apparatuses described herein are with reference to computed tomography (CT) contrast injection systems, angiography (CV) contrast injection systems, positron emission tomography (PET) contrast injection systems, and magnetic resonance imaging (MRI) contrast injection systems, other pressurized injection protocols may also incorporate the various embodiments described herein for securing a syringe plunger to a piston of the fluid injector.

Referring to the drawings in which like reference characters refer to like parts throughout the several views thereof, the present disclosure is generally directed to a syringe plunger and a connection interface for connecting the syringe plunger to a piston of a fluid injector. Various embodiments are directed to syringe plungers that may be connected to and disconnected from the piston. In various embodiments, such pistons may be manually, mechanically, hydraulically, or electrically activated. Furthermore, the present disclosure provides a quick and easy solution for engaging and/or disengaging the syringe plunger to and from the piston without a specific rotational orientation or alignment of the plunger relative to the piston. For example, the piston may be advanced forward until it engages with the plunger, regardless of orientation of the plunger about its longitudinal axis relative to the longitudinal axis of the piston, as will be described in greater detail herein. In addition, when the piston may be attached to the plunger, a simple rotation of the plunger, for example by rotation of the syringe, about its longitudinal axis relative to the piston may cause detachment of the two elements. In other embodiments, engagement and disengagement of the piston to the plunger may be performed by a fluid injector controller, such as during the initiation of and completion of an fluid injection protocol, either automatically as part of a programmed injection protocol or initiated by a user, for example by user input to a fluid injector controller. In further embodiments or aspects, the present disclosure is also generally directed to pressure jackets and caps for pressure jackets, wherein the same connection interface for connecting the syringe plunger to the piston of the fluid injector may be used for connecting the pressure jacket to the fluid injector, and/or the cap of the pressure jacket to the pressure jacket itself.

With reference to FIG. 1, a non-limiting example of a fluid injector system 10 (hereinafter referred to as "injector 10"), such as an automated or powered fluid injector, is adapted to interface with and actuate at least one syringe 12 and corresponding plunger 26, each of which may be independently filled with a medical fluid F, such as contrast media, saline solution, or any desired medical fluid. The injector 10 may be used during a medical procedure to inject the medical fluid into the body of a patient by driving plunger 26 of the at least one syringe 12 with at least one driving member, such as at least one piston 13 (shown in FIG. 2). The injector 10 may be a multi-syringe injector, wherein several syringes 12 may be oriented in a side-by-side or other relationship and include plungers 26 separately actuated by respective pistons 13 associated with the injector 10. In embodiments with two syringes arranged in a side-by-side relationship and filled with two different medical fluids, the injector 10 may deliver fluid from one or both of the syringes 12.

Figure 2:
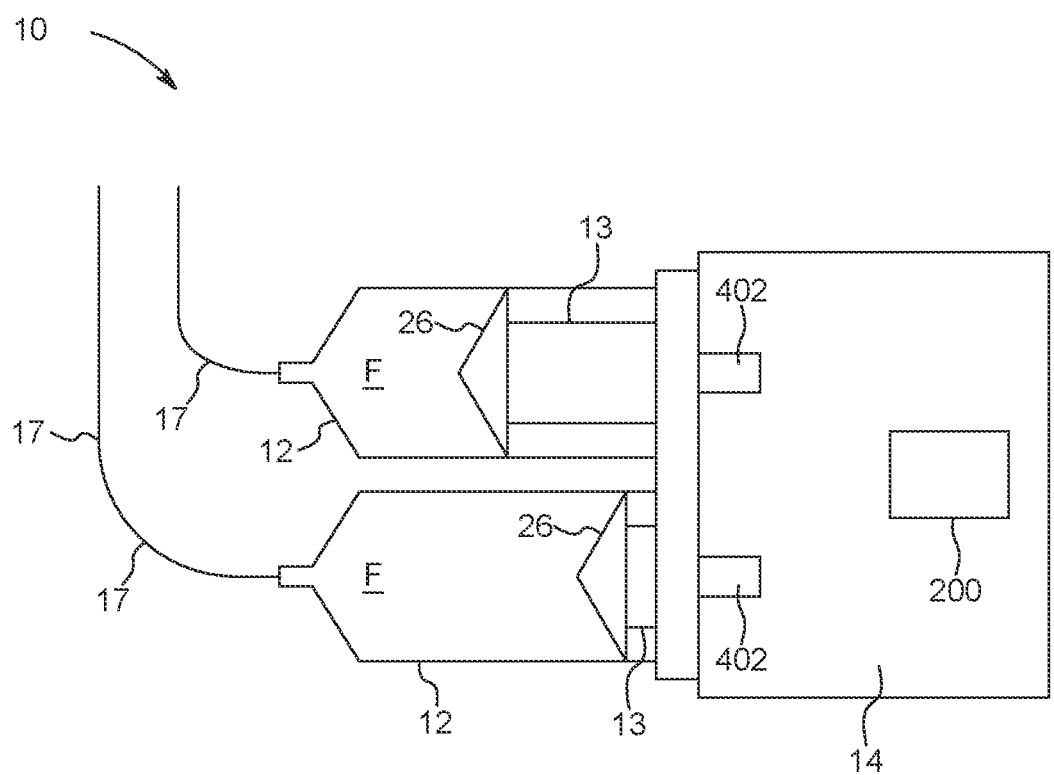
FIG. 2 is a schematic representation of the fluid injector system of FIG. 1.

The injector 10 may be enclosed within a housing 14 formed from a suitable structural material, such as plastic or metal. The housing 14 may be of various shapes and sizes depending on the desired application. The injector 10 includes at least one syringe port 16 for connecting the at least one syringe 12 to a respective piston 13 (FIG. 2).

At least one fluid path set 17 may be fluidly connected with the at least one syringe 12 for delivering medical fluid F from the at least one syringe 12 to a catheter, needle, or other fluid delivery connection (not shown) inserted into a patient at a vascular access site. Fluid flow from the at least one syringe 12 may be regulated by a controller 200 (FIG. 2). The controller 200 may operate various pistons, piston mechanical components (such as components for engagement and disengagement of the piston with a plunger), valves, and/or flow regulating structures to regulate the delivery of the medical fluid, such as saline solution and contrast, to the patient based on user selected injection parameters. One aspect of a suitable front-loading fluid injector that may be modified for use with the above-described system including at least one syringe and at least one piston for engaging and releasable retaining a plunger of a syringe engaged with the fluid injector described herein with reference to FIGS. 1-2 is disclosed in U.S. Pat. No. 5,383,858, whereas another aspect of relevant multi-fluid delivery systems that may be modified for use with the present system are found in U.S. Pat. Nos. 7,553,294; 7,666,169; International Patent Application No. PCT/US2012/037491; and U.S. Application Publication No. 2014/0027009; the disclosures of each of which are incorporated herein by reference. Other embodiments may include new fluid injector systems designed to include various embodiments of the connection interface between the piston 13 of the injector 10 and the plunger 26 of the syringe 12 described herein.

Figure 3:
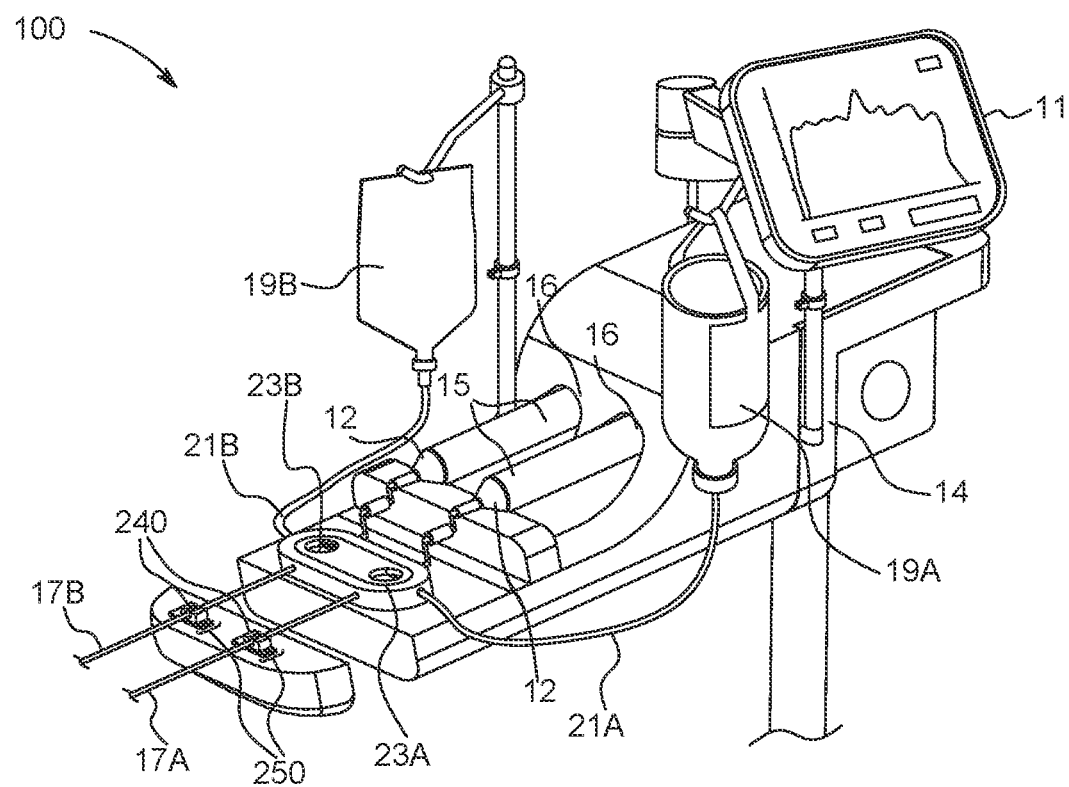
FIG. 3 is a perspective view of a fluid injector system according to another embodiment of the present disclosure.

Referring to FIG. 3, a representative embodiment of a dual syringe angiography injector system 100 (hereinafter referred to as "injector 100") is illustrated. The injector 100 is configured for injection of two medical fluids through a first fluid path 17A for a medical fluid, such as an imaging contrast media for an angiography injection procedure, and a second fluid path 17B for a flushing fluid, such as saline or Ringer's lactate. The injector 100 may include an injector housing 14 having two syringe ports 16 configured to engage two syringes 12.

The injector housing 14 may further include at least one user interface 11 through which an operator can view and control the status of an injection procedure. The user interface 11 may be in operative communication with a controller (similar to controller 200 described herein, FIG. 2) which sends and receives commands to and from user interface 11.

The injector 100 may further include at least one upstream air detector 240 for detecting one or more air bubbles within an air detection tubing region 250 of the first fluid path 17A and the second fluid path 17B. The air detection tubing region 250, for example, may be associated with a proximal portion of the first fluid path 17A and the second fluid path 17B. The at least one air detector 240 may include an ultrasonic sensor, an optical sensor, or the like, configured to detect the one or more air bubbles within the fluid path.

With continued reference to FIG. 3, the injector 100 may further include bulk fluid containers 19A and 19B for filling and refilling the respective syringes 12 with imaging contrast media and flushing fluid, respectively. The bulk fluid containers 19A and 19B may be in selective fluid communication with the syringes 12 via respective bulk fluid paths 21A and 21B and bulk fluid valves 23A and 23B.

Further details and examples of suitable non-limiting powered injector systems, including syringes, controllers, and air detectors, are described in U.S. Pat. Nos. 5,383,858; 7,553,294; 7,666,169; 8,945,051; 10,022,493; and 10,507,319, the disclosures of which are hereby incorporated by reference in their entireties. While the injector 100 is described herein in the context of a dual syringe angiography (CV) injector, it is to be understood that the injector 100 may be adapted for single- and multiple-syringe configurations of any injection procedure (e.g. CT, PET, MRI, ultrasound, etc.)

The injector 100 may include a piston, similar to the piston 13 described herein in FIG. 2, respectively associated with each of the syringes 12. Each piston is configured to drive a respective plunger within a barrel of the respective syringe 12. Due to the high pressures associated with CV angiography, the syringe 12 may be inserted into a pressure jacket 15 to control radial expansion of the syringe. The controller is operatively associated with the pistons to reciprocatively move the plungers within the syringes 12 and thereby execute an injection procedure.

The controller may be programmed or configured to execute a filling operation during which the piston associated with each syringe 12 is withdrawn toward a proximal end of the syringe 12 to draw injection fluid (e.g. imaging contrast media and flushing fluid) into the syringe 12 from the bulk fluid containers 19A, 19B. During such filling operation, the controller may be programmed or configured to selectively actuate the bulk fluid valves 23A and 23B to establish fluid communication between the respective syringes 12 and the bulk fluid containers 19A, 19B via the bulk fluid paths 21A and 21B to control filling of the syringes 12 with the appropriate injection fluid. Upon completion of the filing operation, and optionally a priming operation to remove any air from the syringes 12 (for example by priming any such air back into the bulk fluid containers 19A, 19B or through a priming tube), the controller may be programmed or configured to selectively actuate the bulk fluid valves 21A and 21B to block fluid communication between the respective syringes 12 and the bulk fluid container 19A, 19B via the bulk fluid paths 17A and 17B.

After the filling operation and priming operation, the controller may be programmed or configured to execute a delivery operation during which the piston associated with one or both of the syringes 12 is moved toward a distal end of the syringe 12 to inject injection fluid into the first fluid path 17A and the second fluid path 17B. The controller may be programmed or configured to selectively actuate the fluid valves 23A and 23B to establish fluid communication between the syringes 12 and the patient, via the fluid paths 17A, 17B. According to various embodiments, the first fluid path 17A and the second fluid path 17B may merge at a fluid mixing connector that provides turbulent mixing of the first fluid and the second fluid, such as a fluid mixing connector described in International PCT Application Nos. PCT/US2021/019507 and PCT/US2014/026324, the disclosures of which are incorporated herein by reference.

Figure 4:
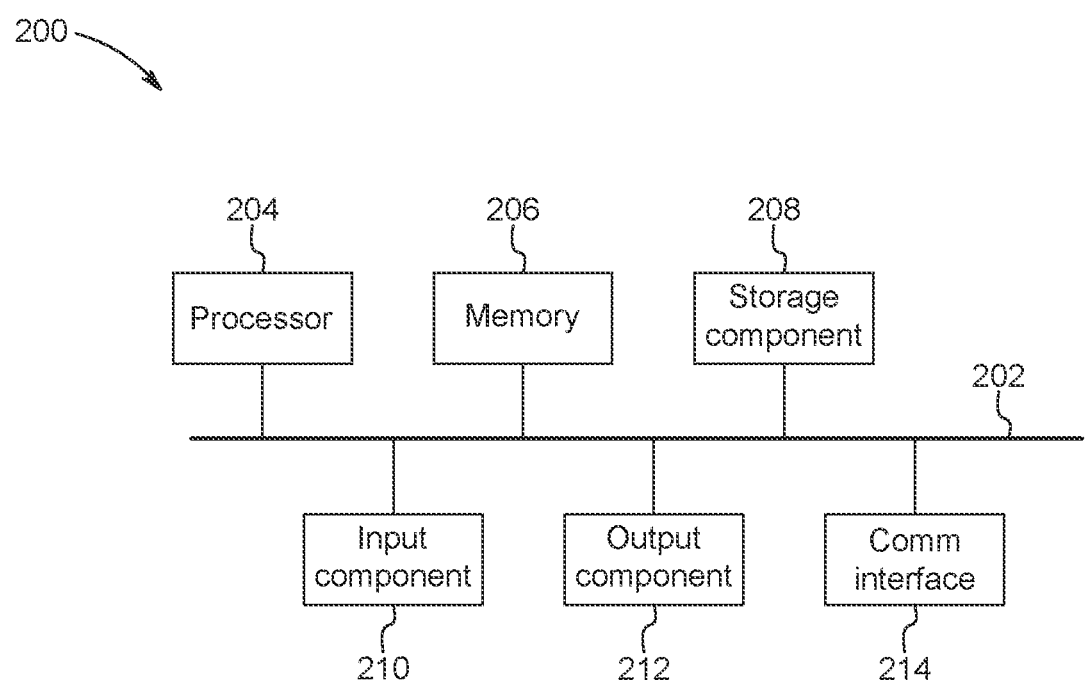
FIG. 4 is a schematic representation of a controller of a fluid injector system according to one embodiment of the present disclosure.

Referring now to FIG. 4, a schematic diagram of example components of an embodiment of controller 200 for implementing and performing the systems and methods described herein is shown according to embodiments of the present disclosure. In some embodiments, the controller 200 may include additional components, fewer components, different components, or differently arranged components than those shown in FIG. 4. The controller 200 may include a bus 202, at least one processor 204, memory 206, a storage component 208, an input component 210 (such as a GUI, keyboard, or other user interface 11, shown in FIG. 3), an output component 212 (such as a GUI or other user interface 11), and a communication interface 214 (such as a GUI or other user interface 11). The bus 202 may include a component that permits communication among the components of the controller 200. In some non-limiting embodiments, the at least one processor 204 may be implemented in hardware, firmware, or a combination of hardware and software. For example, the at least one processor 204 may include a processor (e.g., a central processing unit (CPU), a graphics processing unit (GPU), an accelerated processing unit (APU), etc.), a microprocessor, a digital signal processor (DSP), and/or any processing component (e.g., a field-programmable gate array (FPGA), an application-specific integrated circuit (ASIC), etc.) that can be programmed to perform a function. Memory 206 may include random access memory (RAM), read only memory (ROM), and/or another type of dynamic or static storage device (e.g., flash memory, magnetic memory, optical memory, etc.) that stores information and/or instructions for use by the at least one processor 204.

The storage component 208 may store information and/or software related to the operation and use of the controller 200. For example, the storage component 208 may include a hard disk and/or another type of computer-readable medium. The input component 210 may include a component that permits the controller 200 to receive information, such as via user input (e.g., the GUI, a touch screen display, a keyboard, a keypad, a mouse, a button, a switch, a microphone, etc.). Additionally, or alternatively, the input component 210 may include a sensor for sensing information (e.g., a global positioning system (GPS) component, an accelerometer, a gyroscope, an actuator, etc.). The output component 212 may include a component that provides output information from the controller 200 (e.g., the GUI, a display, a speaker, one or more light-emitting diodes (LEDs), etc.). The communication interface 214 may include a transceiver-like component (e.g., a transceiver, a separate receiver and transmitter, etc.) that enables the controller 200 to communicate with other devices, such as via a wired connection, a wireless connection, or a combination of wired and wireless connections. The communication interface 214 may permit the controller 200 to receive information from another device and/or provide information to another device. The input component 210, output component 212, and/or the communication interface 214 may correspond to, or be components of, the user interface 11 (see FIG. 3).

The controller 200 may perform the method described herein based on the at least one processor 204 executing software instructions stored by a computer-readable medium, such as the memory 206 and/or the storage component 208. A computer-readable medium may include any non-transitory memory device. A memory device includes memory space located inside of a single physical storage device or memory space spread across multiple physical storage devices. Software instructions may be read into the memory 206 and/or the storage component 208 from another computer-readable medium or from another device via communication interface 214. When executed, software instructions stored in the memory 206 and/or storage component 208 may cause processor 204 to perform one or more processes described herein. Additionally, or alternatively, hardwired circuitry may be used in place of or in combination with software instructions to perform one or more processes described herein.

Having described the general structure and function of the injector 10, 100, a non-limiting embodiment of a syringe 300 configured for use with the injector 10 of FIGS. 1-2 or the injector 100 of FIG. 3 will now be discussed in greater detail with reference to FIG. 5A-5B. The syringe 300 generally has a cylindrical syringe barrel 318 formed from glass, metal, or a suitable medical-grade plastic. The barrel 318 has a proximal end 320 and a distal end 324, with a sidewall 319 (shown in FIG. 5B) extending therebetween along a length of a syringe longitudinal axis 315 extending through a center of the barrel 318. The barrel 318 may be made from a transparent or translucent material. A nozzle 322 extends from the distal end 324 of the barrel 318. As shown in FIG. 5B, the barrel 318 has an outer surface 321 and an inner surface 323 that defines an interior volume 325 for receiving the fluid therein. The proximal end 320 of the barrel 318 may be sealed with the plunger 326 that is slidable through the barrel 318. The plunger 326 forms a liquid-tight seal against the inner surface 323 of sidewall 319 of the barrel 318 as the plunger 326 is advanced through the barrel 318. Plunger 326 is configured to releasably engage a piston of fluid injector 10, 100, according to various engagement mechanism as described herein.

A drip flange 335 may extend radially outward from the outer surface 321 of the syringe barrel 318 and prevent fluid that drips from the nozzle 322 from entering the syringe port on the injector. In some embodiments, the drip flange 335 defines a stop surface that delimits the insertion section 330 of the syringe 300.

Figure 5A:
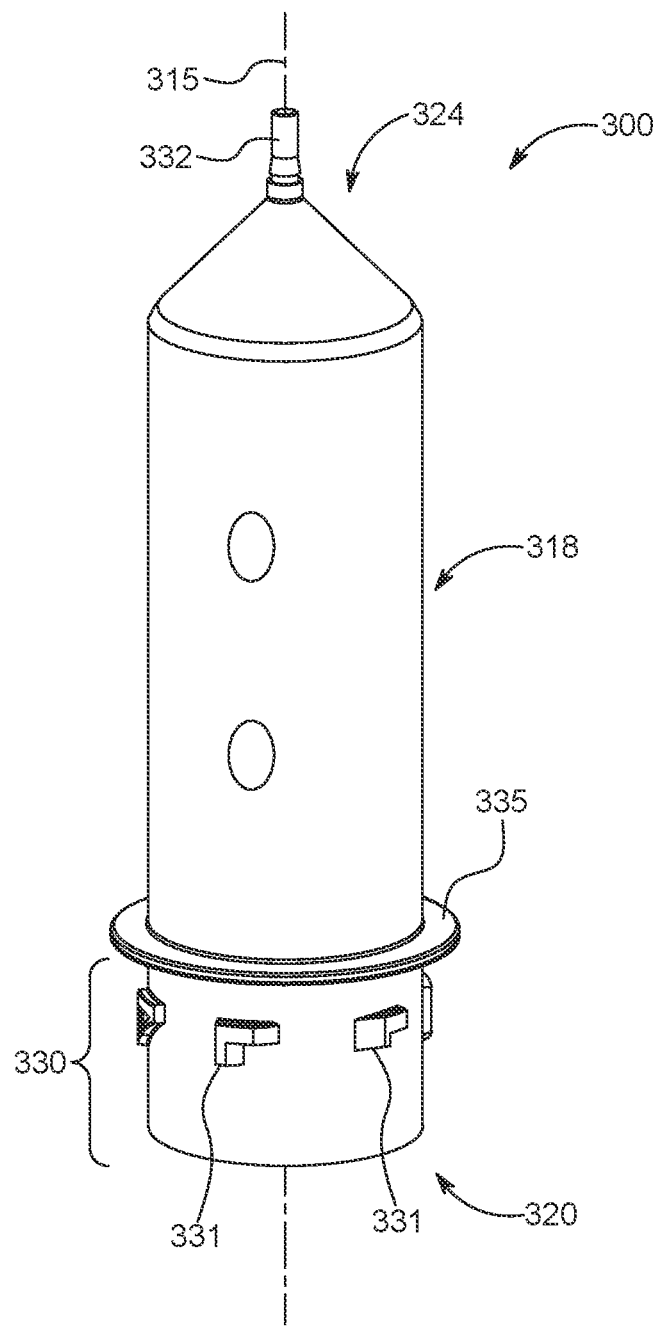
FIG. 5A is a perspective view of a syringe according to one embodiment of the present disclosure.
Figure 5B:
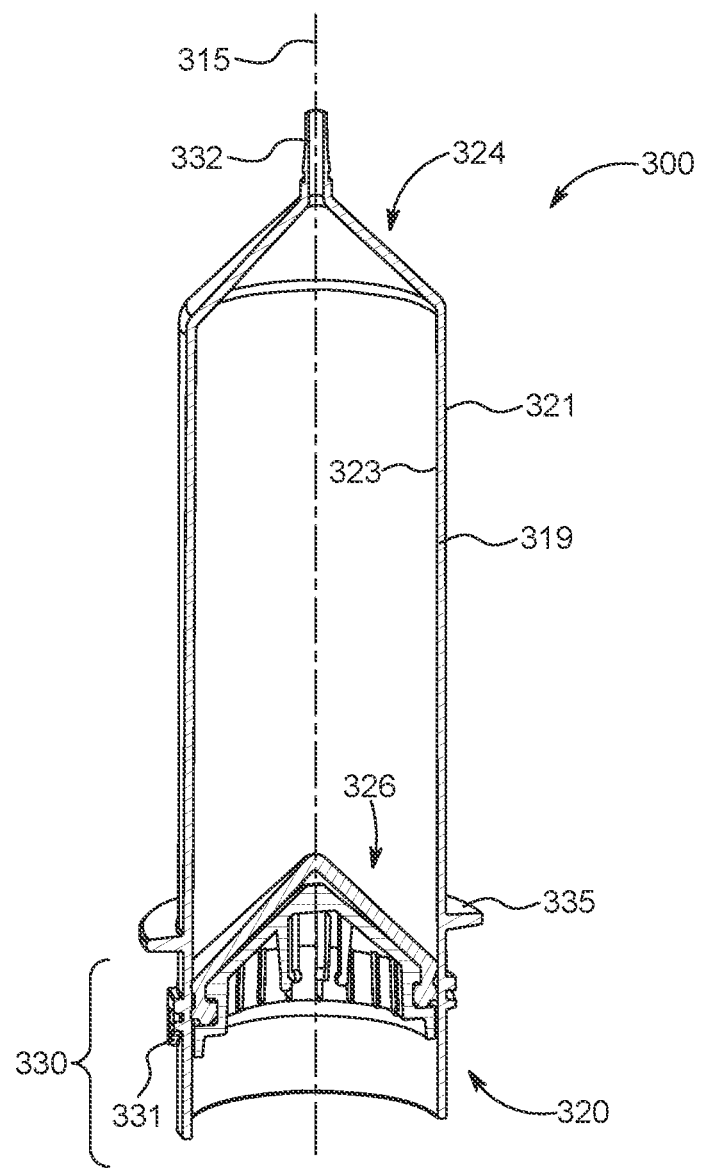
FIG. 5B is a cross-sectional view of the syringe of FIG. 5A showing a plunger positioned within a barrel of the syringe.

With reference to FIG. 5A, in some embodiments, the proximal end 320 of the syringe 300 is sized and adapted for being removably inserted in the syringe port of the injector 10, 100 (shown in FIGS. 1 and 3) or inserted into a pressure jacket (not shown) engaged to a fluid injector. The proximal end 320 of the syringe 300 may define an insertion section 330 that is removably insertable into the syringe port of the injector 10 shown in FIG. 1 or the injector 100 shown in FIG. 3, while the remaining portion of the syringe 300 remains outside of the syringe port. In other embodiments, the syringe 300 may be inserted into a bore of a pressure jacket and releasably retained in the pressure jacket by one or more retention features, for example as described in PCT International Application No. PCT/US2020/049885, the disclosure of which is incorporated herein by this reference. In certain embodiments, the proximal end 320 of the syringe 300 includes one or more syringe retaining members 331 adapted to form a locking engagement with a corresponding locking mechanism in the syringe port of the injector 10, 100 for releasably retaining the syringe 300 in the syringe port. Suitable non-limiting configurations for retaining members for releasably locking the syringe 300 with the injector 10, 100 are described in U.S. Pat. Nos. 9,173,995, and 9,199,033, the disclosures of which are incorporated herein by reference in their entirety. The syringe 300, is omitted from many of the figures of the corresponding plunger engagement mechanisms of the present disclosure for clarity.

With reference to FIGS. 6-8C, the plunger 326 is shown in accordance with one embodiment of the present disclosure. The plunger 326 includes a plunger body 332 defining a plunger longitudinal axis 334 and having a proximal end 336, a distal end 338, and a circumferential sidewall 339 connecting the proximal end 336 and the distal end 338. The sidewall 339 may have a uniform or non-uniform thickness between the proximal end 336 and the distal end 338. At least a portion of the sidewall 339 may be conical. The plunger body 332 may be formed from glass, metal, or a suitable medical-grade plastic.

The plunger body 332 has an interior cavity 340 (FIG. 7) with a conical-shaped portion 342 at the distal end 338 of the plunger body 332 and a cylindrical-shaped portion 344 at the proximal end 336 of the plunger body 332. The conical-shaped portion 342 may be monolithically formed with the cylindrical-shaped portion 344. In some embodiments, the conical-shaped portion 342 may be affixed or otherwise secured to the cylindrical-shaped portion 344 of the plunger body 332 using, for example, a frictional fit and/or an adhesive, welding, or by molding. The conical-shaped portion 342 may have a truncated end 346 having a molded boss 348 configured for engagement with a sensing member, as described herein. In some embodiments, the distal end 338 of the plunger body 332 may be open or enclosed. In some embodiments, the cylindrical-shaped portion 344 may have a ledge 345 that protrudes in a radially-outward direction relative to the longitudinal axis 334. In this manner, ledge 345 partitions the cylindrical-shaped portion 344 into a first portion 347a having a first inner diameter and a second portion 347b having a second inner diameter that is larger than the first inner diameter.

Figure 7:
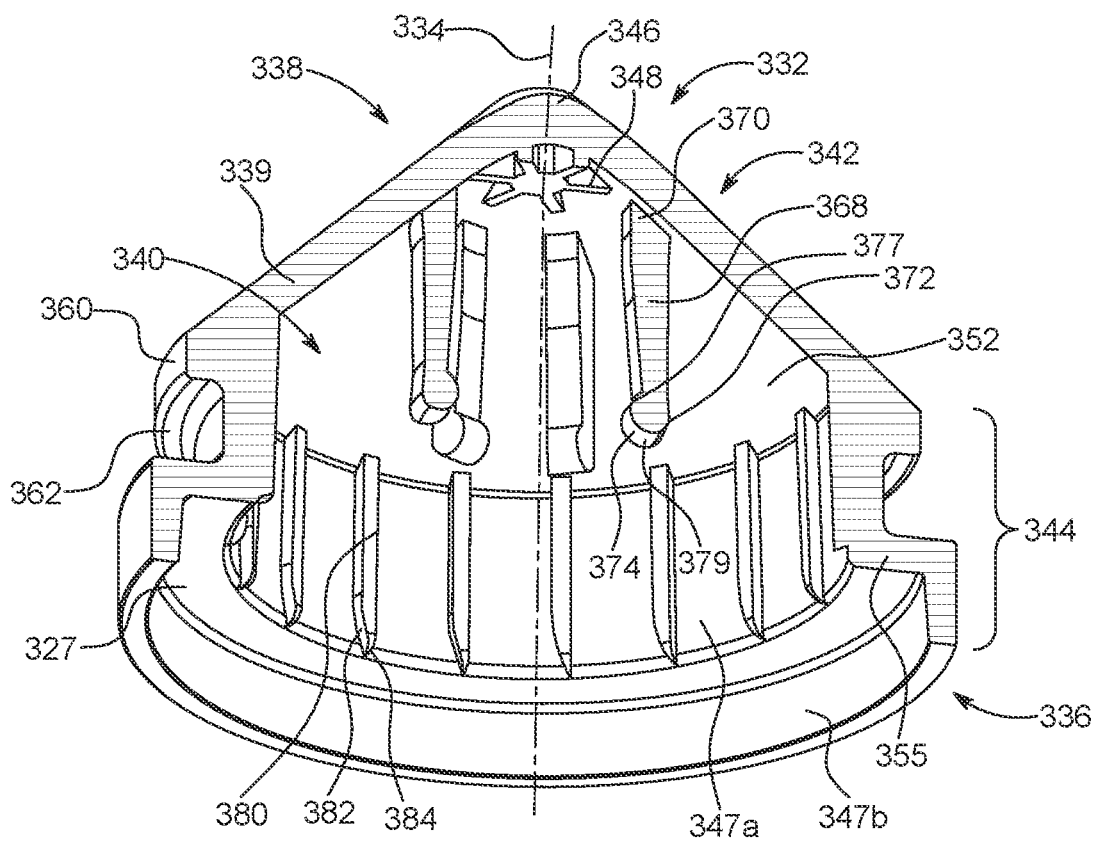
FIG. 7 is a cross-sectional perspective view of a support ring of the plunger of FIG. 6.

With reference to FIG. 7, the plunger 326 may have one or more release tabs 380 protruding from an inner surface 352 of the interior cavity 340 of the plunger body 332. In some embodiments, the one or more release tabs 380 may protrude radially inward from the inner surface 352 of at least a portion of the cylindrical-shaped portion 344 of the plunger body 332, such as the first portion 347a. The one or more release tabs 380 may be configured for interacting with at least a portion of the plunger engagement mechanism on the piston to release the plunger 326 from the piston upon rotation of the plunger 326 about its longitudinal axis 334, such as by rotation of the syringe 300. In some embodiments, a plurality of release tabs 380 may be separated radially relative to the plunger longitudinal axis 334 along a circumference of the inner surface 352 of the interior cavity 340. In such embodiments, the release tabs 380 are separated from each other by portions of the inner surface 352 of the interior cavity 340. In embodiments where more than two release tabs 380 are provided, the release tabs 380 may be evenly spaced apart from each other. In some embodiments, the release tabs 380 may have unequal angular extension and/or unequal angular spacing between the retaining ribs 350 about the inner surface 352 of the interior cavity 340. A proximal end 382 of each release tab 380 may have a pointed or angled guide surface 384 that is configured for orienting the plunger 326 relative to at least a portion of the plunger engagement mechanism, as according to certain embodiments described herein.

Figure 6:
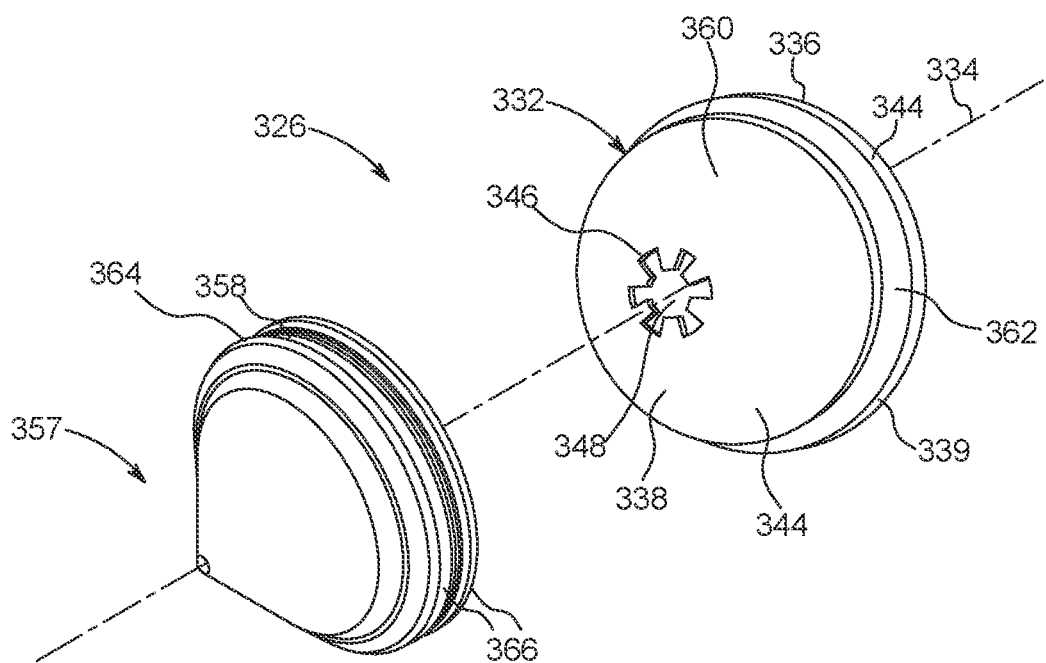
FIG. 6 is an exploded perspective view of a plunger according to one embodiment of the present disclosure.

With reference to FIG. 6, the plunger 326 may have a plunger cover 357 with a resilient seal 358 that covers at least a portion of an outer surface 360 of the plunger body 332. The seal 358 may be a flexible seal that engages an inner surface 323 of the syringe barrel 318 (shown in FIG. 5B) such that the seal 358 seals the interior volume 325 of the syringe barrel 318 in a liquid-tight manner. The seal 358 may be provided separately from the plunger body 332, or it may be integrally formed with the plunger body 332, such as by co-molding. In some embodiments, the outer surface 360 of the plunger body 332 may have a circumferential groove 362. At least a portion of seal 358 may be retained within the circumferential groove 362. The exterior surface 364 of the seal 358 may have one or more lips, projections, or other sealing elements 366 that slidingly engage an inner surface of the syringe barrel 318. In some embodiments, at least the sealing elements 366 of the seal 358 may be made from an elastomeric material that resiliently engages the inner surface 323 of the syringe barrel 18. The at least one extension 356 on the plunger body 332 may prevent the seal 358 from coming out of axial alignment with syringe 300 as plunger 326 is moved through the syringe barrel 318.

With reference to FIG. 7, the plunger 326 may have at least one resiliently deflectable retaining member 368 (hereinafter "retaining member 368") protruding proximally from the plunger body 332. In some embodiments, the at least one retaining member 368 may protrude proximally from an inner surface 352 of the interior cavity 340 of the plunger body 332. The at least one retaining member 368 has a first distal end 370 connected to the plunger body 332 and a second proximal end 372 radially deflectable relative to the first end 370 in a direction toward and/or away from the longitudinal axis 334. As described herein, the second end 372 may be radially deflectable relative to the first end 370 when the at least one retaining member 368 engages at least a portion of a plunger engagement mechanism on a piston of the injector 10, 100 (FIGS. 1 and 3). That is, as the portion of the plunger engagement mechanism is moved in a distal direction and contacts the retaining member 368, the retaining member 368 is radially deflected by the portion of the plunger engagement mechanism. In an analogous manner, during a disengagement operation of the piston from the plunger, as the portion of the plunger engagement mechanism is moved in a proximal direction and contacts the retaining member 368, the retaining member 368 is radially deflected by the portion of the plunger engagement mechanism. The first end 370 and the second end 372 may be spaced apart in a direction that extends substantially along a direction of the plunger longitudinal axis 334 of the plunger 326. The at least one retaining member 368 may be linearly or curvilinearly contiguous between the first end 370 and the second end 372. In some embodiments, one or more retaining members 368 may extend in a direction parallel to a direction of the plunger longitudinal axis 334. In other embodiments, one or more retaining members 368 may extend in a direction that is angled relative to the direction of the plunger longitudinal axis 334. For example, one or more retaining members 368 may be angled toward or away from the plunger longitudinal axis 334 in a direction extending from the proximal end 336 to the distal end 338 of the plunger body 332.

In some embodiments, a plurality of retaining members 368 are spaced apart radially from the plunger longitudinal axis 334 along a circumference of the inner surface 352 of the interior cavity 340. In such embodiments, the retaining members 368 are separated from each other by portions of the inner surface 352 of the interior cavity 340. In embodiments where more than two retaining members 368 are provided, the retaining members 368 may be evenly spaced apart from each other. In one exemplary and non-limiting aspect with six retaining members 368 having equal angular separation therebetween, such as shown in FIGS. 7-8C, for example, each retaining member 368 is separated by 60 degrees from the retaining members 368 adjacent on either side. In some embodiments, the retaining members 368 may have unequal angular extension and/or unequal angular spacing between the retaining members 68 about the inner surface 352 of the interior cavity 340. The radial spacing of the at least one retaining member 368 relative to the plunger longitudinal axis 334 is selected to correspond to an outer circumference of the piston, as described herein.

The second end 372 of the retaining member 368 has at least one catch 374. The at least one catch 374 protrudes radially from the retaining member 368. The at least one catch 374 is configured to interact with the portion of the plunger engagement mechanism to deflect the second end 372 as the portion of the plunger engagement mechanism passes by the at least one catch 372. In some embodiments, the at least one catch 374 may protrude radially inward toward the plunger longitudinal axis 334 of the plunger body 332. In this manner, the at least one retaining member 368 is configured for deflecting in a radially outward direction due to contact between the catch 374 and at least a portion of the plunger engagement mechanism on the piston, as described herein. In some embodiments, the at least one catch 374 may protrude radially outward away the plunger longitudinal axis 334 of the plunger body 332. In this manner, the at least one retaining member 368 is configured for deflecting in a radially inward direction due to contact between the catch 374 and at least a portion of the plunger engagement mechanism on the piston, as described herein. The at least one retaining member 368 is configured to return toward its undeflected state by moving in a radially inward direction.

The at least one catch 374 may be formed integrally with the second end 372 of the at least one retaining member 368 or it may be affixed or otherwise secured to the second end 372 of the at least one retaining member 368 using, for example, a frictional fit and/or an adhesive, welding, or by co-molding. In other embodiments, the at least one catch 374 may be formed on the second end 372 of the at least one retaining member 368 by etching, laser cutting, or machining. As described herein, the at least one catch 374 is shaped to be received within a catch receiving space or groove of a plunger engagement mechanism provided on the piston of the injector 10, 100 to lock the at least one retaining member 368 relative to the piston when the plunger engagement mechanism is in a locked state or position by an embodiment of the mechanisms described herein. As shown in FIGS. 7-8C, the catch 374 may have a distal surface 377 with a rounded edge. In some embodiments, the catch 374 may have a proximal surface 379 with a rounded edge. The shape of the distal surface 377 and the proximal surface 379 may be such that the catch 374 cannot, by itself, form a locking engagement with a corresponding locking feature on the plunger engagement mechanism on the piston. Instead, catch 374 must act with actuation of the plunger engagement mechanism to form a locking engagement with the piston.

Figure 8A:
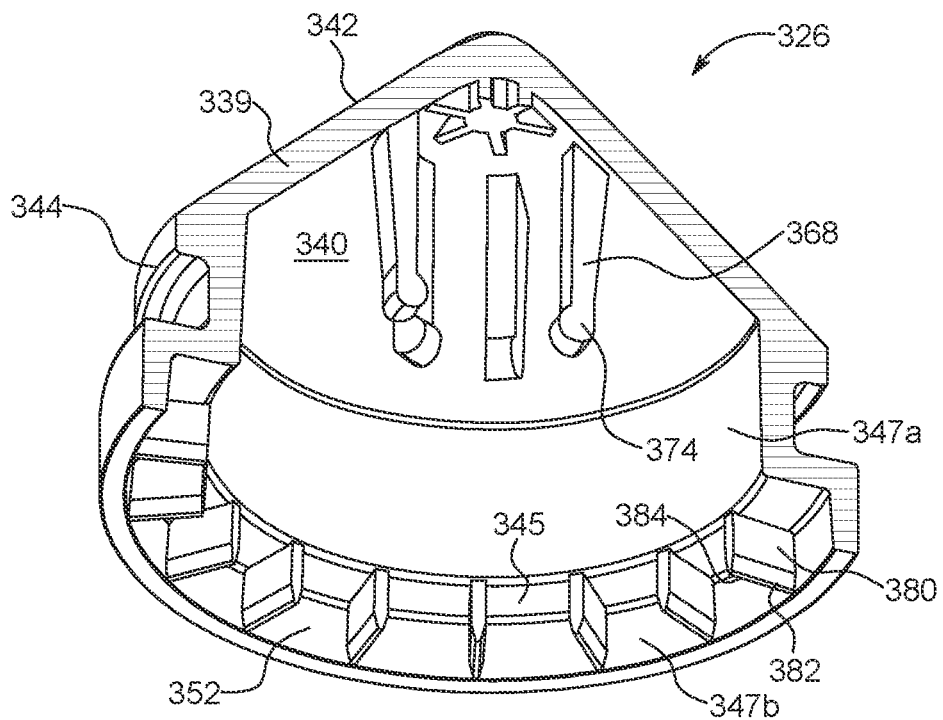
FIG. 8A is a cross-sectional perspective view of a support ring of a plunger according to another embodiment of the present disclosure.
Figure 8B:
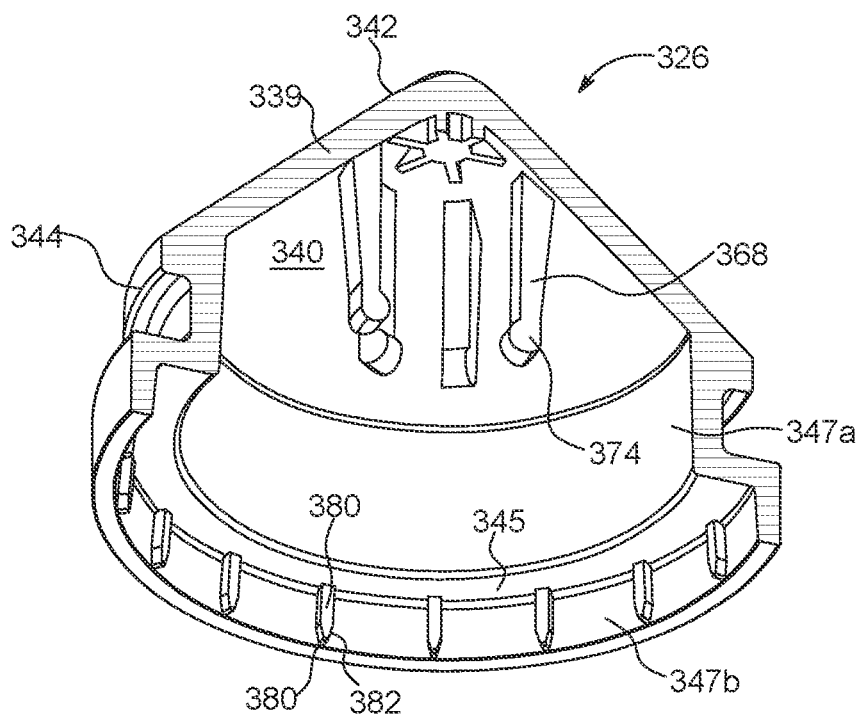
FIG. 8B is a cross-sectional perspective view of a support ring of a plunger according to another embodiment of the present disclosure.
Figure 8C:
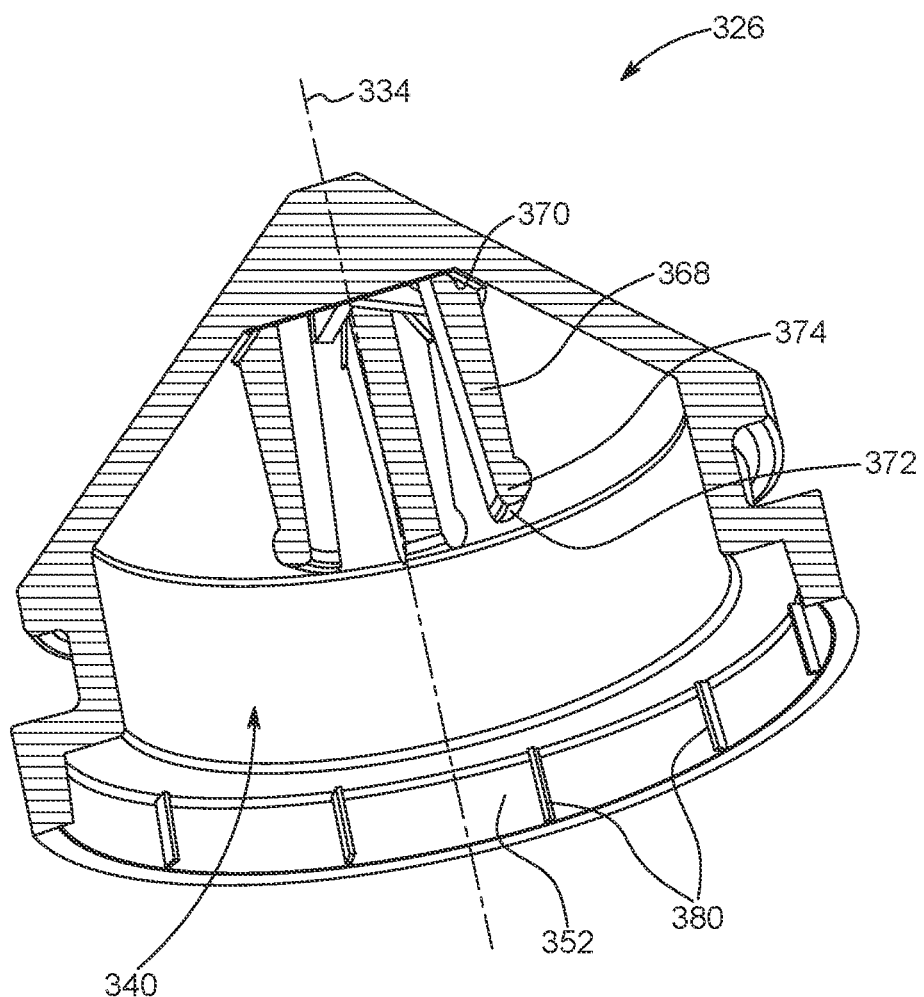
FIG. 8C is a cross-sectional perspective view of a support ring of a plunger according to another embodiment of the present disclosure.

With reference to FIGS. 8A-8C, a plunger 326 is shown in accordance with various embodiments of the present disclosure. The components of the plunger 326 shown in FIGS. 8A-8C are substantially similar or identical to the components of the plunger 326 described herein with reference to FIGS. 6-7. Accordingly, reference numerals in FIGS. 8A-8C are used to illustrate identical components of the corresponding reference numerals in FIGS. 6-7, and only the relative differences between the embodiments of plunger 326 are discussed herein.

With reference to FIGS. 8A-8C, the plunger 326 may have one or more release tabs 380 protruding from the inner surface 352 of at least a portion of the cylindrical-shaped portion 344 of the plunger body 332, such as the second portion 347b. The one or more release tabs 380 may protrude axially from the ledge 345 and radially inward from the inner surface 352 of the second portion 347b of the cylindrical-shaped portion 344 and may protrude radially inward from the inner surface 352 of the second portion 347b along the entire width of the ledge 345 (FIG. 8A) or along a portion of the width of the ledge 345 (FIGS. 8B and 8C). As described herein, the one or more release tabs 380 are configured for interacting with at least a portion of the plunger engagement mechanism on the piston to effect a release of the plunger 326 from the piston upon rotation of the plunger 326 about its longitudinal axis 334, such as due to rotation of the syringe 300.

The embodiment of plunger 326 in FIG. 8C has at least one retaining member 368 with a catch 374 that protrudes radially outward in a direction away from the plunger longitudinal axis 334. In this manner, the at least one retaining member 368 shown in FIG. 8C is configured for deflecting in a radially inward direction due to contact between the catch 374 and at least a portion of the plunger engagement mechanism on the piston, as described herein. The at least one retaining member 368 shown in FIG. 8C is configured to return toward its undeflected state by moving in a radially outward direction.

Figure 9:
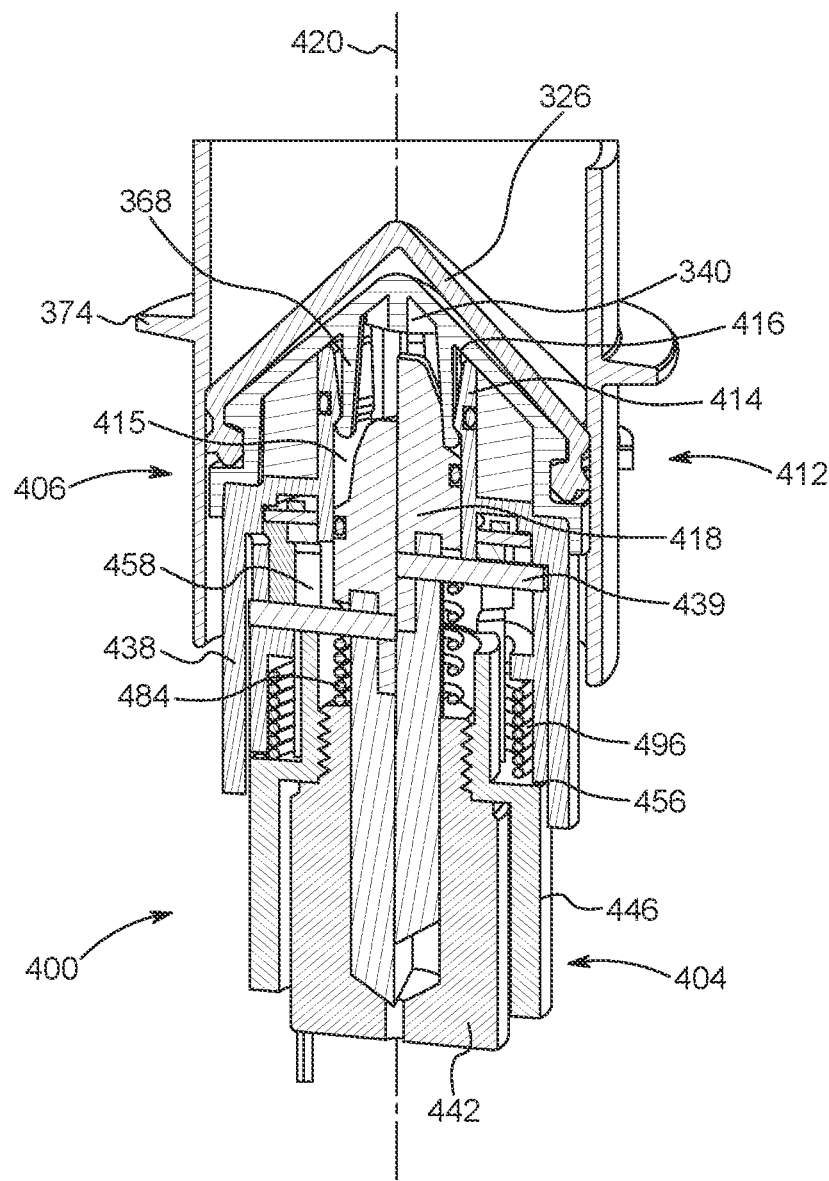
FIG. 9 is a perspective cross-sectional view of a piston of a plunger engagement mechanism according to one embodiment of the present disclosure.

Referring to FIG. 9, an embodiment of piston 400 is shown separate from an injector. In other embodiments, the piston 400 may be configured for use with a fluid injector such as described herein, or any fluid injector configured for medical use. The piston 400 is configured for reciprocal movement within the housing of the injector via a drive mechanism. The drive mechanism may include, for example, an electric motor 402 (shown in FIG. 2), hydraulic system, a pneumatic system, or any combination thereof. The controller 200 (FIG. 2) may be configured for controlling operation of the drive mechanism and, in turn, controlling reciprocal movement of the piston 400. In certain embodiments, the controller 200 may be configured to control engagement and/or disengagement of piston 400 with a plunger.

With continued reference to FIG. 9, the piston 400 has a body 404 and a piston head 406 at a distal end of the body 404. The piston head 406 is configured for removably connecting to a plunger of a syringe, such as the plunger 326 shown in FIG. 8C. The piston head 406 extends radially outwardly beyond the radial edge of the body 404. The piston 400 is constructed from a relatively rigid material, such as metal, plastic, or a combination thereof, that resists deformation. The piston head 406 has a substantially cylindrical structure with a distal end that is configured to be received inside at least a portion of the interior cavity 340 (FIG. 8C) of the plunger 326. In some embodiments, at least a portion of the piston head 406 may be made from a transparent or translucent material that is configured to permit a passage of electromagnetic radiation emitted by one or more electromagnetic radiation sources in the piston 400 for illuminating at least a portion of plunger 326 and/or syringe 300.

In some embodiments, a sensing member, such as a spring-loaded pin (see, e.g., pin 767, FIGS. 21A-21B) connected to a sensor, may be provided. The sensing member may extend along a longitudinal axis of the piston 400 and may protrude through at least a portion of the piston head 406. The sensing member may be operative for sensing contact with a surface, such as a surface 348 of the plunger 326, and control a movement of the piston 400 based on the sensed condition. For example, an initial contact between the sensing member and surface 348 of the plunger 326 may cause the pin to be retracted in a proximal direction such that it makes contact with the sensor. The sensor may be connected to the drive mechanism of the piston 400 such that, upon activation of the sensor by the pin, the sensor controls the movement of the drive mechanism. For example, the drive mechanism may be stopped or slowed from a first rate to a second, slower rate.

In some embodiments, the piston head 406 has a plunger engagement mechanism 412 configured for releasably engaging the plunger 326 to facilitate reciprocally driving the plunger 326 within the barrel of the syringe 300 (FIG. 5A-5B). With continued reference to FIG. 9, the plunger engagement mechanism 412 has a plunger engagement sleeve 414 having a central opening 416 and a plunger engagement post 418 that is reciprocally movable within the central opening 416 of the plunger engagement sleeve 414 along a direction of a longitudinal piston axis 420. The plunger engagement post 418 is reciprocally driven by an actuator 422. The plunger engagement mechanism 412 is operable between an engaged position or state, and a disengaged position or state. In the engaged position or state, the plunger engagement post 418 may be positioned within the plunger engagement sleeve 414 to capture at least one retaining member 368 associated with the plunger 326 in a receiving space 415 between the plunger engagement sleeve 414 and the plunger engagement post 418. Conversely, in the disengaged position or state, the plunger engagement post 418 may be positioned relative to the plunger engagement sleeve 414 to permit removal of the at least one retaining member 368 associated with the plunger 400 from the receiving space 415 between the plunger engagement sleeve 414 and the plunger engagement post 418. FIG. 9 shows portions of the plunger engagement mechanism 412 in the engaged position or state and the disengaged position or state. Specifically, the plunger engagement post 418 in FIG. 9 is shown both in its engaged position or state (right side of cross-section) and in its disengaged position or state (left side of cross-section). During movement of the plunger engagement mechanism 412 from the engaged position or state to the disengaged position or state, the plunger engagement sleeve 414 and/or the plunger engagement post 418 may be linearly and/or rotatably movable relative to the piston 400.

Figure 10A:
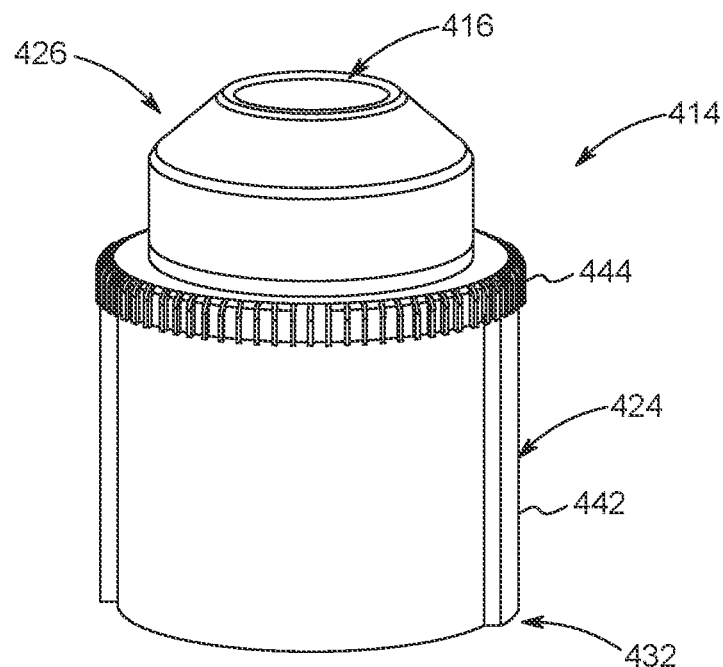
FIG. 10A is a perspective view of a plunger engagement sleeve of the plunger engagement mechanism shown in FIG. 9.
Figure 10B:
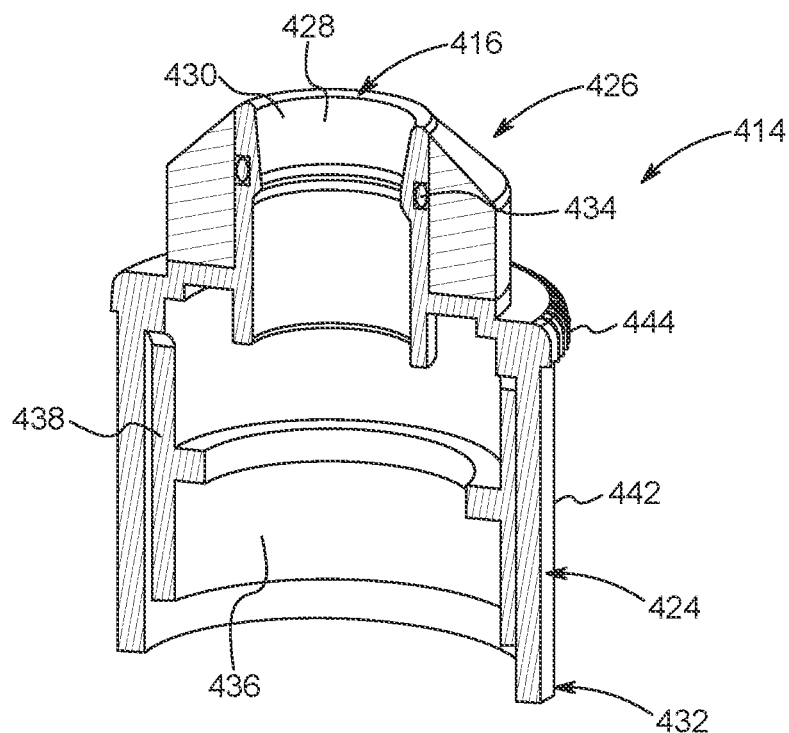
FIG. 10B is a cross-sectional view of the plunger engagement sleeve shown in FIG. 10A.

With reference to FIGS. 10A-10B, the plunger engagement sleeve 414 has a hollow body 424, wherein at least a portion of an outer surface of the hollow body 424 defines at least a portion of the piston head 406 (shown in FIG. 9). A distal portion or end 426 of the plunger engagement sleeve 414 is shaped to be received within the interior cavity 340 of the plunger 326, while at least a portion of the plunger 326, such as the at least one retaining member 368, is configured to be received within the central opening 416 (see, e.g., FIG. 9). The central opening 416 extends through the hollow body 424 of the plunger engagement sleeve 414.

With reference to FIG. 10B, a portion of an inner surface 428 of the central opening 416 at the distal end of the opening 416 may have a ramp 430 such that an inner diameter of the opening 416 narrows in a direction from the distal end 426 of the hollow body 424 toward a proximal portion or end 432. The ramp 430 may be configured for engaging with catch 374 and deflecting the at least one retaining member 426 associated with the plunger 326 in a radially inward direction during connection of the plunger 326 to the distal portion or end 426 of the plunger engagement sleeve 414. The ramp 430 may terminate at a locking rib 434. The at least one catch 374 may flex over and rest against a proximal surface of the locking rib 434 in a manner where at least one catch 374 may readily flex over and move past locking rib 434 if the piston is moved in the proximal direction, unless the plunger engagement mechanism 412 is moved to the locked engagement configuration. That is, the at least one retaining member 426 and corresponding catch 374 may readily flex and move into and out of the central opening 416 of plunger engagement sleeve 414 if the piston is in the disengaged configuration. In some embodiments, the locking rib 434 extends continuously or discontinuously around the inner surface 428 of the hollow body 424 of the plunger engagement sleeve 414 and defines a surface that engages the at least one catch 374 on the at least one retaining member 368 on the plunger 326 to prevent removal of the plunger 326 from the piston 400 when the plunger 326 is in locked engagement with the plunger engagement mechanism 412, as described herein. The inner surface 426 of the central opening 416 may be substantially cylindrical proximally of the locking rib 434.

A proximal portion or end 432 of the hollow body 424 is monolithically formed with the distal portion or end 426 and may have an inner surface 436 with a longitudinal groove 438 configured for receiving a guiding pin 439 of the plunger engagement post 418 (FIG. 9). The longitudinal groove 438 has a distal stop 440 for delimiting a distal movement of the guiding pin 439, and thereby delimiting a distal movement of the plunger engagement post 418 relative to the plunger engagement sleeve 414. An outer surface 442 of the proximal portion or end 432 of the hollow body 424 may have a toothed portion 444 configured for interacting with one or more release tabs 380 on the plunger 326 during removal of the plunger 326 from the plunger engagement mechanism 412.

Figure 11A:
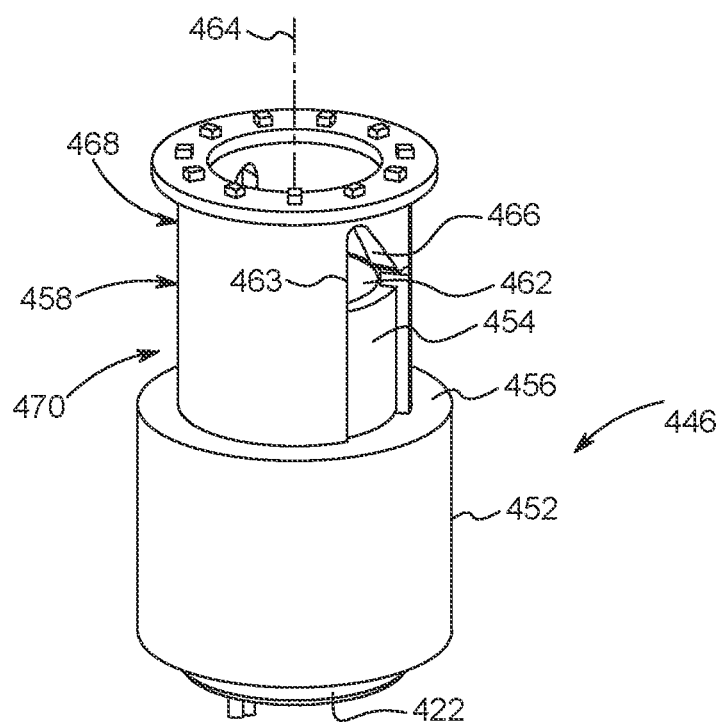
FIG. 11A is a perspective view of an actuator and a plunger release sleeve of the plunger engagement mechanism shown in FIG. 9.
Figure 11B:
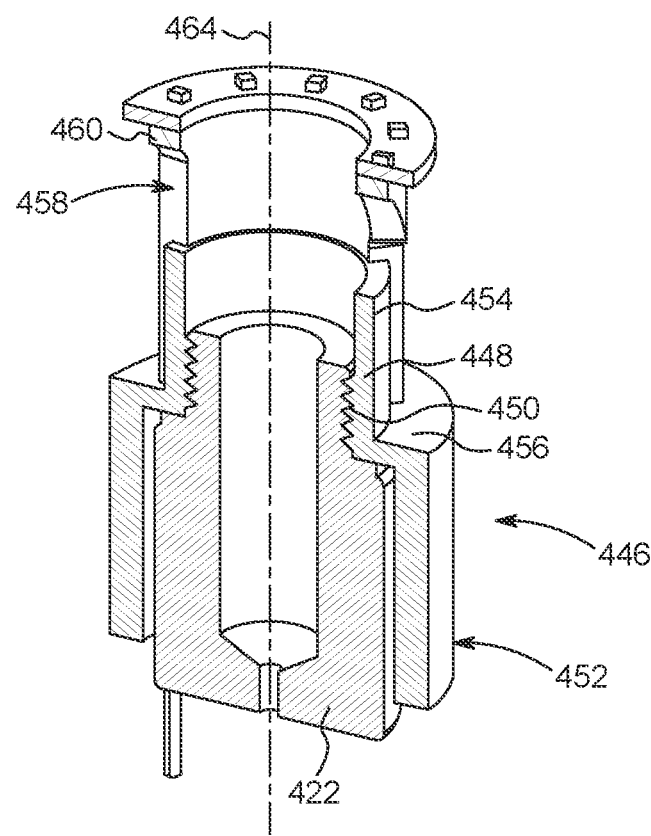
FIG. 11B is a cross-sectional view of the actuator and the plunger release sleeve shown in FIG. 11A.

With reference to FIG. 11A-11B, the plunger engagement mechanism 412 further includes a housing 446 configured for receiving the actuator 422. As shown in FIG. 11B, the housing 446 may have a cylindrical structure having a connection member 448 configured for connecting with a connector 450 on the actuator 422. In some embodiments, the connection member 448 on the housing 446 may be an internally threaded surface that is configured for threadably engaging an externally threaded connector 450 on the actuator 422. In other embodiments, the connection member 448 may be an adhesive, a clip, an interference fit, a fastener, or any other connection feature for removably or non-removably connecting the housing 446 to the connector 450 on the actuator 422.

With reference to FIGS. 11A-11B, the housing 446 has a proximal portion 452 connected to a distal portion 454. In some embodiments, the distal portion 454 may have a smaller outer diameter than the proximal portion 452 such that a ledge 456 is defined at a transition between the proximal portion 452 and the distal portion 454. In some embodiments, the ledge 456 may be configured for supporting a proximal end of a biasing member 496 configured for releasing the plunger 326 from the piston engagement mechanism 412 (FIG. 9) during disengagement of the plunger 326 from the piston 400.

A plunger release sleeve 458 surrounds the distal portion 454 of the housing 446. In some embodiments, the plunger release sleeve 458 has a cylindrical sidewall 460 having an opening 462 extending therethrough. The opening 462 may have a longitudinal surface 463 that is substantially parallel with a longitudinal axis 464 of the plunger release sleeve 458 and a ramped surface 466 that is contiguous with the longitudinal surface 463 and is angled downward relative to the longitudinal axis 464 of the plunger release sleeve 458 in a direction from a distal end 468 toward a proximal end 470. As described herein, the longitudinal surface 463 is configured to guide the guiding pin 439 of the plunger engagement post 418 (FIG. 9) during movement of the plunger engagement post 418 in a longitudinal direction along the longitudinal axis 420 of the piston 400, while the ramped surface 464 is configured to guide the guiding pin 439 during rotational movement of the plunger 326 relative to the piston 400, such as during removal of the plunger 326 from the piston 400. One or more lights 472 may be provided on a printed circuit board 474 connected to the distal end 468 of the plunger release sleeve 458. The one or more lights 472 may be configured for illuminating at least a portion of the plunger 326, as described herein.

With reference to FIG. 11B, the actuator 422 may be configured for having an engaged state for moving one of the plunger engagement sleeve 414 and the plunger engagement post 418 to the engaged position and a disengaged state for moving one of the plunger engagement sleeve and the plunger engagement post to the disengaged position. In some embodiments, the actuator 422 may be automatically moved to the disengaged state, such as during power loss to the actuator 422. In some embodiments, the actuator 422 may be in the engaged state only during proximal movement of the piston 400. In some embodiments, the actuator 422 may be a solenoid configured to be predominantly in the disengaged state and may be in the engaged state only during connection of the plunger 326 to the piston 400. In other embodiments, the actuator 422 may be a rotary electric motor, a linear electric motor, or a linear actuator. In some embodiments, the actuator 422 is a linear actuator that can be back driven manually in the event of a power loss to the injector.

With reference to FIG. 9, the plunger engagement sleeve 414 may be rotatable about the longitudinal piston axis 420 relative to the housing 446 and the plunger release sleeve 458 between a first position and a second position. In some embodiments, the plunger engagement sleeve 414 may be rotatable in a clockwise direction and a counterclockwise direction, or one of the clockwise and a counterclockwise direction. The plunger engagement sleeve 414 may be rotatable from the first position to the second position due to rotational movement of the plunger 326 around the longitudinal piston axis 420. For example, the plunger engagement sleeve 414 may be rotatable around the longitudinal axis 420 due to interaction of the release tabs 390 on the plunger 326 with the toothed portion 444 on the piston engagement sleeve 414. In certain embodiments, rotation of the plunger engagement sleeve 414 may move guiding pin 439 along ramped surface 466 of plunger release sleeve 458 to move plunger engagement post 418 to the disengaged or engaged position. A biasing member 496 may be provided to bias the plunger engagement sleeve 414 to the first position. In this manner, when the plunger engagement sleeve 414 is rotated from the first position toward the second position, the biasing member 496 builds potential energy therein, which is then used to assist in returning the plunger engagement sleeve 414 toward the first position. In some embodiments, the biasing member 496 may be a torsion spring having one end connected to the plunger engagement sleeve 414 and the other end connected to the housing 446 or the plunger release sleeve 458.

Figure 12:
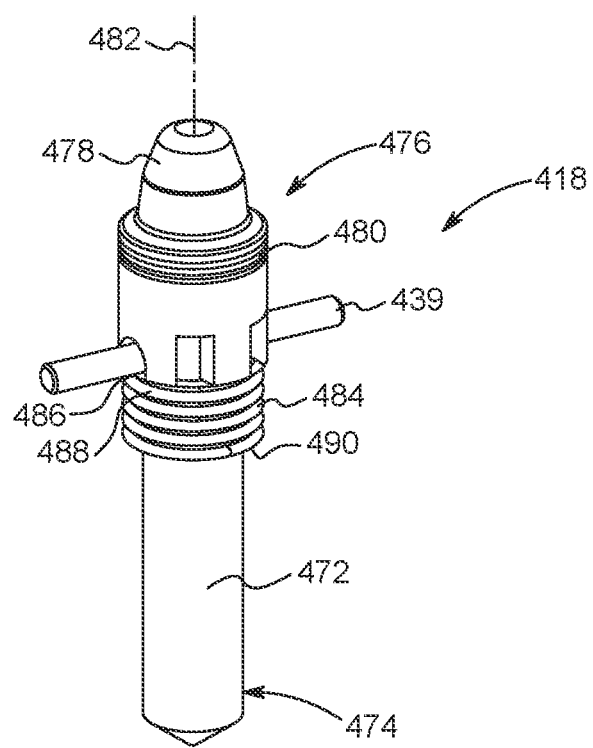
FIG. 12 is a perspective view of a plunger engagement post of the plunger engagement mechanism shown in FIGS. 9 and 13A-13J.

With reference to FIG. 12, the plunger engagement post 418 is shown separate from the plunger engagement mechanism 412. The plunger engagement post 418 has a shaft 472 having a proximal end 474 and a distal end 476. The distal end 476 of the shaft 472 has a tapered end surface 478 configured for contacting the at least one flexible retaining member 368 on the plunger 326 when the plunger engagement post 418 is in an engaged position to lock the at least one catch 374 against the locking rib 434 of the plunger engagement sleeve 414 to prevent removal of the plunger 326 from the piston 400. A seal 480 may be provided at the distal end 478 for sealing against the inner surface 428 of the plunger engagement sleeve 414 (shown in FIGS. 10A-10B). The seal 480 may be an O-ring seal.

The plunger engagement post 418 further includes the guiding pin 439 that is configured for guiding the movement of the plunger engagement post 418 relative to the plunger engagement sleeve 412. In some embodiments, the guiding pin 439 extends through the shaft 472 and is arranged substantially perpendicular to a longitudinal axis 482 of the shaft 472. A resiliently elastic member 484 surrounds the shaft 472 and has a distal end 486 that abuts a ledge 488 on the distal end 478 of the shaft 472. A proximal end 490 of the resiliently elastic member 484 may be configured for contacting the actuator 422 or the housing 446. The resiliently elastic member 484 may be a compression spring that is configured for biasing the plunger engagement post 418 in a distal direction toward the engaged position, as described herein. In other embodiments, the resiliently elastic member 484 may be an extension spring that is configured for biasing the plunger engagement post 418 in a proximal direction toward the disengaged position.

Having described the structure of the plunger 326 and the piston 400 in accordance with one non-limiting embodiment of the present disclosure, a method of engagement and disengagement of the plunger 326 with and from the piston 400 will now be described with reference to FIGS. 13A-13J.

Figure 13A:
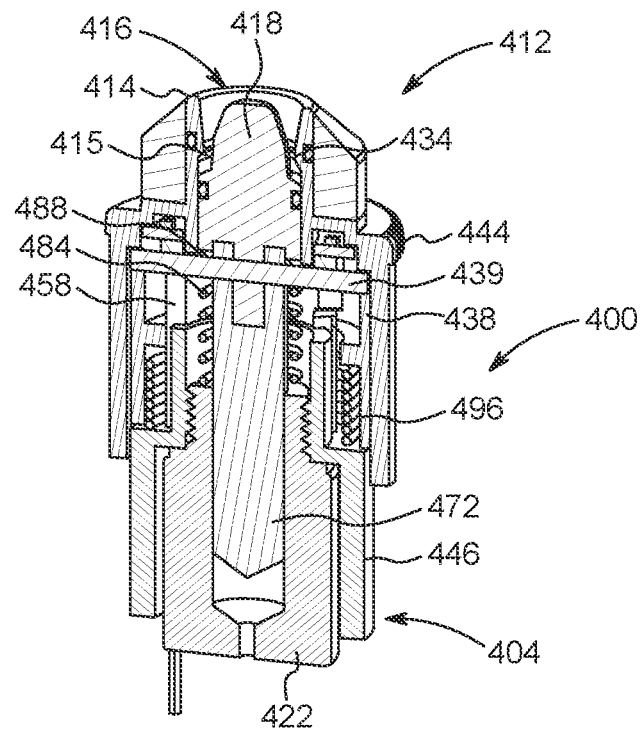
FIGS. 13A-13J are perspective cross-sectional views of the operation of the piston and the plunger engagement mechanism of FIG. 9.

FIG. 13A shows the piston 400 with its plunger engagement mechanism 412 in an engaged position or state and prior to connection with a plunger 326. In some embodiments, the default state of the plunger engagement mechanism 412 may be the engaged position or state. To connect the plunger 326 to the piston 400, the syringe 300 is first connected to the injector 10, 100 (FIGS. 1 and 3). During connection of the syringe 300 to the injector 10, 100, the piston 400 is withdrawn in the housing of the injector 10, 100. After connecting the syringe 300 to injector 10, 100, piston 400 can be advanced in a distal direction toward plunger 326.

Figure 13B:
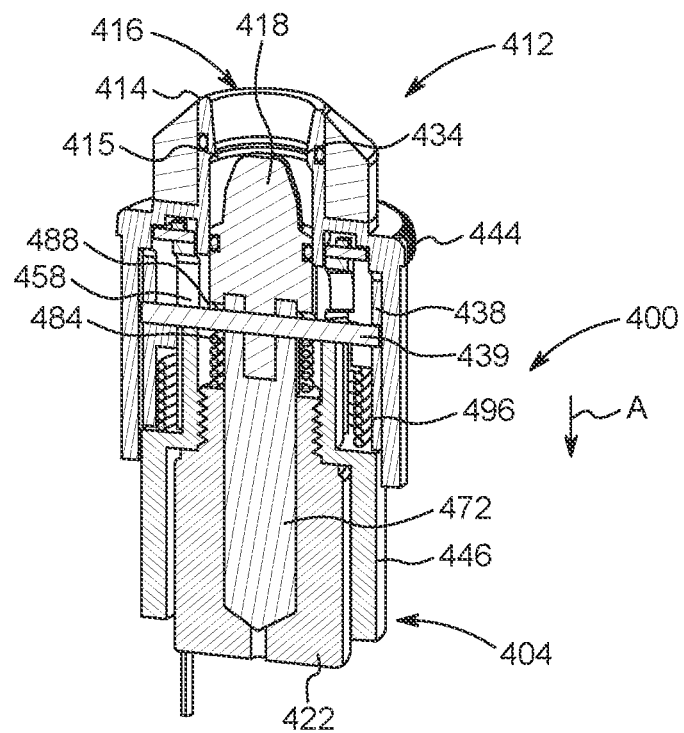

With reference to FIG. 13B, the actuator 422 is energized to retract the shaft 472 of the plunger engagement post 418 in a proximal direction indicated by arrow A from an engaged position or state to a disengaged position or state. Movement of the shaft 472 in the proximal direction opens the receiving space 415 between the plunger engagement sleeve 414 and the plunger engagement post 418 to permit insertion or removal of the one or more retaining members 368 of the plunger 326 into the receiving space 415. Such movement also compresses the resiliently elastic member 484 between the ledge 488 on the distal end of the shaft 472 and the actuator 422. Compression of the resiliently elastic member 484 builds potential energy therein that, when released, can be used to guide the plunger engagement post 418 toward the engaged position or state.

In other embodiments, the actuator 422 may be de-energized, and the shaft 472 of the plunger engagement post 418 may be retracted in a proximal direction indicated by arrow A from an engaged position or state to a disengaged position or state due to an elastic restoring force of the resiliently elastic member 484. In such embodiments, the resiliently elastic member 484 may be an extension spring that is stretched from a first state to a second state due to actuation of the actuator 422. Once the actuator 422 is de-energized, the restoring force in the resiliently elastic member 484 urges the plunger engagement post 418 toward the disengaged position or state. In this manner, the plunger engagement post 418 is in a normally-disengaged position or state, which permits removal of the plunger 326 from the piston 400 in the event that the actuator 422 cannot be operated, such as due to a power loss.

Figure 13C:
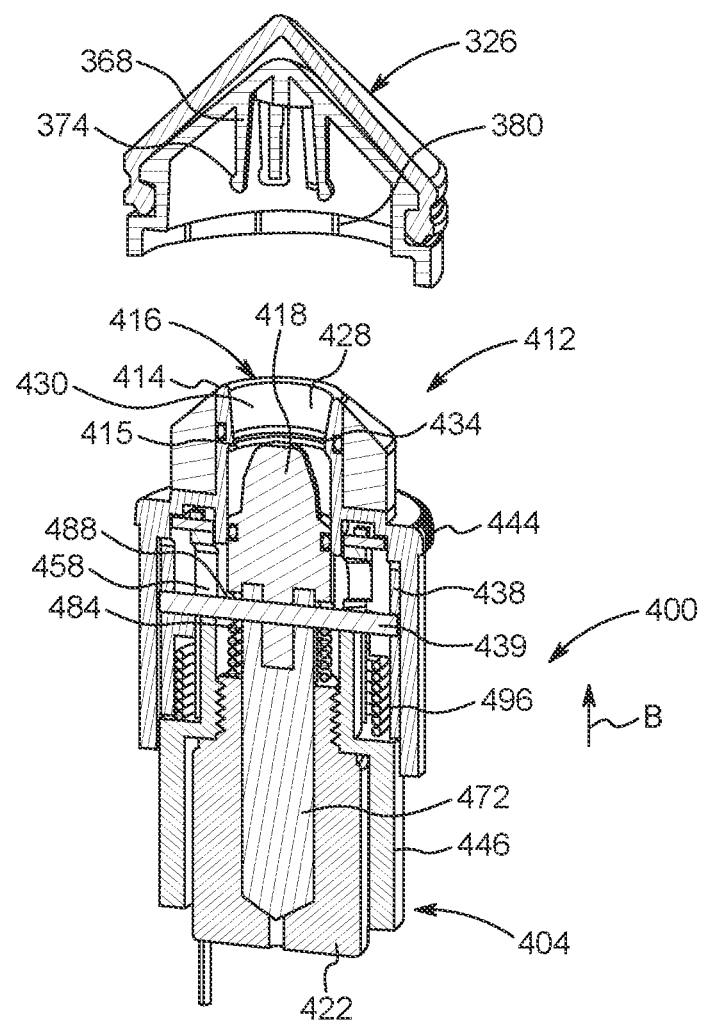

With reference to FIG. 13C, the piston 400 can then be moved axially in a distal direction toward the plunger 326 (indicated by arrow B). In some embodiments, the piston 400 may be advanced distally using the drive mechanism 402 operated by the controller 200 (FIG. 2). In other embodiments, the piston can be manually moved in the distal direction.

Figure 13D:
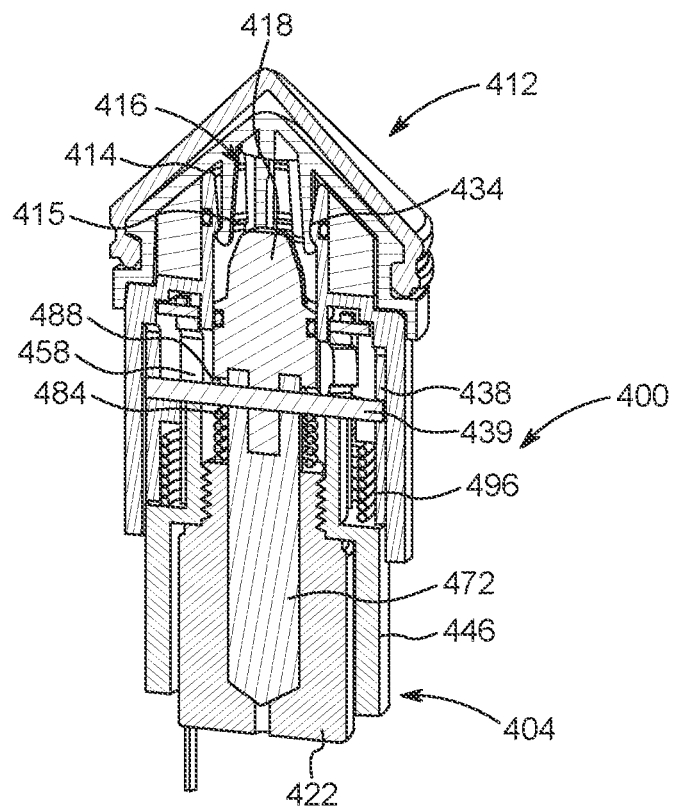

With reference to FIG. 13D, the piston 400 is advanced axially in a distal direction such that the at least one retaining member 368 of the plunger 326 is received within the central opening 416 of the plunger engagement sleeve 414. Initially, the inner surface 428 of the central opening 416 contacts the catch 374 of the at least one retaining member 368. Because the catch 374 protrudes radially outward relative to the at least one retaining member 368, the catch 374 is positioned at a larger radial distance from the plunger longitudinal axis 334 than the ramp 430 of the central opening 416. In this manner, continued distal movement of the piston 400 causes the at least one retaining member 368 to be deflected radially inward due to the contact between the catch 374 and the ramp 430. In embodiments having a plurality of retaining members 368, each of the retaining members 368 is deflected in the radially inward direction.

During continued axial movement of the piston 400 in a distal direction, the catch 374 is deflected over the locking rib 434 of the piston engagement sleeve 414. After the catch 374 is positioned proximally relative to the locking rib 434, distal movement of the piston 400 relative to the plunger 326 is stopped or contact between the distal portion or end 426 of plunger engagement sleeve 414 and the inner surface 352 of the interior cavity 340 of the plunger body 332 causes the plunger 326 to move distally together with piston 400, and the at least one retaining member 368 can elastically deflect in a radially inward direction such that the catch 374 is positioned proximally of the locking rib 434. In some embodiments, distal movement of the piston 400 relative to the plunger 326 may be stopped upon engagement of a portion of the plunger engagement sleeve 414 with the drive shoulder 327 of the plunger 326. While the at least one retaining member 368 is in the position shown in FIG. 13D, the plunger 326 is not in a locked engagement with the piston 400 because the at least one retaining member 368 can be deflected in a radially inward direction with proximal movement of the piston 400 or distal movement of the plunger 326 (such as due to removal of the syringe from the injector). With the plunger 326 connected to the piston 400, the one or more release tabs 380 on the plunger 326 are aligned with the toothed portion 444 on the outer surface 442 of the plunger engagement sleeve 414. In certain embodiments, the plunger 326 may not be in an engaged, locked position with piston 400 when piston 400 is moving in a distal direction and only moves to the engaged, locked position upon proximal movement of the piston 400. Such a feature may allow easy removal of syringe 300 and plunger 326 after a short distal movement of piston 400 and may reduce wear on system components and/or motors by only requiring a locking engagement when the piston 400 is being retracted.

Figure 13E:
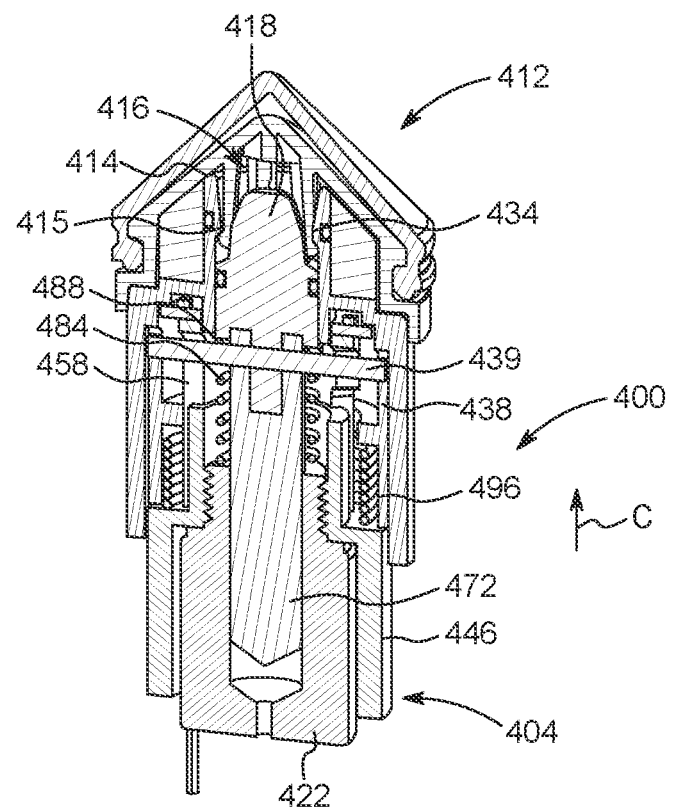
Figure 13F:
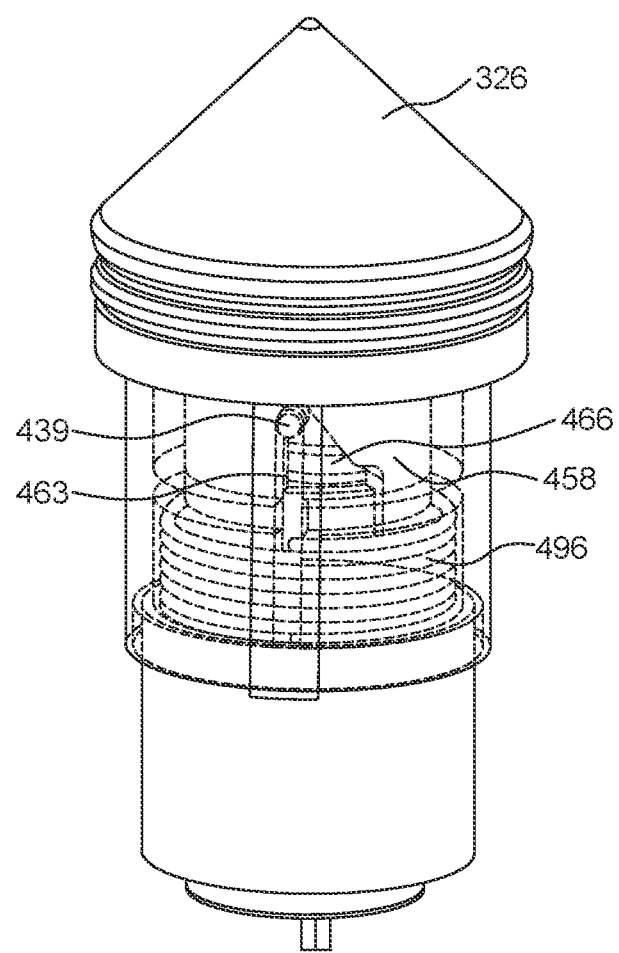

With reference to FIG. 13E, the actuator 422 is de-energized to permit movement of the shaft 472 of the plunger engagement post 418 in a distal direction indicated by arrow C from a disengaged position or state to an engaged position or state. In other embodiments, the actuator 422 may be energized to move the shaft 472 of the plunger engagement post 418 in the distal direction.

Movement of the shaft 472 in the distal direction closes the receiving space 415 between the plunger engagement sleeve 414 and the plunger engagement post 418 locking the at least one catch 374 against the locking rib 434 to prevent removal of the one or more retaining members 368 of the plunger 326 from the receiving space 415, thus preventing removal of the plunger 326 from the piston 400. The plunger engagement post 418 is moved from the disengaged position or state to the engaged position or state due to the release of the potential energy stored in the resiliently elastic member 484. In other embodiments, the plunger engagement post 418 is moved from the disengaged position or state to the engaged position or state due to actuation of the actuator 422, which builds potential energy in the resiliently elastic member 484. Once the plunger engagement post 418 is moved to the engaged position or state, the at least one retaining member 368 of the plunger 326 is captured between the plunger engagement sleeve 414 and the plunger engagement post 418 such that axial movement of the piston 400 results in a corresponding axial movement of the plunger 326 within the syringe barrel. The piston 400 and the connected plunger 326 may then be moved reciprocally within the barrel 318 of the syringe 300 (FIG. 5A-5B). In specific embodiments, when the piston 400 and the connected plunger 326 may be moved proximally within the barrel 318 and may be moved distally when the piston 400 is in either the engaged or disengaged position with the plunger 326. In some embodiments, the piston 400 may be advanced distally to deliver the fluid from the syringe 300 or proximally to fill the syringe 300 with fluid using the drive mechanism 402 operated by the controller 200 (FIG. 2).

In certain embodiments involving manual disengagement of the syringe, to unlock the syringe 300 from the syringe port of the injector and disengage the plunger 326 from the piston 400, the syringe 300 may be rotated clockwise or counter-clockwise about the syringe longitudinal axis, relative to the syringe port. Because the plunger 326 is substantially free from rotation due to frictional interaction against the syringe barrel 318, rotation of the syringe 300 also causes the plunger 326 to rotate relative to the piston 400 about the longitudinal piston axis 420. Due to alignment of the one or more release tabs 380 on the plunger 326 with the toothed portion 444 on the outer surface 442 of the plunger engagement sleeve 414, rotation of the plunger 326 also rotates the plunger engagement sleeve 414 relative to the plunger release sleeve 458 of the plunger engagement mechanism 412 from the first position to the second position. Because the guiding pin 439 on the plunger engagement post 418 is received within a longitudinal groove 438 of the plunger engagement sleeve 414, the plunger engagement post 418 also rotates with rotation of the plunger engagement sleeve 414. Rotation of the plunger engagement post 418 causes the guiding pin 439 to be guided along the ramped surface 466 of the plunger release sleeve 458 (see FIG. 13F) and compress the resiliently elastic member 484. In addition, rotation of the plunger engagement sleeve 414 about the longitudinal piston axis 420 builds potential energy in the biasing member 496.

In other embodiments, such as when the syringe is contained within a pressure jacket, rotation of the syringe and plunger to disengage the plunger 326 from piston 400 may not be possible. According to these embodiments, disengaged and engagement of the piston 400 with the plunger 326 may be accomplished electromechanically, for example by using a motorized or electrical actuator to disengage the plunger 326 from the piston 400. As described herein the motor, such as a linear or rotary electrical motor, or electrical actuator, such as a solenoid, may be used to move the plunger engagement post 418 between the engaged and disengaged positions to engage and disengage the plunger 326 from the piston 400. When the plunger 326 is in the disengaged position, such as at the end of an injection procedure, syringe 300 may be removed from the injector, and the injector may be readied for the next procedure.

Figure 13G:
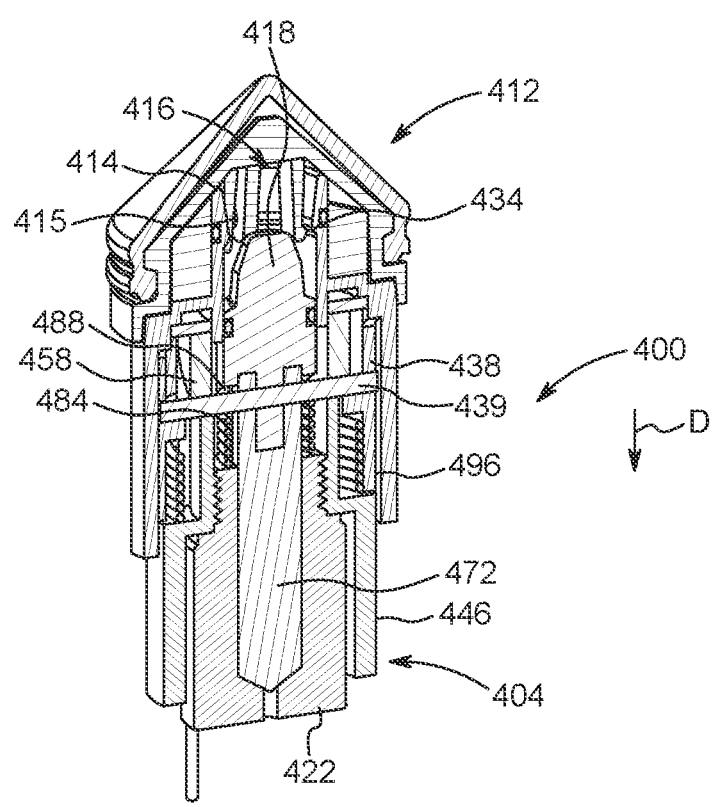

With reference to FIG. 13G, movement of the guiding pin 439 along the ramped surface 466 of the plunger release sleeve 458 causes the plunger engagement post 418 to be moved axially from the engaged position or state to the disengaged position or state in a proximal direction of arrow D. In some embodiments, the piston engagement post 418 can be moved in the proximal direction by energizing the actuator 422 to retract the shaft 472 of the plunger engagement post 418. In this manner, the plunger engagement post 418 can be moved manually, such as via rotation of the plunger 326 relative to the piston 400, or via actuation of the actuator 422. Accordingly, in the event of a power failure, the plunger 326 can be removed from the piston 400. Movement of the plunger engagement post 418 in the proximal direction opens the receiving space 415 between the plunger engagement sleeve 414 and the plunger engagement post 418 to permit removal of the one or more retaining members 368 of plunger 326 from receiving space 415. Further, such a configuration where actuation of actuator 422 is only required for engagement may reduce wear on system components and/or motors by only requiring a locking engagement when piston 400 is being moved in a proximal direction.

Figure 13H:
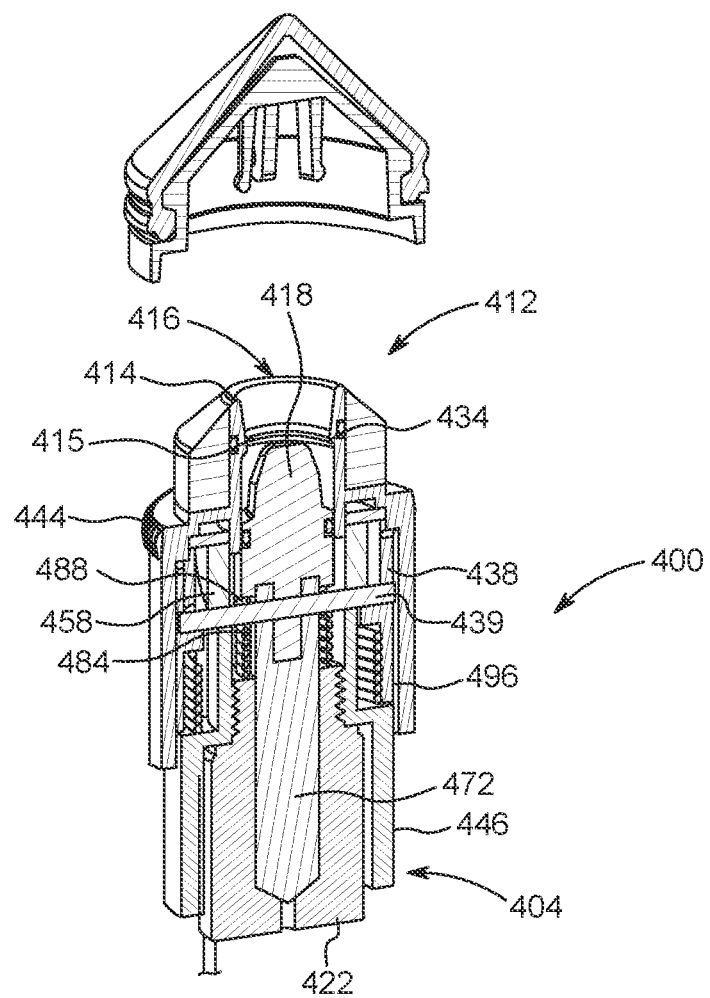

With the plunger engagement mechanism 412 in the disengaged position or state, the syringe 300 can be pulled in the distal direction or the piston 400 can be retracted in the proximal direction to remove the plunger 326 from the piston 400 and to remove the syringe 300 and plunger 326 from the fluid injector. During such relative movement of the piston 326 to the plunger 400 in a direction away from each other, the catch 374 is deflected over the locking rib 434 of the piston engagement sleeve 414 to permit a removal of the one or more retaining members 368 from the piston 400. The plunger 326 can then be freely pulled away from the piston 400, such as shown in FIG. 13H.

Figure 13I:
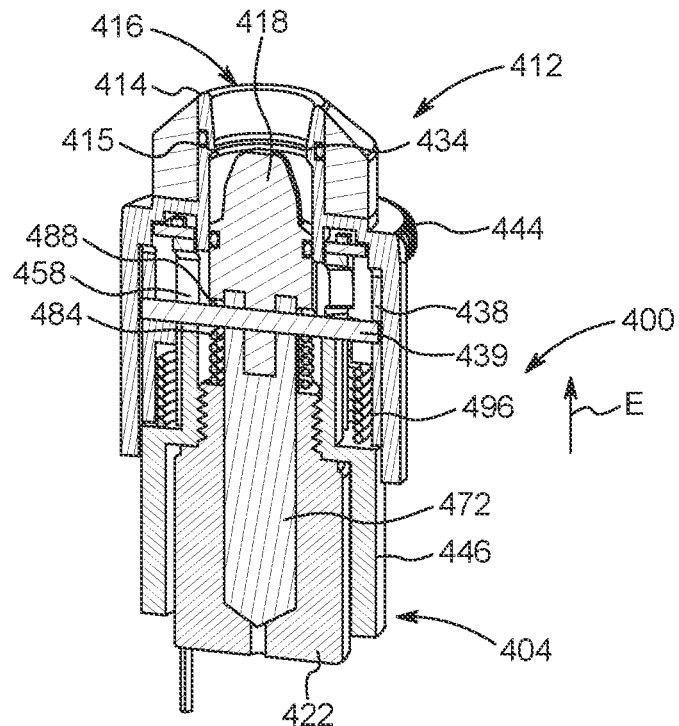
Figure 13J:
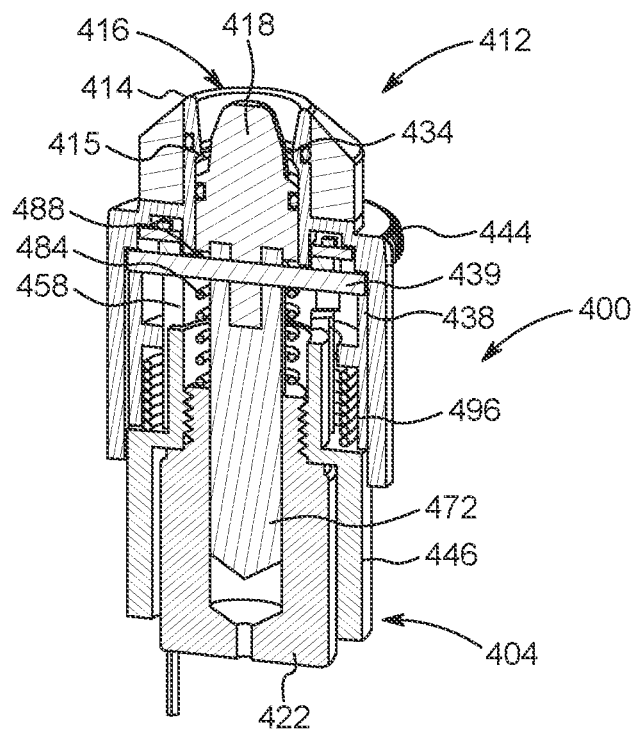

With reference to FIGS. 13I-13J, after the plunger 326 is removed from the piston 400, the plunger engagement sleeve 414 and the plunger engagement post 418 are automatically rotated about the longitudinal piston axis 420 (shown in FIG. 9) from the second position to the first position due to the restoring force provided by the biasing member 496. With movement of the plunger engagement sleeve 414 and the plunger engagement post 418 to the first position, the guiding pin 429 is guided along the ramped surface 466 of the plunger release sleeve 458 toward a distal end of the plunger release sleeve 458 due to the restoring force provided by the resiliently elastic member 484. This causes the plunger engagement post 418 to move in a distal direction of arrow E. The position of the plunger engagement mechanism 412 in FIG. 13J is identical to the position of the plunger engagement mechanism 412 in FIG. 13A.

Figure 14A:
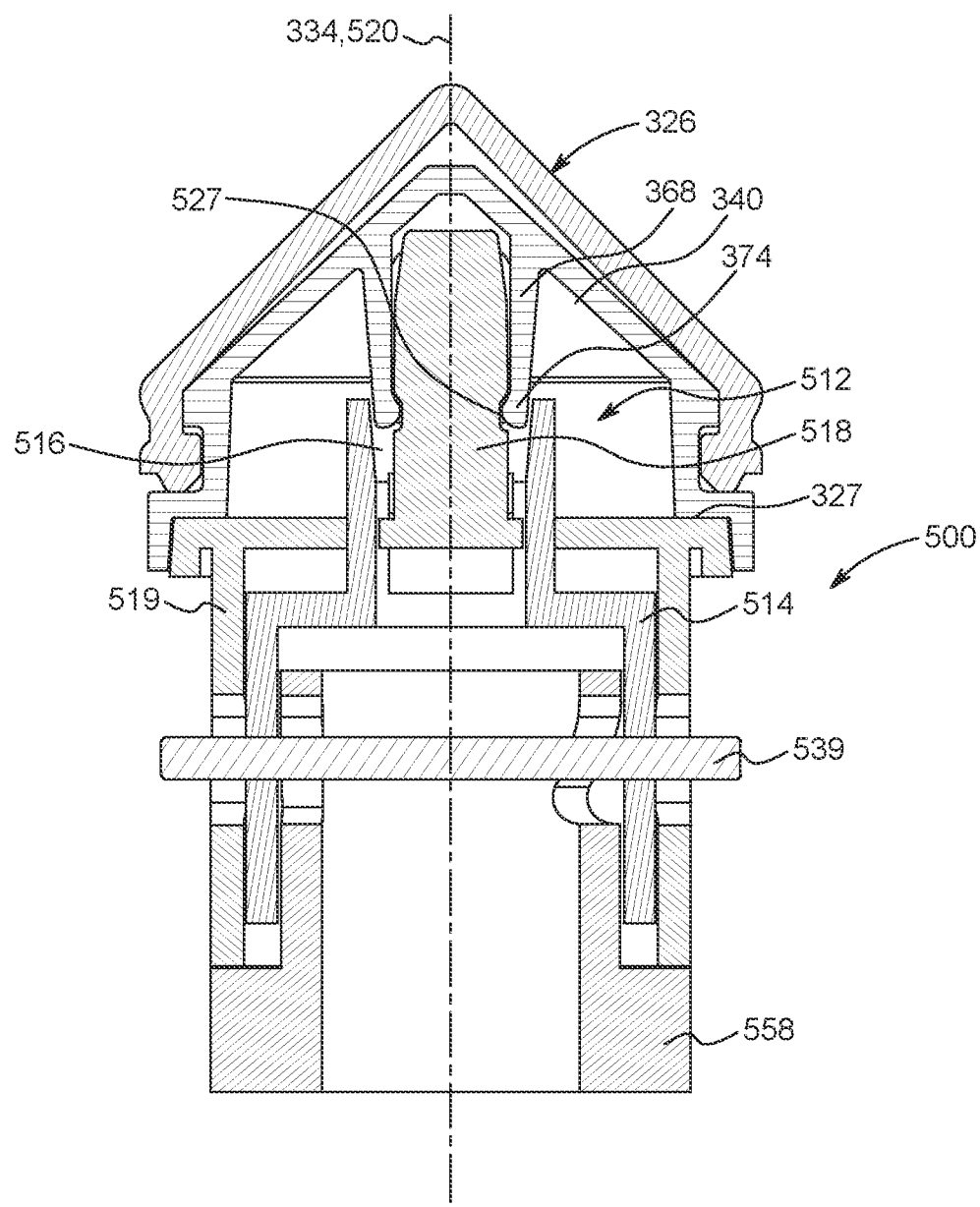
FIGS. 14A-14C are cross-sectional views of the operation of a piston of a plunger engagement mechanism according to another embodiment of the present disclosure.
Figure 14B:
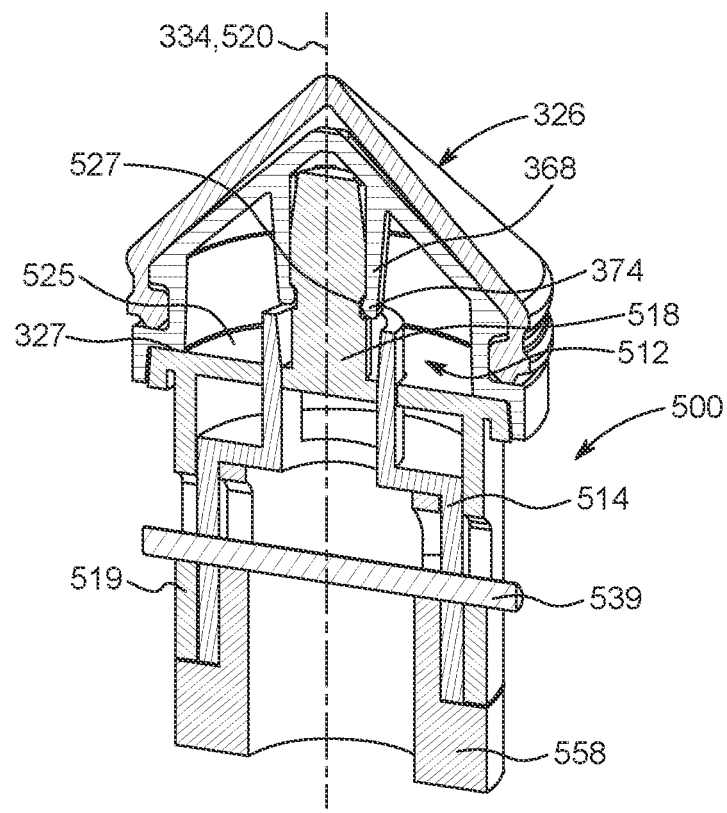
Figure 14C:
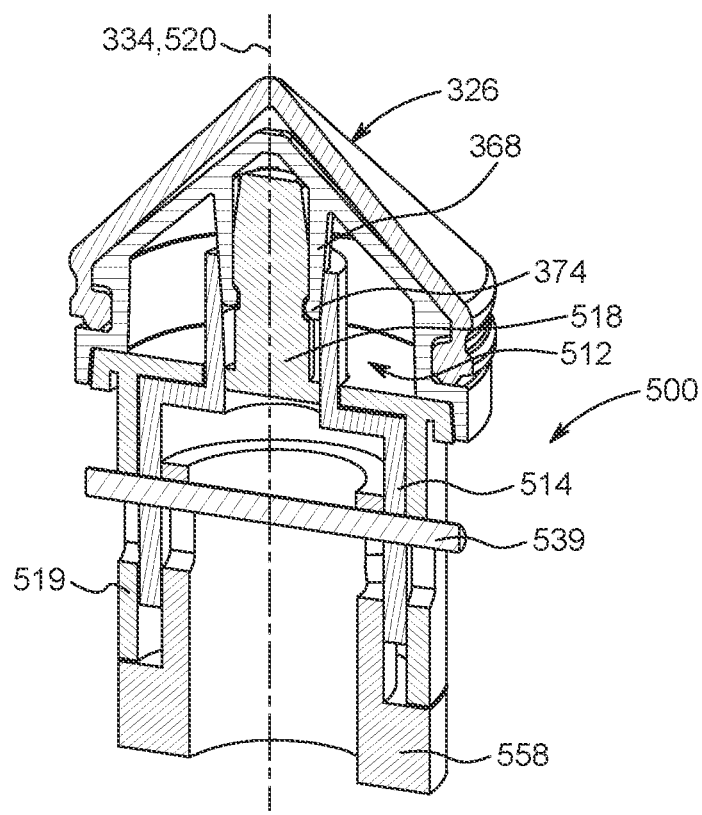

With reference to FIGS. 14A-14C, a piston 500 and a plunger engagement mechanism 512 are shown in accordance with another embodiment of the present disclosure. The components of the piston 500 and the plunger engagement mechanism 512 shown in FIGS. 14A-14C are substantially similar or identical to the components of the piston 400 and the plunger engagement mechanism 412 described herein with reference to FIGS. 9-13J. Accordingly, reference numerals in FIGS. 14A-14C are used to illustrate identical components of the corresponding reference numerals in FIGS. 9-13J, with the exception that the leading number in reference numbers used in FIGS. 14A-14C has been changed from a "4" to a "5". For example, whereas a piston described in connection with FIGS. 9-13J is designated by a reference number "400", the piston in FIGS. 14A-14C is identified by reference number "500". As the previous discussion regarding the piston 400 and the plunger engagement mechanism 412 generally shown in FIGS. 9-13J is applicable to the piston 500 and the plunger engagement mechanism 512 shown in FIGS. 14A-14C, only the relative differences between the components shown in these figures are discussed hereinafter.

Whereas the piston 400 and the plunger engagement mechanism 412 shown in FIGS. 9-13J are configured to interact with a plunger 326 shown in FIGS. 6-8B, the piston 500 and the plunger engagement mechanism 512 of FIGS. 14A-14C are configured for interacting with the plunger 326 of FIG. 8C. In this manner, the at least one retaining member 368 shown in FIGS. 6-8B is configured for deflecting in a radially outward direction due to contact between the catch 374 and at least a portion of the plunger engagement mechanism 518 on the piston, as described herein. The at least one retaining member 368 shown in FIGS. 6-8B is configured to return toward its undeflected state by moving in a radially inward direction.

Figure 15:
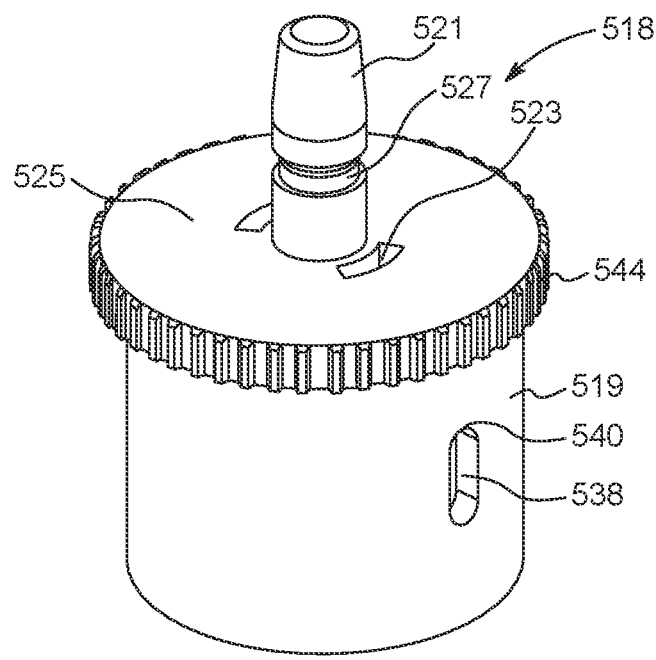
FIG. 15 is a perspective view of a plunger engagement post of a plunger engagement mechanism shown in FIGS. 14A-14C.

With continued reference to FIG. 14A, the plunger engagement mechanism 512 has a plunger engagement sleeve 514 having a central opening 516 and a plunger engagement post 518. The plunger engagement post 518 has a proximal portion 519 that is rotatably connected to the plunger release sleeve 558 such that the plunger engagement post 518 is rotatable about the longitudinal piston axis 520. With reference to FIG. 15, the proximal portion 519 may have a toothed portion 544 at its distal end. As with the toothed portion 444 of the plunger engagement mechanism 412 described herein with reference to FIGS. 9-13J, the toothed portion 544 is configured for interacting with the release tabs 380 on the plunger 326 (FIGS. 8A, 8B, and 14A). The plunger engagement post 518 further has a post portion 521 that extends distally from the proximal portion 519. In some embodiments, the proximal portion 519 and the post portion 521 may be monolithically formed to constitute a unitary part. One or more openings 523 may be formed in the plunger engagement post 518 through a connecting piece 525 connecting the proximal portion 519 to the post portion 521. The opening 523 may be configured to receive a portion of the plunger engagement sleeve 514 therethrough. An upper surface of the connecting piece 525 defines an engagement surface for contacting at least a portion of the plunger 326, such as a drive shoulder 327 of the plunger 326. The plunger engagement post 518 further has a longitudinal groove 538 configured for receiving the guiding pin 539. The longitudinal groove 538 has a distal stop 540 for delimiting a distal movement of the guiding pin 539, and thereby delimiting a distal movement of the plunger engagement sleeve 514 relative to the plunger engagement post 518.

The plunger engagement post 518 in FIGS. 14A-14C is only rotatable about the piston longitudinal axis 520. The plunger engagement post 518 may be rotatable about the longitudinal piston axis 520 and the plunger release sleeve 558 between a first position and a second position. In some embodiments, the plunger engagement post 518 may be rotatable in a clockwise direction and a counterclockwise direction, or one of the clockwise direction and a counterclockwise direction. The plunger engagement post 518 may be rotatable from the first position to the second position due to rotational movement of the plunger 326 around the longitudinal piston axis 520. For example, the plunger engagement post 518 may be rotatable around the longitudinal axis 520 due to interaction of the release tabs 390 on the plunger 326 with the toothed portion 544 on the piston engagement post 518. A biasing member (not shown), similar to the biasing member 496 shown in FIG. 9, may be provided to bias the plunger engagement post 518 to the first position. In this manner, when the plunger engagement post 518 is rotated from the first position toward the second position, the biasing member builds potential energy therein, which is then used to assist in returning the plunger engagement post 518 toward the first position. In some embodiments, the biasing member may be a torsion spring having one end connected to the plunger engagement post 518 and the other end connected to the plunger release sleeve 558.

With continued reference to FIG. 15, the post portion 521 of the plunger engagement post 518 has a locking groove 527 that is configured to receive the catch 374 of the at least one flexible retaining member 368 of the plunger 326. The distal end of post portion 521 may be shaped to deflect the at least one retaining member 368 in a radially outward direction due to contact of the catch 374 with an outer surface of the post portion 521. In certain embodiments, the distal end of post portion 521 may include a ramp to further deflect the at least one retaining member 368 in a radially outward direction. In this manner, distal movement of the piston 500 relative to the plunger 326 causes the at least one retaining member 368 to be deflected radially outward due to the contact between the catch 374 and the outer surface of the post portion 521. In embodiments having a plurality of retaining members 368, each of the retaining members 368 is deflected in the radially outward direction.

Figure 16:
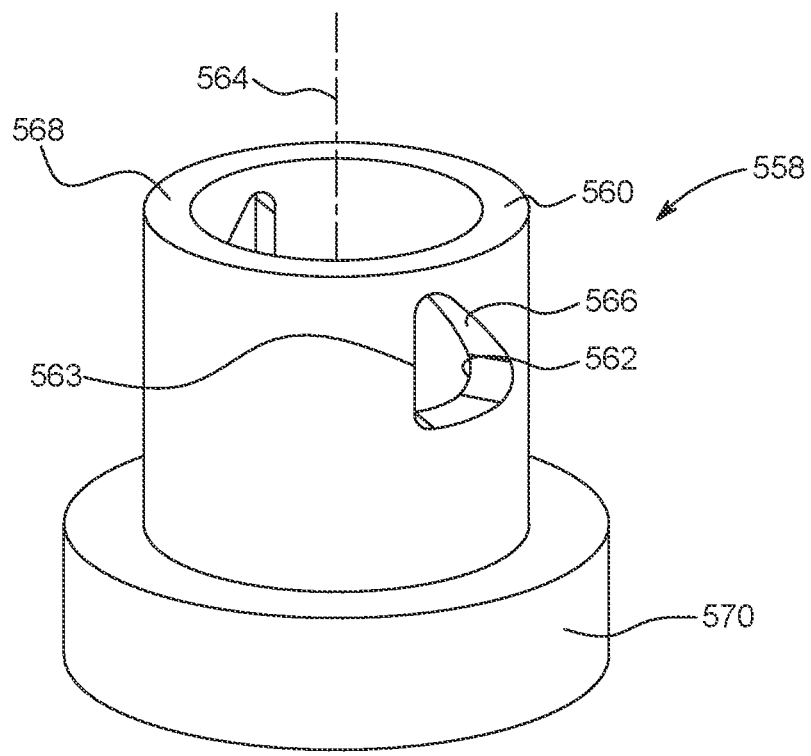
FIG. 16 is a perspective view of a plunger release sleeve of a plunger engagement mechanism shown in FIGS. 14A-14C.

With reference to FIG. 14A, a plunger release sleeve 558 is at least partially received within hollow body structures of the plunger engagement sleeve 514 and the plunger engagement post 518. With reference to FIG. 16, the plunger release sleeve 558 has a cylindrical sidewall 560 having an opening 562 extending therethrough. The opening 562 may have a longitudinal surface 563 that is substantially parallel with a longitudinal axis 564 of the plunger release sleeve 558 and a ramped surface 566 that is contiguous with the longitudinal surface 563 and is angled downward relative to the longitudinal axis 564 of the plunger release sleeve 558 in a direction from a distal end 568 toward a proximal end 570. As described herein, the longitudinal surface 563 is configured to guide the guiding pin 539 (FIG. 14A) during movement of the plunger engagement sleeve 514 in a longitudinal direction along the longitudinal axis 520 of the piston 500, while the ramped surface 564 is configured to guide the guiding pin 539 during rotational movement of the plunger 326 relative to the piston 500 (or vice versa), such as during removal of the plunger 326 from the piston 500.

Figure 17A:
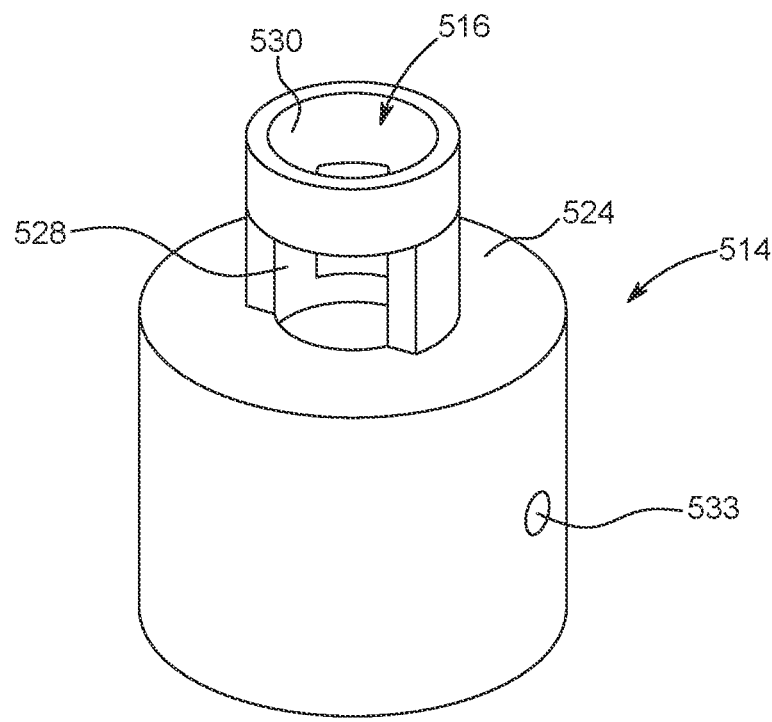
FIGS. 17A and 17B is a perspective view (FIG. 17A) and perspective cross-sectional view (FIG. 17B) of a plunger engagement sleeve of a plunger engagement mechanism shown in FIGS. 14A-14C.
Figure 17B:
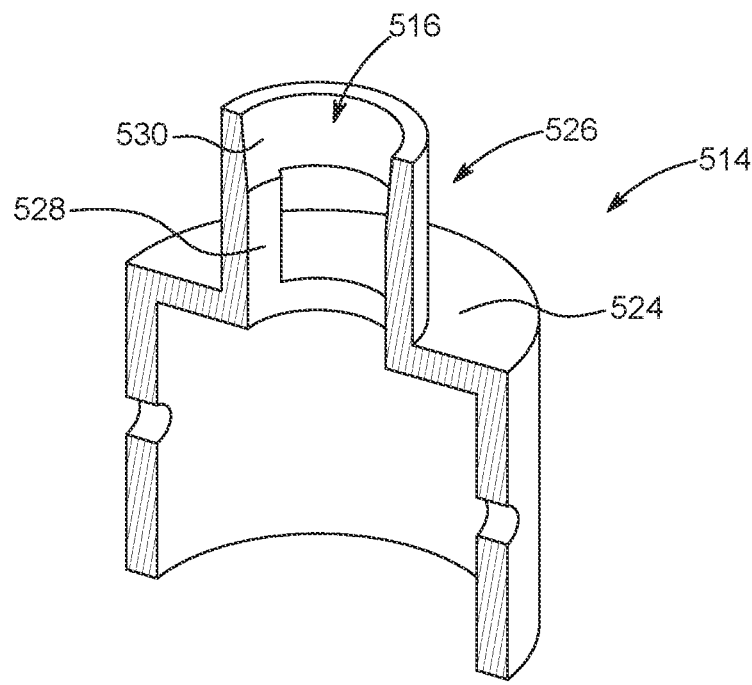

With reference to FIGS. 17A-17B, the plunger engagement sleeve 514 is shown separate from the rest of the plunger engagement mechanism 512. The plunger engagement sleeve 514 has a hollow body 524, at least a portion of which is configured to be received within the proximal portion 519 of the plunger engagement post 518. A distal portion or end 526 of the plunger engagement sleeve 514 is shaped to be received through the opening 523 on the plunger engagement post 518 (FIG. 15) and positioned within the interior cavity 340 of the plunger 326 (FIG. 14A-14B). At least a portion of the plunger 326, such as the at least one retaining member 368, is configured to be received within the central opening 516 and in the receiving space 515 between the post portion 521 of the plunger engagement post 518 and the distal portion or end 526 of the plunger engagement sleeve 514. A portion of an inner surface 528 of the central opening 516 may have a ramp 530 such that an inner diameter of the opening 516 narrows in a direction from the distal end 526 of the hollow body toward a proximal portion or end 532. The ramp 530 may be configured for deflecting the at least one retaining member 368 associated with the plunger 326 in a radially inward direction during connection of the plunger 326 to the piston 500 and creating a tight engaging interaction between the catch 374 of the at least one flexible retaining member 368 and the locking groove 527 of the plunger engagement post 518.

With continued reference to FIGS. 17A-17B, the hollow body 524 of the plunger engagement sleeve 514 has a through hole 533 configured for receiving the guiding pin 539 therethrough. The plunger engagement sleeve 514 is configured to be rotated about its longitudinal axis 531 due to engagement between guiding pin 539 with ramped surface 566 of the plunger release sleeve 558 due to the rotation of the plunger 326 and the plunger engagement post 518.

Having described the structure of the plunger 326 and the piston 500 in accordance with one non-limiting embodiment of the present disclosure, a method of engagement and disengagement of the plunger 326 with and from the piston 500 will now be described with reference to FIGS. 14A-14C.

FIG. 14B shows the piston 500 with its plunger engagement mechanism 512 in a disengaged position or state and prior to a locking engagement with the plunger 326. In FIG. 14B the piston 400 has been advanced in a distal direction toward the plunger 326. In some embodiments, the piston 500 may be advanced distally using the drive mechanism 402 operated by the controller 200 (FIG. 2). In other embodiments, the piston can be manually moved in the distal direction.

With continued reference to FIG. 14B, the catch 374 on the at least one retaining member 368 of the plunger 326 is deflected in a radially outward direction due to contact with the outer surface of post portion 521. After the catch 374 is positioned within the locking groove 527, such as when the upper surface of the connecting piece 525 engages the drive shoulder 327 of the plunger 326, distal movement of the piston 500 relative to the plunger 326 is stopped, and the at least one retaining member 368 can elastically deflect in a radially inward direction such that the catch 374 is positioned within the locking groove 527. While the at least one retaining member 368 is in the position shown in FIG. 14B, the plunger 326 is not in a locked engagement with the piston 500 because, due to the flexibility of the material between the first distal end 370 and a second proximal end 372 (see FIG. 7), the at least one retaining member 368 can be deflected in a radially outward direction with proximal movement of the piston 500 or distal movement of the plunger 326 (such as due to removal of the syringe from the injector). With the plunger 326 contacting the piston 500 as shown in FIG. 14B, the one or more release tabs 380 on the plunger 326 are aligned with the toothed portion 544 on the plunger engagement post 518.

With reference to FIGS. 14A and 14C, the plunger engagement sleeve 514 is moved from a disengaged position or state to an engaged position or state. Such movement of the plunger engagement sleeve 514 may be due to de-energizing the actuator and permitting the resiliently elastic member, such as the resiliently elastic member 484 described herein with reference to FIGS. 9-13J, to urge the plunger engagement sleeve 514 axially in a distal direction. In other embodiments, such movement of the plunger engagement sleeve 514 may be due to energizing of the actuator to urge the plunger engagement sleeve 514 axially in a distal direction. For example, the actuator may be actuated by a rotary or linear motor to move the actuator from a disengaged position to an engaged position in a distal direction. Energizing the actuator in this manner causes the plunger engagement sleeve 514 to be moved in the distal direction and builds an elastic restoring force in the resiliently elastic member. Movement of the plunger engagement sleeve 514 in the distal direction closes the receiving space 515 between the plunger engagement sleeve 514 and the plunger engagement post 518 to prevent removal of the one or more retaining members 368 of the plunger 326 from the receiving space 515 and the catch 374 of the one or more flexible retaining member 368 and the locking groove 527. Once the plunger engagement sleeve 514 is moved to the engaged position or state, the at least one retaining member 368 of the plunger 326 is captured between the plunger engagement sleeve 514 and the plunger engagement post 518 such that proximal axial movement of the piston 500 results in a corresponding proximal axial movement of the plunger 326 within the syringe barrel. The piston 500 and the connected plunger 326 may then be moved reciprocally within the barrel 318 of the syringe 300.

To unlock the syringe 300 from the syringe port of the injector and disengage the plunger 326 from the piston 500, the syringe 300 is rotated clockwise or counter-clockwise about the syringe longitudinal axis, relative to the syringe port. Because the plunger 326 is substantially free from rotation within the syringe barrel 318 due to frictional forces, rotation of the syringe 300 also causes the plunger 326 to rotate relative to the piston 500 about the longitudinal piston axis 520. Due to alignment of the one or more release tabs 380 on the plunger 326 with the toothed portion 544 on the plunger engagement post 518, rotation of the plunger 326 also rotates the plunger engagement post 518 relative to the plunger release sleeve 558 from the first position to the second position. Because the guiding pin 539 on the plunger engagement sleeve 514 is received within a longitudinal groove 538 of the plunger engagement post 518, the plunger engagement sleeve 514 also rotates with rotation of the plunger engagement post 518. Rotation of the plunger engagement sleeve 514 causes the guiding pin 539 to be guided along the ramped surface 566 of the plunger release sleeve 558 (see FIG. 16) moving the plunger engagement sleeve 514 in a proximal direction and compressing the resiliently elastic member, in a manner similar to the operation of the resiliently elastic member 484 described herein with reference to FIGS. 9-13J. In addition, rotation of the plunger engagement post 518 about the longitudinal piston axis 520 may build potential energy in the biasing member in a manner similar to the operation of the biasing member 496 described herein with reference to FIGS. 9-13J.

Movement of the guiding pin 539 along the ramped surface 566 of the plunger release sleeve 558 causes the plunger engagement sleeve 514 to be moved axially in a proximal direction from the engaged position or state to the disengaged position or state shown in FIG. 14A. In some embodiments, the plunger engagement sleeve 514 can be moved in the proximal direction by energizing or de-energizing the actuator to retract the plunger engagement sleeve 514. Movement of the plunger engagement sleeve 514 in the proximal direction opens the receiving space 515 between the plunger engagement sleeve 514 and the plunger engagement post 518 to permit removal of the catch 374 of the one or more flexible retaining member 368 and the locking groove 527 and allow removal of the one or more retaining members 368 of the plunger 326 from the receiving space 515.

Figure 18A:
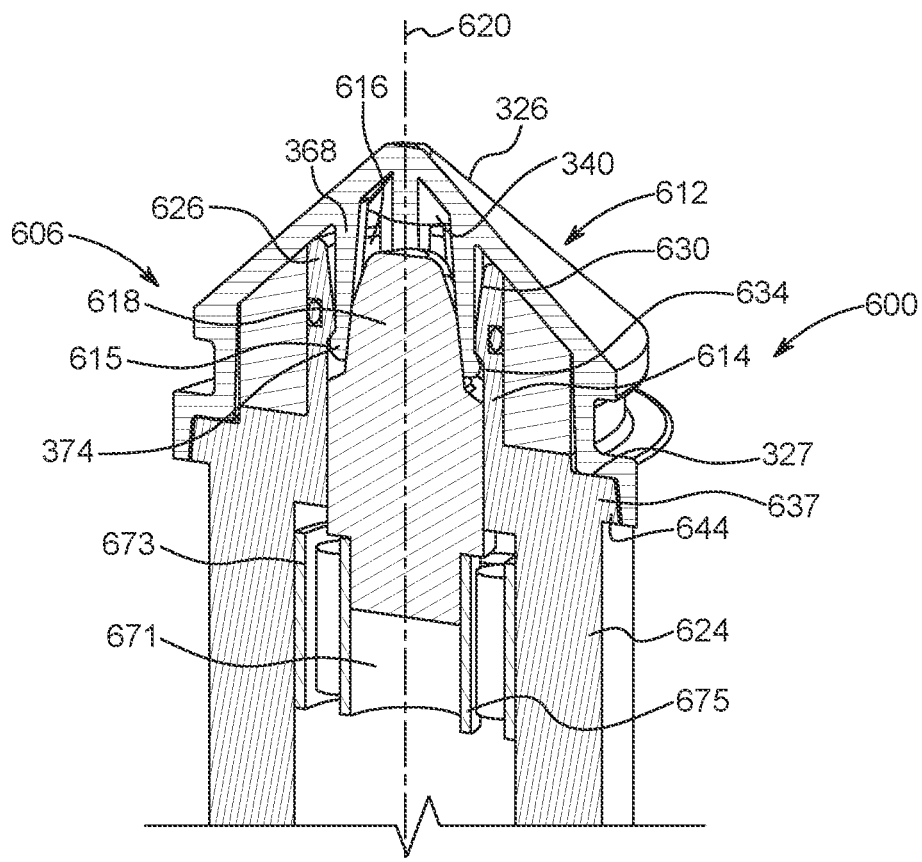
FIG. 18A is a perspective cross-sectional view of the operation of a piston of a plunger engagement mechanism according to another embodiment of the present disclosure.
Figure 18B:
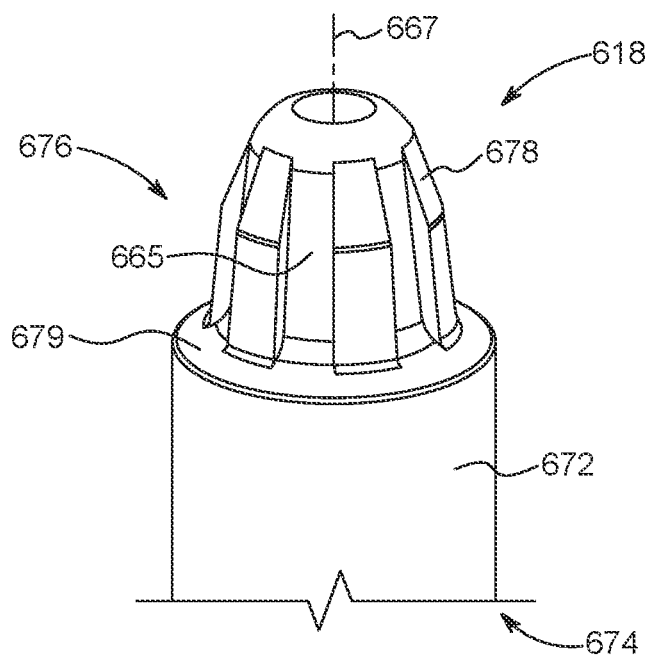
FIG. 18B is a perspective view of a plunger engagement post of the plunger engagement mechanism shown in FIG. 18A.
Figure 19:
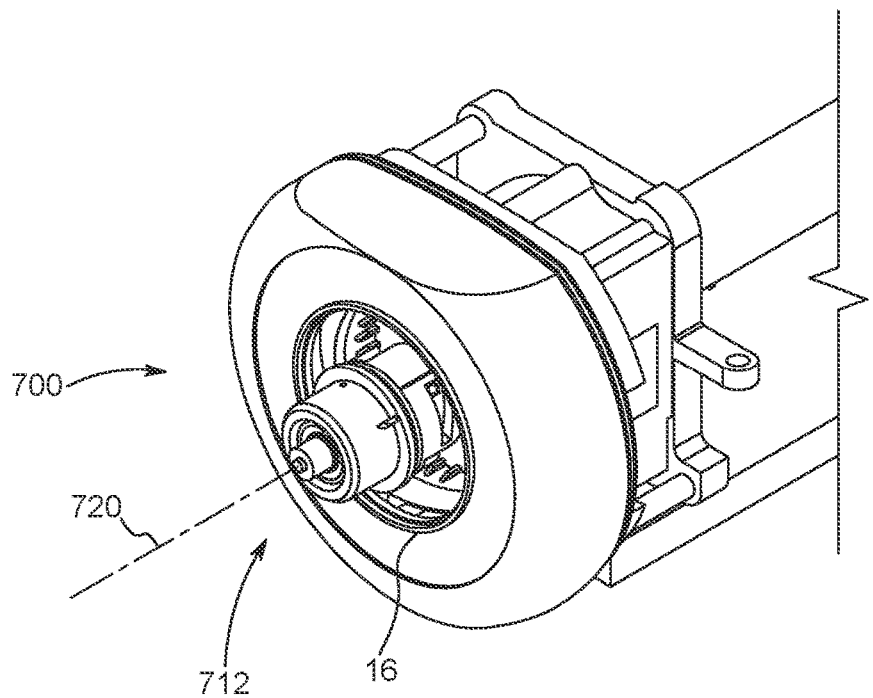
FIG. 19 is a perspective view of a piston of a fluid injector system having a plunger engagement mechanism according to another embodiment of the present disclosure.
Figure 20:
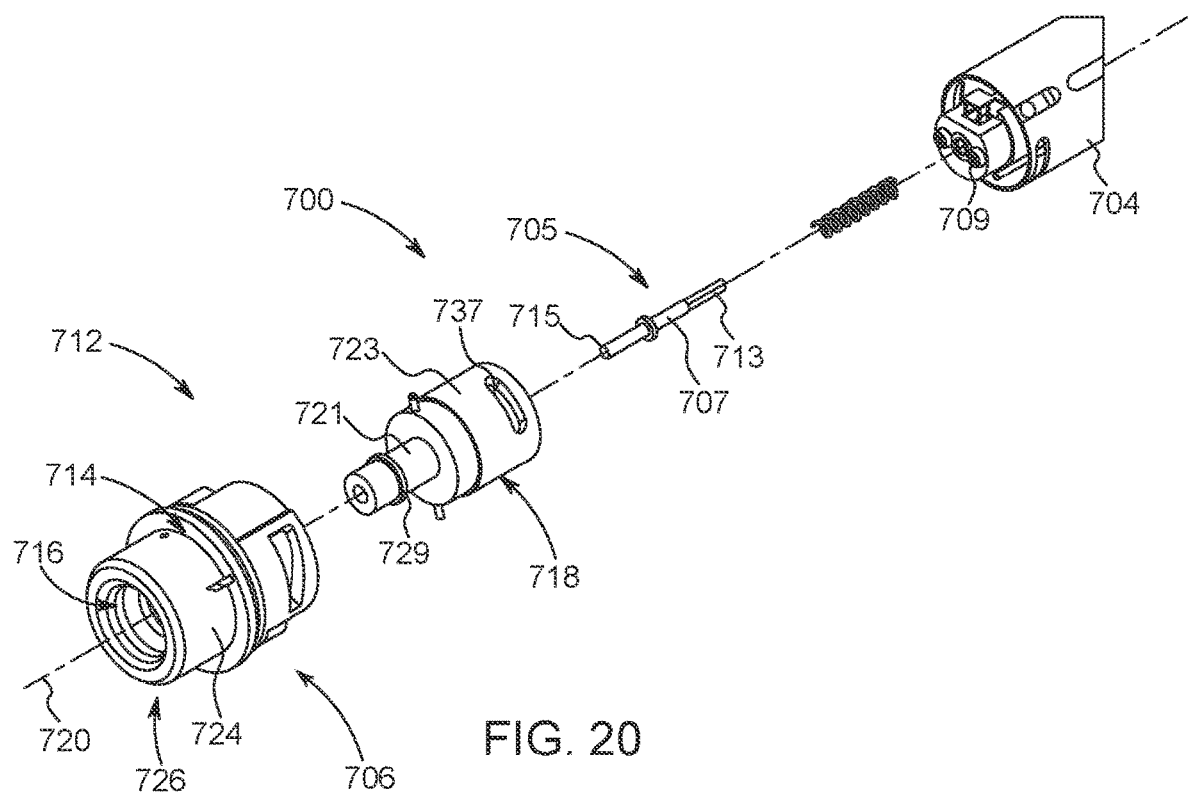
FIG. 20 is an exploded perspective view of the plunger engagement mechanism of FIG. 19.

With reference to FIGS. 18A-18B, a piston 600 and a plunger engagement mechanism 612 are shown in accordance with another embodiment of the present disclosure. The components of the piston 600 and the plunger engagement mechanism 612 shown in FIGS. 18A-18B are substantially similar or identical to the components of the piston 400 and the plunger engagement mechanism 412 described herein with reference to FIGS. 9-13J. Accordingly, reference numerals in FIGS. 18A-18B are used to illustrate identical components of the corresponding reference numerals in FIGS. 9-13J, with the exception that the leading number in reference numbers used in FIGS. 18A-18B has been changed from a "4" to a "6". For example, whereas a piston described in connection with FIGS. 9-13J is designated by a reference number "400", the piston in FIGS. 18A-18B is identified by reference number "600". As the previous discussion regarding the piston 400 and the plunger engagement mechanism 412 generally shown in FIGS. 9-13J is applicable to the piston 600 and the plunger engagement mechanism 612 shown in FIGS. 18A-18B, only the relative differences between the components shown in these figures are discussed hereinafter.

With reference to FIG. 18A, the plunger engagement mechanism 612 has a plunger engagement sleeve 614 having a central opening 616 and a plunger engagement post 618 that is reciprocally movable within the central opening 616 of the plunger engagement sleeve 614 along a direction of a longitudinal piston axis 620. The plunger engagement post 618 is reciprocally driven by an actuator, such as an actuator 422 shown in described herein with reference to FIG. 9. In some embodiments, the actuator may be a solenoid configured to be predominantly in the disengaged state and may be in the engaged state only during connection of the plunger 326 to the piston. In other embodiments, the actuator may be a rotary electric motor, a linear electric motor, or a linear actuator. In some embodiments, the actuator is a linear actuator that can be back driven manually in the event of a power loss to the injector.

The plunger engagement mechanism 612 is operable between an engaged position or state, and a disengaged position or state. In the engaged position or state, the plunger engagement post 618 may be positioned within the plunger engagement sleeve 614 to capture at least one retaining member 368 associated with the plunger 326 in a receiving space 615 between the plunger engagement sleeve 614 and the plunger engagement post 618. Conversely, in the disengaged position or state, the plunger engagement post 618 may be positioned proximally relative to the plunger engagement sleeve 614 to permit removal of the at least one retaining member 368 associated with the plunger 600 from the receiving space 615 between the plunger engagement sleeve 614 and the plunger engagement post 618.

With continued reference to FIG. 18A, plunger engagement sleeve 614 has a hollow body 624, wherein at least a portion of an outer surface of the hollow body 624 defines at least a portion of the piston head 606. A distal portion or end 626 of the plunger engagement sleeve 614 is shaped to be received within the interior cavity 340 of the plunger 326, while at least a portion of the plunger 326, such as the at least one retaining member 368, is configured to be received within the central opening 616. The central opening 616 extends through the hollow body 624 of the plunger engagement sleeve 614. An inner surface of the central opening 616 may have a ramp 630 such that an inner diameter of the opening 616 narrows in a direction from the distal end of the hollow body 624 toward a proximal portion or end. The ramp 630 may be configured for deflecting the at least one retaining member 368 associated with the plunger 326 in a radially inward direction during connection of the plunger 326 to the plunger engagement sleeve 614 by contacting the catch 374 of the one or more flexible retaining member 368 as the piston head 606 moves distally relative to the plunger 326. The ramp 630 may terminate at a locking rib 634. An outer surface 642 of the plunger engagement sleeve 614 may have a toothed portion 644, similar to the toothed portion 444 described herein with reference to FIGS. 9-13J. The toothed portion 644 may be configured for interacting with the one or more release tabs 380 on the plunger 326 during rotation of the plunger 326 relative to the piston 600 (shown in FIG. 8C).

With reference to FIG. 18B, the plunger engagement post 618 is shown separate from the plunger engagement mechanism 612. The plunger engagement post 618 has a shaft 672 having a proximal end 674 and a distal end 676. The distal end 676 of the shaft 672 has a tapered end surface 678 configured for contacting the at least one retaining member 368 on the plunger 326 when the plunger engagement post 618 is in an engaged position to prevent removal of the plunger 326 from the piston 600. The proximal end 674 of the shaft 672 is configured for connecting to an actuator, similar to the actuator 422 described herein with reference to FIGS. 9-13J for moving the plunger engagement post 618 relative to the plunger engagement sleeve 614 between an engaged position or state and a disengaged position or state.

With continued reference to FIG. 18B, the plunger engagement post 618 further includes at least one groove 665 recessed into the body of the shaft 672 at the distal end 676. In some embodiments, the at least one groove 665 may be configured to receive the at least one retaining member 368 of the plunger 326 when the plunger engagement post 618 is rotated about a longitudinal axis 667. The at least one groove 665 may be linearly or curvilinearly contiguous between a ledge 679 near the proximal end 674 and the distal end 676 of the shaft 672. In some embodiments, the at least one groove 665 may extend in a direction parallel to the longitudinal axis 667 of the plunger engagement post 618.

With continued reference to FIG. 18B, a plurality of grooves 665 are spaced apart radially from the longitudinal axis 667 along a circumference of the distal end 676 of the shaft 672. In embodiments where more than two grooves 665 are provided, the grooves 665 may be evenly spaced apart from each other and separated from each other by an outer surface 667 of the shaft 672. In some embodiments, the number and spacing of grooves 665 may correspond to the number and spacing of the retaining members 368 on the plunger 326. In one exemplary and non-limiting aspect with six retaining members 368 having equal angular separation therebetween, such as shown in FIG. 8C, the corresponding plunger engagement post 618 has six grooves 665 separated by 60 degrees from the grooves 665 adjacent on either side.

With reference to FIG. 18A, the proximal end 674 of the shaft 672 is received within a rotating mechanism 671 that is slidably mounted within the hollow body 624 of the plunger engagement sleeve 614. In some embodiments, the rotating mechanism 671 may have a first portion 673 that is slidably mounted within the hollow body 624 and is fixed from rotating relative to the plunger engagement sleeve 614 and a second portion 675 that is fixed to the plunger engagement post 618 and is rotatable relative to the first portion 673 and the plunger engagement sleeve 614. In some embodiments, the rotating mechanism 671 may be configured for one-way rotation, such as in a clockwise or a counter-clockwise direction about the longitudinal axis 620. For example, the rotating mechanism 671 may be a one-way clutch.

Having described the structure of the plunger 326 and the piston 600 in accordance with one non-limiting embodiment of the present disclosure, a method of engagement and disengagement of the plunger 326 with and from the piston 600 will now be described.

FIG. 18A shows the piston 600 with its plunger engagement mechanism 612 in an engaged position or state with the plunger 326. As described herein with reference to FIGS. 13A-13J, the plunger 326 can be connected to the piston 600 by moving the piston 600 distally to permit insertion of the one or more retaining members 368 of the plunger 326 into the receiving space 615 between the plunger engagement sleeve 614 and the plunger engagement post 618. In some embodiments, the piston 600 may be advanced distally using the drive mechanism 402 operated by the controller 200

(FIG. 2). In other embodiments, the piston 600 can be manually moved in the distal direction.

The piston 600 is advanced axially in a distal direction such that the at least one retaining member 368 of the plunger 326 is flexibly received within the central opening 616 of the plunger engagement sleeve 614 such that the at least one retaining member 368 is deflected radially inward due to the contact between the catch 374 and the ramp 630. In embodiments having a plurality of retaining members 368, each of the retaining members 368 is deflected in the radially inward direction. In some embodiments, there may be guiding surfaces on sides of tapered end surface 678 to assist with rotation of the plunger engagement post 618 into correct orientation to self-align with retaining members 368 on the plunger 326.

During continued axial movement of the piston 600 in a distal direction, the catch 374 is deflected radially inward over the locking rib 634 of the piston engagement sleeve 614. After the catch 374 is positioned proximally relative to the locking rib 634, distal movement of the piston 400 relative to the plunger 326 is stopped, such as when the drive shoulder 327 of the plunger 326 engages a corresponding drive ledge 637 on the piston 600, and the at least one retaining member 368 can elastically deflect in a radially outward direction such that the catch 374 is positioned proximally of the locking rib 634. In this configuration, the plunger engagement post 618 is still in the disengaged position or state, such as due to activation of the actuator described herein with reference to FIGS. 9-14C. With the plunger 326 connected to the piston 600, the one or more release tabs 380 on the plunger 326 are aligned with the toothed portion 644 on the outer surface 642 of the plunger engagement sleeve 614.

With distal movement of the plunger engagement post 618 from the disengaged state or position to the engaged state or position, the receiving space 615 between the plunger engagement sleeve 614 and the plunger engagement post 618 is closed to prevent removal of the one or more retaining members 368 of the plunger 326 from the receiving space 615. As the plunger engagement post 618 is moved to the engaged position or state, the catch 374 of the at least one retaining member 368 of the plunger 326 is captured between the plunger engagement sleeve 614 and the outer surface 667 of the plunger engagement post 418 proximal to the locking rib 634. The piston 600 and the connected plunger 326 may then be moved reciprocally within the barrel 318 of the syringe 300). In some embodiments, the piston 600 may be advanced distally to deliver the fluid from the syringe 300 or proximally to fill the syringe 300 with fluid using the drive mechanism 402 operated by the controller 200 (FIG. 2).

To unlock the syringe 300 from the syringe port of the injector and disengage the plunger 326 from the piston 600, the syringe 300 may be rotated clockwise or counter-clockwise about the syringe longitudinal axis, relative to the syringe port. Due to alignment of the one or more release tabs 380 on the plunger 326 with the toothed portion 644 on the plunger engagement sleeve 614, rotation of the plunger 326 also rotates the plunger engagement sleeve. Because the plunger engagement post 618 is connected to the plunger engagement sleeve 614 via the rotating mechanism 671, the plunger engagement post 618 does not rotate with rotation of the plunger engagement sleeve 614. In this manner, the retaining members 368 of the plunger 326 slide into the grooves 665 on the plunger engagement post 618.

With the retaining members 368 of the plunger 326 positioned in the grooves 665 on the plunger engagement post 618, the receiving space 615 between the plunger engagement sleeve 614 and the plunger engagement post 618 is opened to permit removal of the one or more retaining members 368 of the plunger 326 from the receiving space 615 by flexing distal movement of the catch 374 of the at least one retaining member 368 over the locking rib 634. The syringe 300 can be pulled in the distal direction or the plunger 600 can be retracted in the proximal direction to remove the plunger 326 from the piston 600. During such relative movement of the piston 326 to the plunger 600 in a direction away from each other, the catch 374 is deflected over the locking rib 634 of the piston engagement sleeve 614 to permit a removal of the one or more retaining members 368 from the piston 600.

With reference to FIGS. 19-21B, a piston 700 and a plunger engagement mechanism 712 are shown in accordance with another embodiment of the present disclosure. The components of the piston 700 and the plunger engagement mechanism 712 shown in FIGS. 19-21B are substantially similar or identical to the components of the piston 400 and the plunger engagement mechanism 412 described herein with reference to FIGS. 9-13J. Accordingly, reference numerals in FIGS. 19-21B are used to illustrate identical components of the corresponding reference numerals in FIGS. 9-13J, with the exception that the leading number in reference numbers used in FIGS. 19-21B has been changed from a "4" to a "7". As the previous discussion regarding the piston 400 and the plunger engagement mechanism 412 generally shown in FIGS. 9-13J is applicable to the piston 700 and the plunger engagement mechanism 712 shown in FIGS. 19-21B, only the relative differences between the components shown in these figures are discussed hereinafter.

With initial reference to 19, the piston 700 and the plunger engagement mechanism 712 are shown in combination with a syringe port 16 of an injector, such as the injector 10 shown in FIG. 1. The piston 700 is reciprocally movable within the syringe port 16 in a direction of a longitudinal piston axis 720, such as via drive mechanism 402 shown in FIG. 2.

With reference to 20, an exploded view of the piston 700 and the plunger engagement mechanism 712 is shown. The piston 700 has a body 704 and a piston head 706 at a distal end of the body 704. The piston head 706 is configured for removably connecting to a plunger of a syringe, such as the plunger 326 shown in FIGS. 7-8B. The plunger engagement mechanism 712 is integrated into the piston head 706. In some embodiments, at least a portion of piston head 706 and/or plunger engagement mechanism 712 may be made from a transparent or translucent material that is configured to permit a passage of light emitted by one or more lights in piston 700 for illuminating at least a portion of plunger 326 and/or syringe 300.

With continued reference to 20, the piston 700 has a sensing member 705, such as a pin 707 and a sensor 709. The pin 707 has a proximal end 713 configured for contacting the sensor 709 when a distal end 715 of the pin 707 is urged in a proximal direction, such as due to contact between the plunger 326 and the distal end 715 of the pin 707. The pin 707 may extend along a longitudinal axis 720 of the piston 700 and may protrude through at least a portion of the piston head 706. The pin 707 may be operative for sensing contact with a surface, such as a surface of the plunger 326, and send one or more signals to controller 200 (FIG. 2) to control a movement of the piston 700 based on the sensed condition. For example, an initial contact between the distal end 715 of the pin 707 and the plunger 326 may cause the pin 707 to be moved in a proximal direction such that it contacts the sensor 709. The sensor 709 may be operatively connected to controller 200 such that, upon activation of the sensor 709 by the pin 707, the sensor 709 controls the movement of the drive mechanism of piston 700. For example, the drive mechanism may be stopped or slowed from a first rate to a second, slower rate and the distal end 715 of the pin 707 and the plunger 326. The pin 707 may be biased to its distal position by a spring 711.

With continued reference to 20, the plunger engagement mechanism 712 has a plunger engagement sleeve 714 having a central opening 716 and a plunger engagement post 718. The plunger engagement post 718 is translatable along the direction of the longitudinal piston axis 720 relative to the plunger engagement sleeve 714 due to activation of an actuator 722 (shown in FIGS. 21A-21B). In some embodiments, the plunger engagement post 718 may be axially movable between an engaged position, in which the plunger 326 is in a locked engagement with the piston 700 due to capture of the at least one retaining member 368 of the plunger 326 between the plunger engagement sleeve 714 and the plunger engagement post 718, and a disengaged portion, in which the plunger 326 can be removed from the piston 700.

With continued reference to 20, the plunger engagement post 718 has a post portion 721 that extends distally from a proximal portion 723. The plunger engagement post 718 further has a radial groove 737 configured for receiving a guiding pin (not shown). The post portion 721 of the plunger engagement post 718 has a locking lip 729 that is configured to interact with the catch 374 of the at least one retaining member 368 of the plunger 326. The post portion 721 may be shaped to deflect the at least one retaining member 368 in a radially outward direction due to contact of the catch 374 with an outer surface of the post portion 721 and/or the locking lip 729. In this manner, distal movement of the piston 700 relative to the plunger 326 causes the at least one retaining member 368 to be deflected radially outward due to the contact between the catch 374 and the post portion 721. In embodiments having a plurality of retaining members 368, each of the retaining members 368 is deflected in the radially outward direction.

With continued reference to 20, the plunger engagement sleeve 714 has a hollow body 724, wherein at least a portion of an outer surface of the hollow body 724 defines at least a portion of the piston head 706. A distal portion or end 726 of the plunger engagement sleeve 714 is shaped to be received within the interior cavity 340 of the plunger 326 (shown in FIG. 21A), while at least a portion of the plunger 326, such as the at least one retaining member 368, is configured to be received within the central opening 716. The central opening 716 extends through the hollow body 724 of the plunger engagement sleeve 714.

A portion of an inner surface 728 of the central opening 716 at the distal end of the opening 716 may have a stepped inner diameter that decreases in diameter in a direction from a distal end of the plunger engagement sleeve 726 to a proximal end of the plunger engagement sleeve 714. For example, the opening 716 may have a first step 717 having a first inner diameter and a second step 719 positioned proximally of the first step 717 having a second diameter that is smaller than the first diameter of the first step 717. A ramp 730 may be provided between the first and second steps 717, 719 for deflecting the at least one retaining member 368 associated with the plunger 326 in a radially inward direction during connection of the plunger 326 to the distal portion or end 726 of the plunger engagement sleeve 714.

Having described the structure of the plunger 326 (see disclosure herein with reference to FIGS. 6-8C) and the piston 700 in accordance with one non-limiting embodiment of the present disclosure, a method of engagement and disengagement of the plunger 326 with and from the piston 700 will now be described with reference to FIGS. 21A-21B. A portion of the syringe 300 is shown in FIGS. 21A-21B.

Figure 21A:
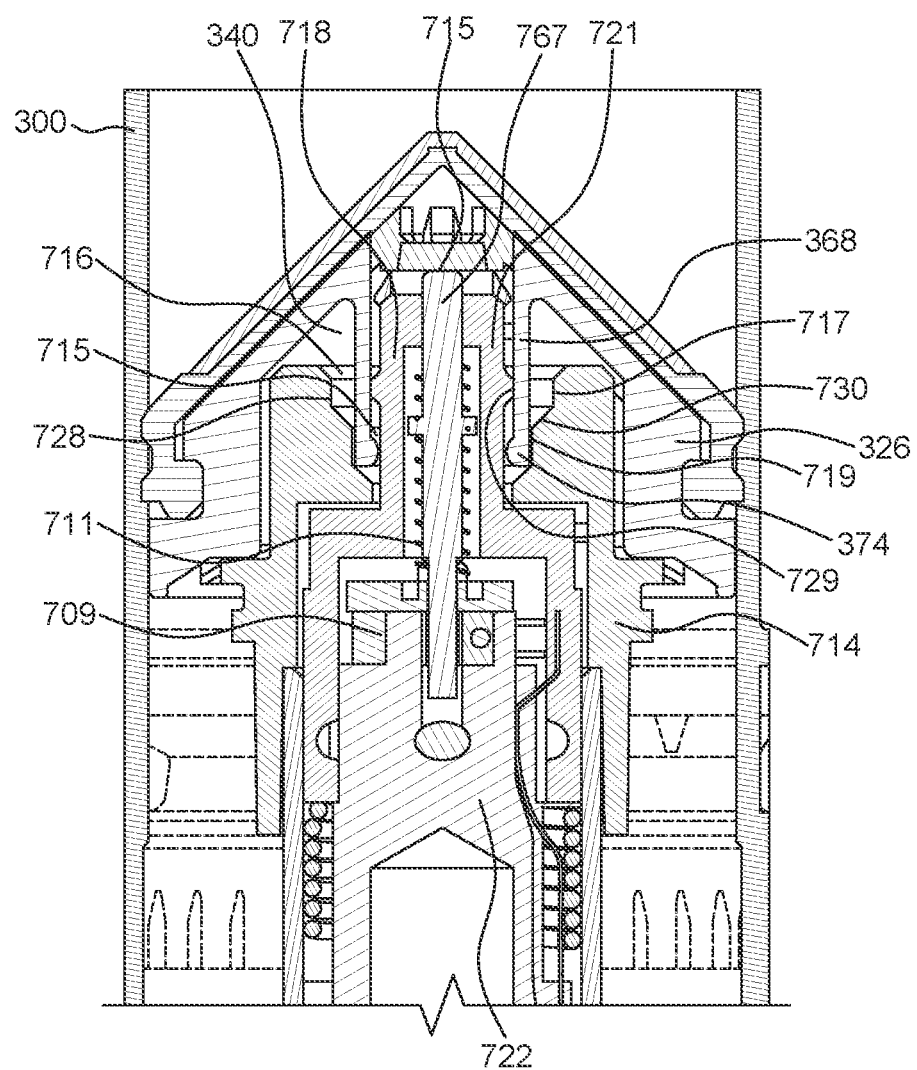
FIGS. 21A-21B are cross-sectional views of the operation of the plunger engagement mechanism of FIG. 19.

FIG. 21A shows the piston 700 with its plunger engagement mechanism 712 in a disengaged position or state and prior to a locking engagement with the plunger 326. In some embodiments, the piston 700 may be advanced distally using the drive mechanism 402 operated by the controller 200 (FIG. 2). In other embodiments, the piston can be manually moved in the distal direction.

As piston 700 may be advanced distally, the catch 374 on the at least one retaining member 368 of the plunger 326 is deflected in a radially outward direction due to contact with the locking lip 729 on the post portion 721. The plunger engagement post 718 is in its disengaged position and is moved axially in a distal direction relative to plunger engagement sleeve 714 such that the retaining member 368 can deflect radially outward into the space defined by the first step 717. After the catch 374 is positioned proximally relative to the locking lip 729, the at least one retaining member 368 can elastically deflect in a radially inward direction, for example due to the elastic flexibility of retaining member 368 in combination with ramp 730 between the first and second steps 717, 719. While the at least one retaining member 368 is in the position shown in FIG. 21A, the plunger 326 is not in a locked engagement with the piston 700 because the at least one retaining member 368 can be flexibly deflected in a radially outward direction with proximal movement of the piston 700 or distal movement of the plunger 326 (such as due to removal of the syringe from the injector), as described herein.

Figure 21B:
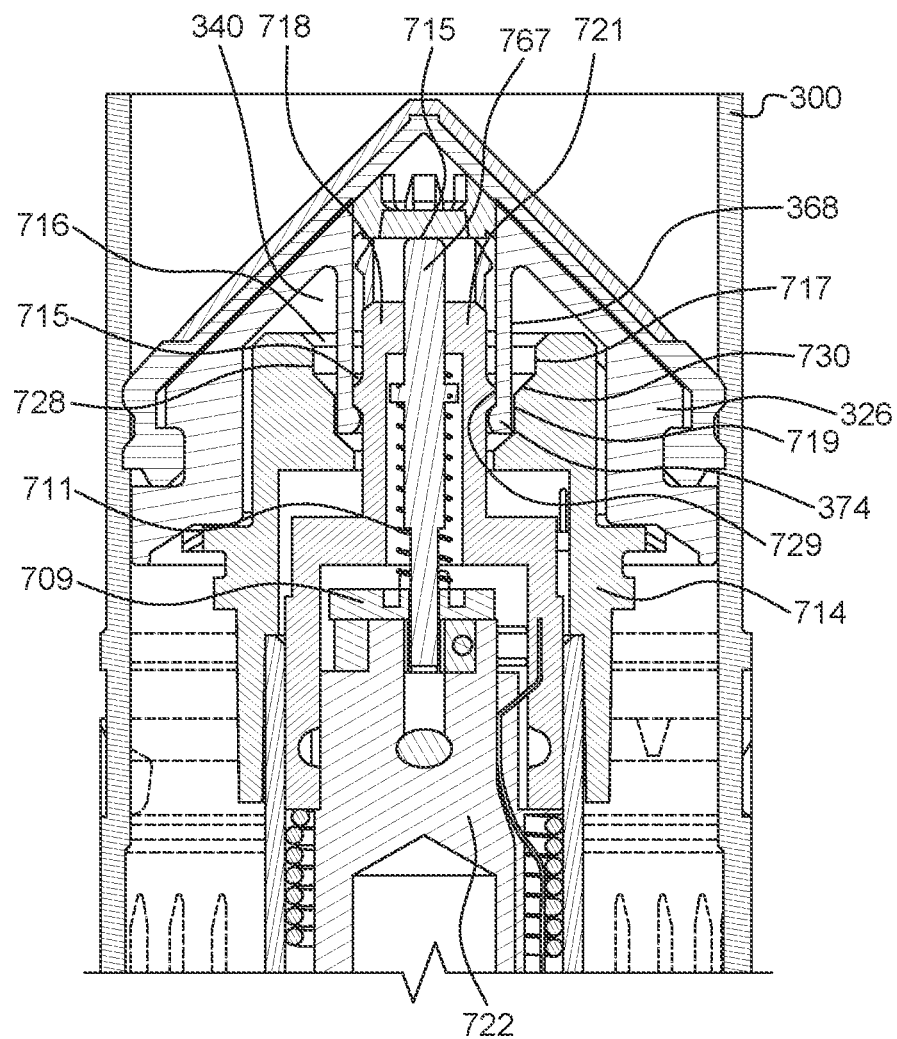

With reference to FIG. 21B, the plunger engagement post 718 is moved from a disengaged position or state to an engaged position or state by moving in a proximal direction along the longitudinal piston axis 720. Such movement of the plunger engagement post 718 may be due to de-energizing the actuator and permitting a resiliently elastic member, such as the resiliently elastic member 484 described herein with reference to FIGS. 9-13J, to urge the plunger engagement post 718 axially in a proximal direction or, alternatively by energizing the actuator to move plunger engagement post 718 in the proximal direction. Movement of the plunger engagement post 718 in the proximal direction locks the at least one retaining member 368 and the catch 374 in the space defined by the second step 719 of the plunger engagement sleeve 714. Due to the smaller second diameter of the second step 719 in combination with the increased diameter of locking lip 729, the one or more retaining members 368 of the plunger 326 are captured within the receiving space 715 between the plunger engagement sleeve 714 and the plunger engagement post 718 such that reciprocal axial movement of the piston 700 results in a corresponding reciprocal axial movement of the plunger 326 within the syringe barrel 318. To unlock the plunger 326 from the plunger engagement mechanism 712, the plunger engagement post 718 is moved to the disengaged position via axial movement of plunger engagement post 718 in the distal direction, moving locking lip 729 distally, permitting catch 374 of the one or more retaining members 368 to move around locking lip 729 in the first step 717 and allowing removal of the one or more retaining members 368 of plunger 326 from the receiving space 715 between the plunger engagement sleeve 714 and plunger engagement post 718.

With reference to FIGS. 22A-22E, a piston 800 and a plunger engagement mechanism 812 are shown in accordance with another embodiment of the present disclosure. The components of the piston 800 and the plunger engagement mechanism 812 shown in FIGS. 22A-22E are substantially similar or identical to the components of the piston 400 and the plunger engagement mechanism 412 described herein with reference to FIGS. 9-13J. Accordingly, reference numerals in FIGS. 22A-22E are used to illustrate identical components of the corresponding reference numerals in FIGS. 9-13J, with the exception that the leading number in reference numbers used in FIGS. 22A-22E has been changed from a "4" to an "8". As the previous discussion regarding the piston 400 and the plunger engagement mechanism 412 generally shown in FIGS. 9-13J is applicable to the piston 800 and the plunger engagement mechanism 812 shown in FIGS. 22A-22E, only the relative differences between the components shown in these figures are discussed hereinafter.

Figure 22A:
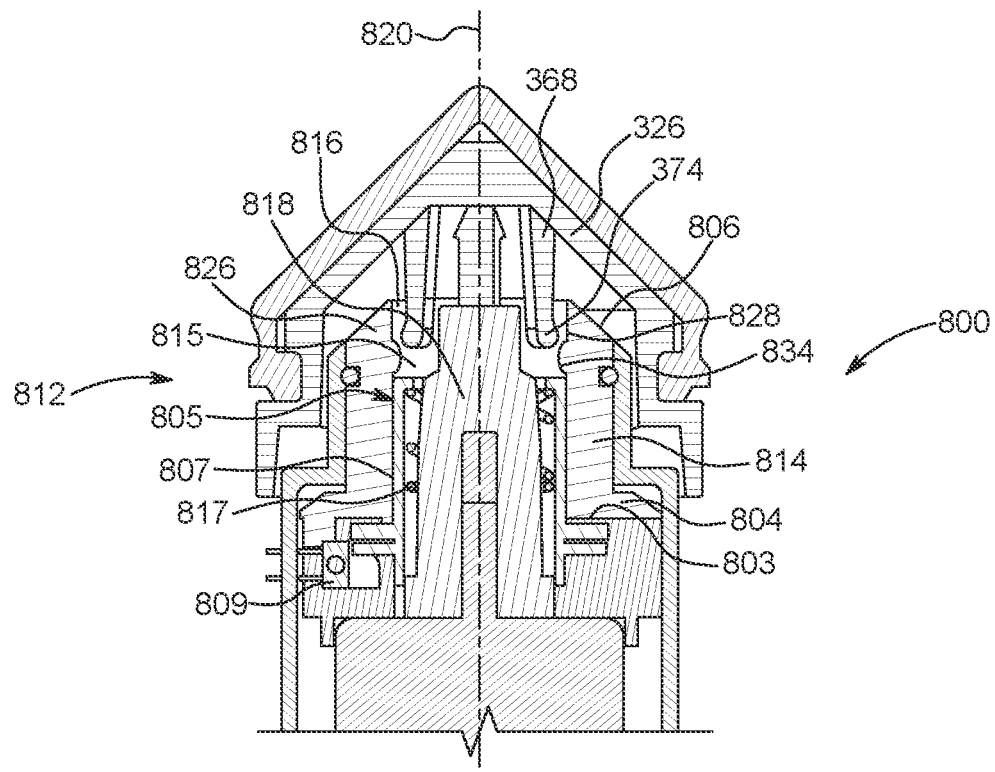
FIGS. 22A-22E are cross-sectional views of the operation of a plunger engagement mechanism according to another embodiment of the present disclosure.

With reference to FIG. 22A, the piston 800 has a body 804 and a piston head 806 at a distal end of the body 804. The piston head 806 is configured for removably connecting to a plunger of a syringe, such as the plunger 326 shown in FIG. 8C. The plunger engagement mechanism 812 is integrated into the piston head 806. In some embodiments, at least a portion of the piston head 806 and/or plunger 326 may be made from a transparent or translucent material that is configured to permit a passage of light emitted by one or more lights 803 in the piston 800 for illuminating at least a portion of the plunger 326 and/or the syringe 300.

The piston 800 has a sensing member 805, such as a sensing sleeve 807 and a sensor 809. The sensing sleeve 807 has a proximal end 813 configured for interacting with the sensor 809 when a distal end 815 of the sensing sleeve 807 is urged in a proximal direction, such as due to contact between the one or more retaining members 368 of the plunger 326 and the distal end 815 of the sensing sleeve 807. The sensing sleeve 807 may extend along a longitudinal axis 820 of the piston 800 and may be recessed within the piston head 806. The sensing sleeve 807 may be operative for sensing contact with a surface, such as a surface of the plunger 326, and a controller 200 may be signaled to control a movement of the piston 800 based on the sensed condition. In some embodiments, the distal end 815 of the sensing sleeve 807 may be configured for contacting the one or more retaining members 368 of the plunger 326 when the plunger 326 is connected to the piston 800. An initial contact between the distal end 815 of the sensing sleeve 807 and the one or more retaining members 368 of the plunger 326 may cause the sensing sleeve 807 to be retracted in a proximal direction such that sensing sleeve 807 activates the sensor 809. The sensor 809 may be operatively connected to controller 200 and the drive mechanism of the piston 800 such that, upon activation of the sensor 809 by the sensing sleeve 807, the sensor 809 signals controller 200 to control the movement of the drive mechanism. For example, the drive mechanism may be stopped or slowed from a first rate to a second, slower rate. The sensing sleeve 807 may be biased to its distal position by a biasing member, such as spring 817.

The plunger engagement mechanism 812 has a plunger engagement sleeve 814 having a central opening 816 and a plunger engagement post 818. The plunger engagement post 818 is translatable along the direction of the longitudinal piston axis 820 relative to the plunger engagement sleeve 814 due to activation of an actuator, such as an actuator 422 described herein with reference to FIGS. 9-13J. In some embodiments, the plunger engagement post 818 may be axially movable between an engaged position, in which the plunger 326 is in a locked engagement with the piston 800 due to capture catch 374 of the at least one retaining member 368 of the plunger 326 under locking rib 834 on the plunger engagement sleeve 814 and the plunger engagement post 818, and a disengaged portion, in which the plunger 326 can be removed from the piston 800.

Plunger engagement sleeve 814 has a hollow body 824, wherein at least a portion of an outer surface of the hollow body 824 defines at least a portion of the piston head 806. A distal portion or end 826 of the plunger engagement sleeve 814 is shaped to be received within the interior cavity 340 of the plunger 326, while at least a portion of the plunger 326, such as the at least one retaining member 368, is configured to be received within the central opening 816. The central opening 816 extends through the hollow body 824 of the plunger engagement sleeve 814.

An inner surface of the central opening 816 has a locking rib 834 that protrudes radially inward from the inner surface 828. The locking rib 834 is configured for deflecting the at least one retaining member 368 associated with the plunger 326 in a radially inward direction during connection of the plunger 326 to the distal portion or end of the plunger engagement sleeve 814. In some embodiments, the locking rib 834 extends continuously or discontinuously around the inner surface 828 of the hollow body 824 of the plunger engagement sleeve 814 and defines a surface that engages the at least one catch 368 on the at least one retaining member 368 on the plunger 326 to prevent removal of the plunger 326 from the piston 800 when the plunger 326 is in locked engagement with the plunger engagement mechanism 812, as described herein.

Having described the structure of the plunger 326 and the piston 800 in accordance with one non-limiting embodiment of the present disclosure, a method of engagement and disengagement of the plunger 326 with and from the piston 800 will now be described with reference to FIGS. 22A-22E.

FIG. 22A shows the piston 700 with its plunger engagement mechanism 812 in a disengaged position or state and prior to a locking engagement with the plunger 326. In some embodiments, the piston 800 may be advanced distally using the drive mechanism 402 operated by the controller 200 (FIG. 2). In other embodiments, the piston can be manually moved in the distal direction.

Figure 22B:
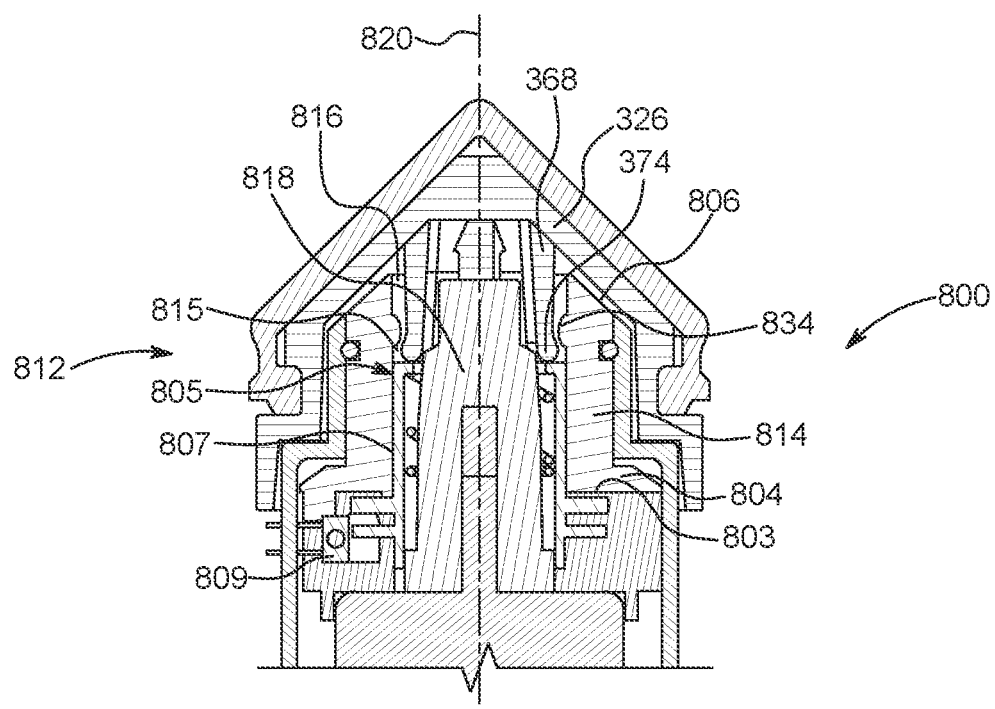

Moving from FIG. 22A to FIG. 22B, as the piston 800 is advanced toward the plunger 326, the at least one retaining member 368 on the plunger 326 contacts the sensing sleeve 807 such that the sensing sleeve 807 is moved proximally toward the sensor 809. The catch 374 on the at least one retaining member 368 of the plunger 326 is deflected in a radially inward direction due to contact with the locking rib 834 on the plunger engagement sleeve 814. The plunger engagement post 818 is in its disengaged position, for example retracted in the proximal direction. While the at least one retaining member 368 is in the position shown in FIG. 22B, the plunger 326 is not in a locked engagement with the piston 800 because the at least one retaining member 368 can be flexibly deflected in a radially inward direction with proximal movement of the piston 800 or distal movement of the plunger 326 (such as due to removal of the syringe from the injector).

Figure 22C:
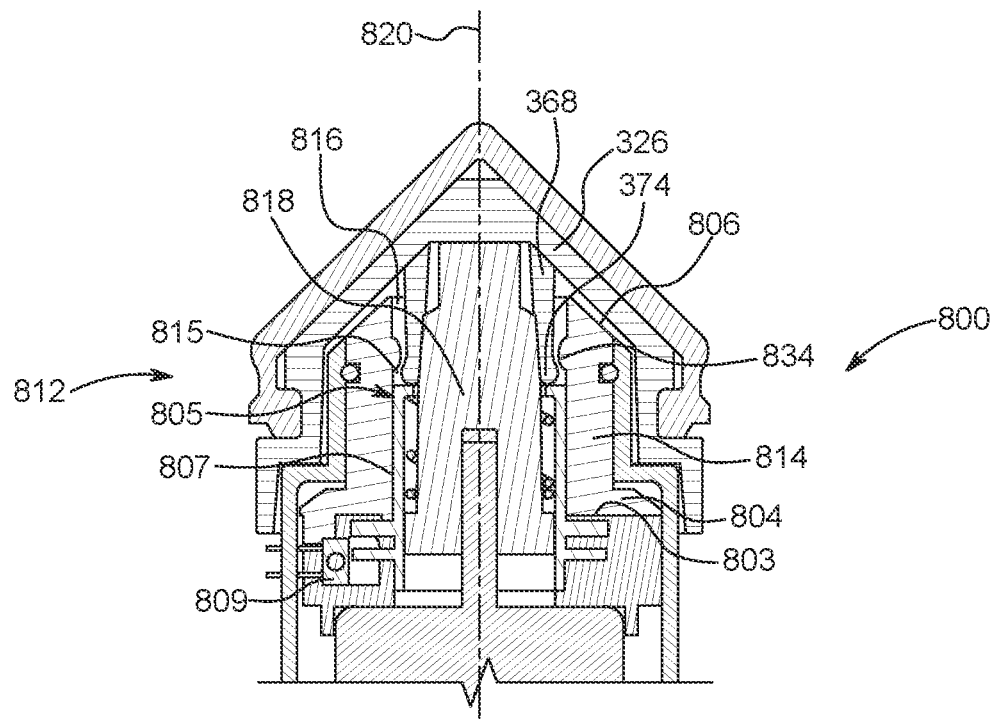

With reference to FIG. 22C, as the sensing sleeve 807 is moved proximally due to contact with the at least one retaining member 368 of the plunger 326, the sensor 809 detects the presence of the sensing sleeve 807 and actuates the actuator 822 to move the plunger engagement post 818 axially in a distal direction from a disengaged position or state to an engaged position or state. Such movement of the plunger engagement post 718 may be due to de-energizing the actuator 822. In other embodiments, movement of the plunger engagement post 718 may be due to energizing the actuator 822, such as a solenoid, or by operation of a motor to move the actuator.

With movement of the plunger engagement post 818 from the disengaged state or position to the engaged state or position, the receiving space 815 between the plunger engagement sleeve 814 proximal to the locking rib 834 and the plunger engagement post 818 is closed to prevent removal of the catch 374 of the one or more retaining members 368 of the plunger 326 from the receiving space 815. As the plunger engagement post 818 is moved to the engaged position or state, the catch 374 of the at least one retaining member 368 of the plunger 326 is captured between the locking rib 834 on the plunger engagement sleeve 814 and the plunger engagement post 818. The piston 800 and the connected plunger 326 may then be moved reciprocally within the barrel 318 of the syringe. In some embodiments, the piston 800 may be advanced distally to deliver the fluid from the syringe 300 or proximally to fill the syringe 300 with fluid using the drive mechanism 402 operated by the controller 200 (FIG. 2).

Figure 22D:
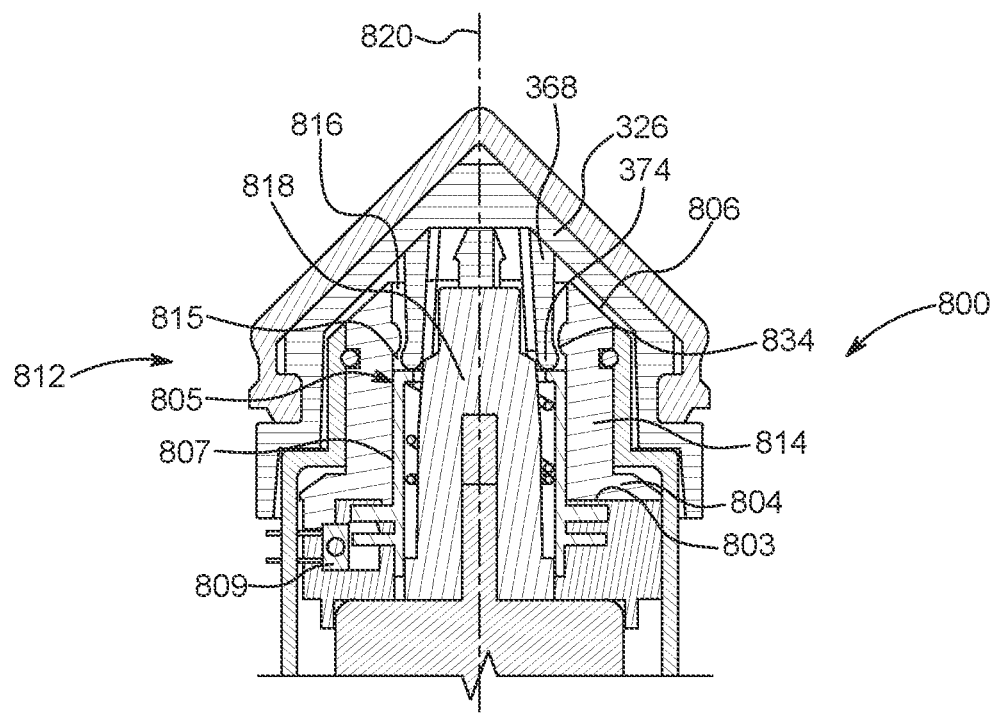
Figure 22E:
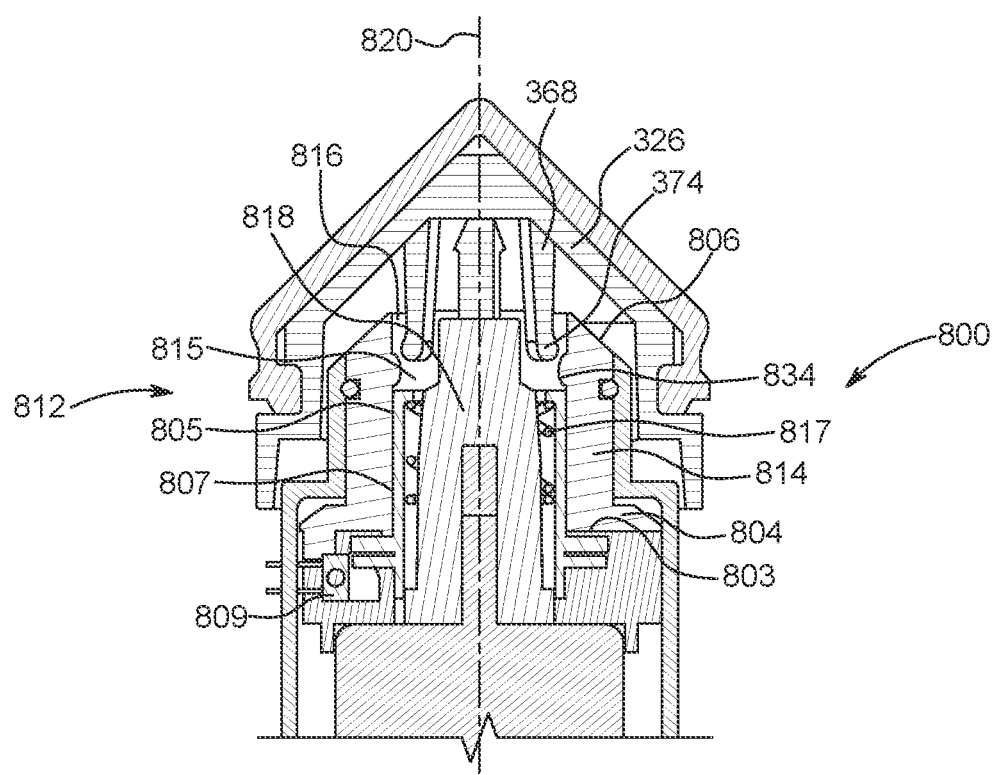

With reference to FIG. 22D, to unlock the plunger 326 from the plunger engagement mechanism 812, the plunger engagement post 818 is moved to the disengaged position via axial movement in the distal direction, for example by the actuator (as described herein) or a stored restoring force from a biasing member, which permits removal of the one or more retaining members 368 of the plunger 326 from the receiving space 815 between the plunger engagement sleeve 814 and the plunger engagement post 718. Removal of the plunger 326 from the piston 800 permits the sensing sleeve 807 to be moved in a distal direction due to a restoring force provided by the spring 817 (FIG. 22E).

With reference to FIGS. 23A-23G, a piston 900 and a plunger engagement mechanism 912 are shown in accordance with another embodiment of the present disclosure. Certain components of the piston 900 and the plunger engagement mechanism 912 shown in FIGS. 23A-23G are substantially similar or identical to the components of the piston 400 and the plunger engagement mechanism 412 described herein with reference to FIGS. 9-13J. As certain features of the previous discussion regarding the piston 400 and the plunger engagement mechanism 412 generally shown in FIGS. 9-13J are applicable to the piston 900 and the plunger engagement mechanism 912 shown in FIGS. 23A-23G, only the relative differences between the components shown in these figures are discussed hereinafter.

Figure 23A:
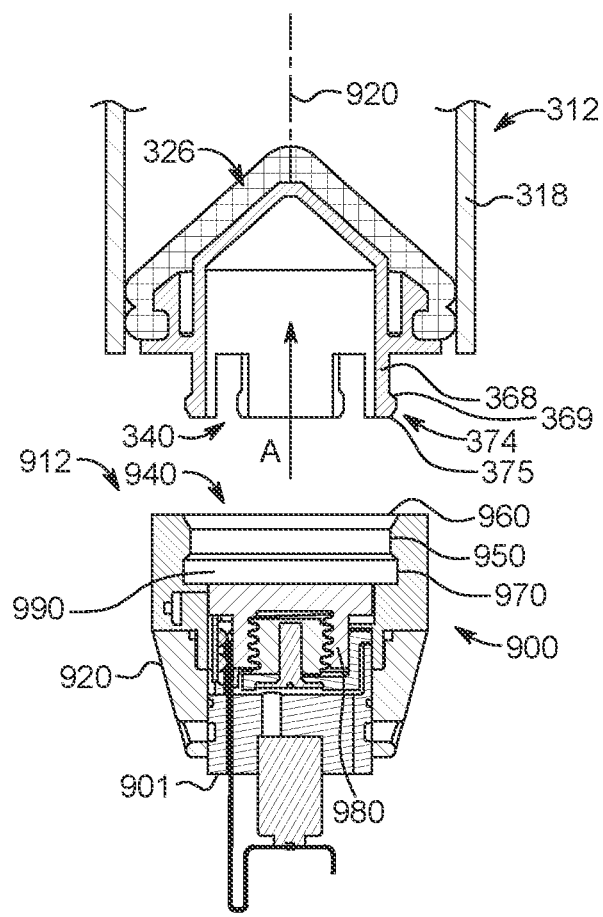
FIGS. 23A-23G are cross-sectional views of a piston of the operation of a plunger engagement mechanism according to another embodiment of the present disclosure.

With reference to FIG. 23A, the plunger 326 has at least one retaining member 368 with a catch 374 that protrudes radially outward relative to the plunger longitudinal axis 334. The catch 374 is shaped to be received within at least a portion of the piston engagement mechanism 912. In some embodiments, the catch 374 has a rounded or an angled catch surface 375 that is angled at an acute or obtuse angle relative to the plunger longitudinal axis 334. The angled catch surface 375 is configured to interact with at least a portion of the plunger engagement mechanism 912 during engagement of the plunger 326 with the piston 900, as described herein. The at least one retaining member 368 may also have at least rounded or one angled release surface 369.

The angled release surface 369 may be provided on at least a portion of the catch 374, such as opposite of the angled catch surface 375. The rounded or angled release surface 369 is angled at an acute or obtuse angle relative to the plunger longitudinal axis 334 in a direction opposite to the arc or angle of the rounded or angled catch surface 375. The rounded or angled release surface 369 is configured to interact with at least a portion of the plunger engagement mechanism 912 during disengagement of the plunger 326 from the piston 900, as described herein. In various embodiments, the frictional and locking interaction between the rounded or angled release surface 369b, without additional support, is insufficient to lockably engage the plunger 326 with the plunger engagement mechanism 912 of piston 900.

Piston 900 is extendible and retractable from the housing of the fluid injector 10, 100 (FIGS. 1 and 3). The piston 900 includes a stem 901 and a piston head 920 formed on a distal end of the stem 900. In certain embodiments, piston head 920 may extend radially outwardly beyond the radial edge of the stem 900. The piston head 920 may be substantially cylindrical in structure with a piston cavity 940 configured for receiving at least a portion of the plunger 326 such as the at least one retaining member 368 when the plunger 326 is connected with the piston 900. The piston cavity 940 may have at least one locking lip 950 protruding radially inward from an inner surface of the piston cavity 940. The at least one locking lip 950 is configured for engaging at least a portion of the retaining member 368, such as the catch 374. The at least one locking lip 950 may be continuous or discontinuous in a circumferential direction around the piston cavity 940.

In some examples, the at least one locking lip 950 has a rounded or angled distal surface 960 and a rounded or angled proximal surface 970. The rounded or angled distal surface 960 is arced or angled in a same direction as the rounded or angled catch surface 375 of the plunger 326. In this manner, the distal surface 960 engages the catch surface 375 during the connection process between the piston 900 and the plunger 326 to flexibly and resiliently deflect the one or more retaining members 368 in a radially inward direction toward the plunger longitudinal axis 334 to allow the plunger 326 to be inserted into the piston cavity 940. The rounded or angled proximal surface 970 is arced or angled in an opposite direction to the rounded angled distal surface 960. The rounded or angled proximal surface 970 is arced or angled in a same direction as the rounded or angled release surface 369 of the plunger 326. In this manner, the proximal surface 970 engages the release surface 369 when the piston 900 and/or the plunger 326 is moved axially to disconnect the plunger 326 from the piston 900. The engagement between the release surface 369 on the plunger 326 and the proximal surface 970 on piston 900 deflects the one or more retaining members 368 in a radially inward direction toward longitudinal axis 334 to allow plunger 326 to be withdrawn from piston cavity 940.

Figure 23B:
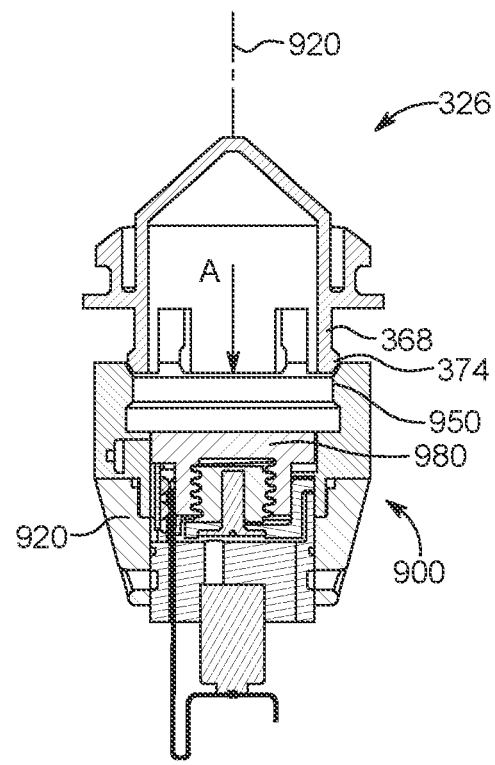
Figure 23C:
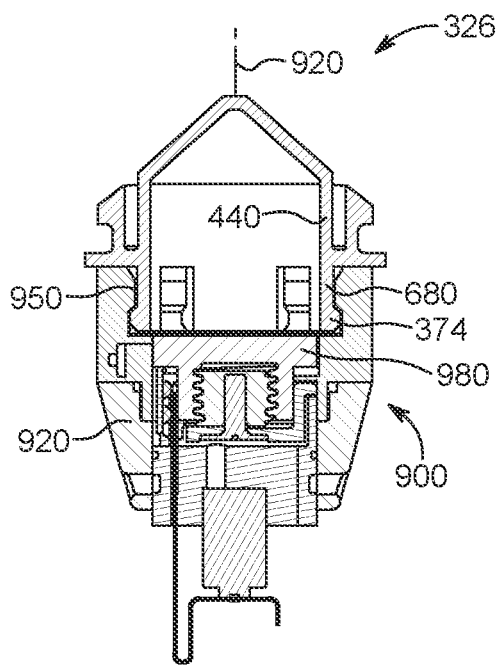
Figure 23D:
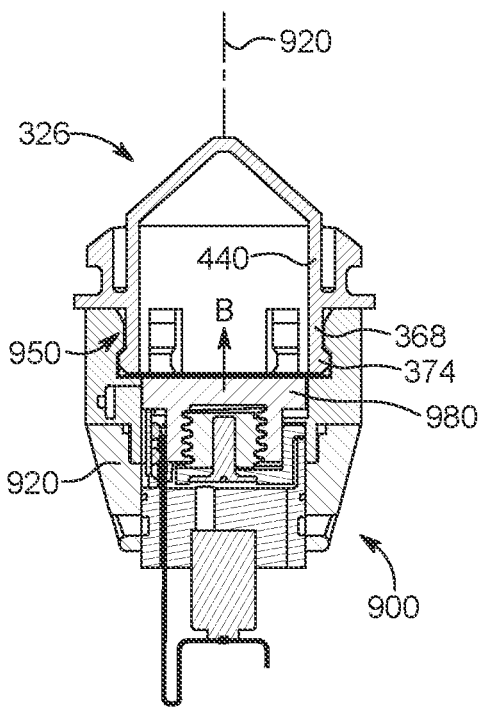
Figure 23E:
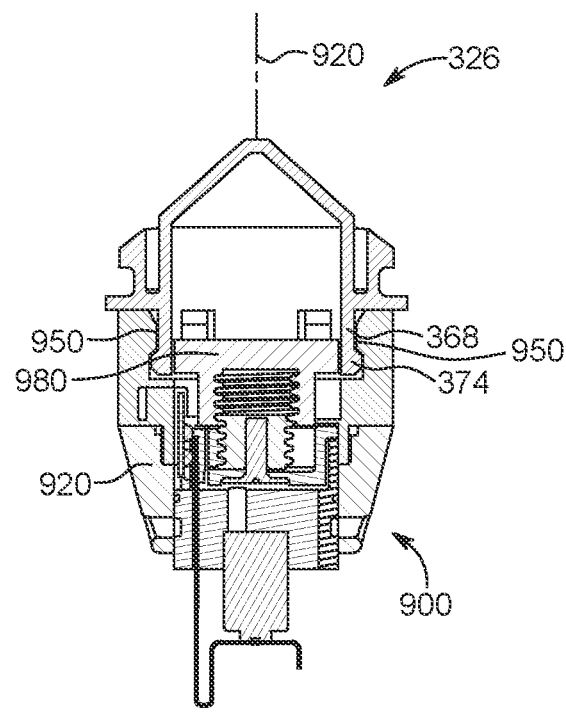

With reference to FIGS. 23A-23G, the piston 900 has a locking member 980 configured for locking the plunger 326 relative to the piston 900. The locking member 980 may be movable axially between a first position (FIG. 23D) and a second position (FIG. 23E). In some examples, the locking member 980 is movable such that it extends at least partially within the piston cavity 940. When extended in the second position, the locking member 980 is inserted into the cavity 340 of the plunger 326 to prevent deflection of the at least one retaining member 368 in a radially inward direction. For example, in the second, engaged position, locking member 980 locks the catch 374 against the at least one locking lip 950 by holding release surface 369 on the plunger 326 against the proximal surface 970 on the piston 900 such that the catch 374 cannot move past the at least one locking lip 950. In some embodiments, a sensing member (not shown), such as a spring-loaded pin connected to a sensor, may be provided for sensing contact with a surface, such as a surface of the plunger 326, and control a movement of the piston 900 based on the sensed condition.

Having described the structure of the plunger 326 and the piston 900 in accordance with one non-limiting embodiment, the engagement and disengagement of the plunger 326 with and from the piston 900 will now be described with reference to FIGS. 23A-23G. The syringe 12, shown in FIG. 23A is omitted from the remainder of FIGS. 23B-23G for clarity.

To engage the plunger 326 with the piston 900, the syringe 12 is first inserted into the syringe port 16 of the fluid injector 10 (FIG. 1) or pressure jacket 15 (FIG. 3). Once the syringe 12 is inserted into the syringe port 16, various locking mechanisms (not shown) may be used to retain the syringe 12 within the syringe port 16 or within a pressure jacket to prevent detachment of the syringe 12 from the syringe port 16. Initially, the plunger 326 may be positioned at the proximal end 20 of the syringe barrel 18. The piston 900 may then be advanced distally toward the plunger 326 for engagement of the piston head 920 with the plunger 326.

With reference to FIGS. 23A-23B, the piston 900 is advanced axially in a distal direction (arrow A in FIGS. 23A-23B) such that the angled distal surface 960 of the piston head 920 contacts the at least one retaining member 368 of the plunger 326. Initially, the angled distal surface 960 contacts the catch 374, such as the catch surface 375, of the at least one retaining member 368. Because the catch 374 protrudes radially outward relative to the at least one retaining member 368, the catch 374 is positioned at a greater radial distance from the plunger longitudinal axis 334 than the inner surface of the piston cavity 940 proximate to the angled distal surface 960. In this manner, continued distal movement of the piston 900 causes the at least one retaining member 368 to be flexibly and resiliently deflected radially inward due to the contact between the catch surface 375 on the plunger 326 and the distal surface 960 on the piston 900 (FIG. 23B). In examples with a plurality of retaining members 368, each of retaining members 368 is deflected radially inward relative to plunger longitudinal axis 334.

With reference to FIGS. 23C, during continued axial movement of the piston 900 in a distal direction, the catch 374 is advanced axially past the at least one lip 950 of the piston head 920. Due to a restoring force created during a radial deflection of the flexible at least one retaining member 368, the catch 374 is snapped radially outward into a recess 990 positioned proximally of the at least one locking lip 950 (FIG. 23A). The plunger 326 is thus releasably retained within the piston cavity 940. To lock the plunger 326 with the piston 900 and prevent removal of the plunger 326 from the piston 900, the locking member 980 is extended from the first position (FIG. 23D) to a second position (FIG. 23E) by moving the locking member 980 in the axial direction (arrow B). In the second position, the locking member 980 is positioned such that the retaining members 368 are locked between an inner surface of the piston cavity 940 and an outer surface of the locking member 980 and are unable to flexibly deflect inwardly to disengage. The locking member 980 prevents the retaining members 368 from moving in a radially inward direction, thereby preventing the plunger 326 from being disconnected from the piston 900. In this manner, the piston 900 can be moved in a proximal or distal direction, which results in a corresponding movement of the plunger 326. Locking member 980 may be moved between the disengaged and engaged positions by an electromechanical actuator, such as a solenoid actuator, a rotary motor, a linear motor, and the like. As shown in FIGS. 23A-23B, the locking member 980 may be reciprocally moved using a rotary motor to rotate intermeshed surfaces of a threaded, screw drive.

Figure 23F:
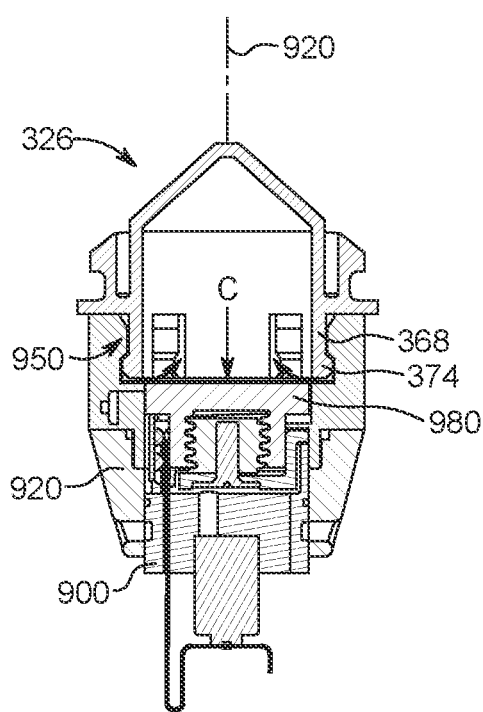
Figure 23G:
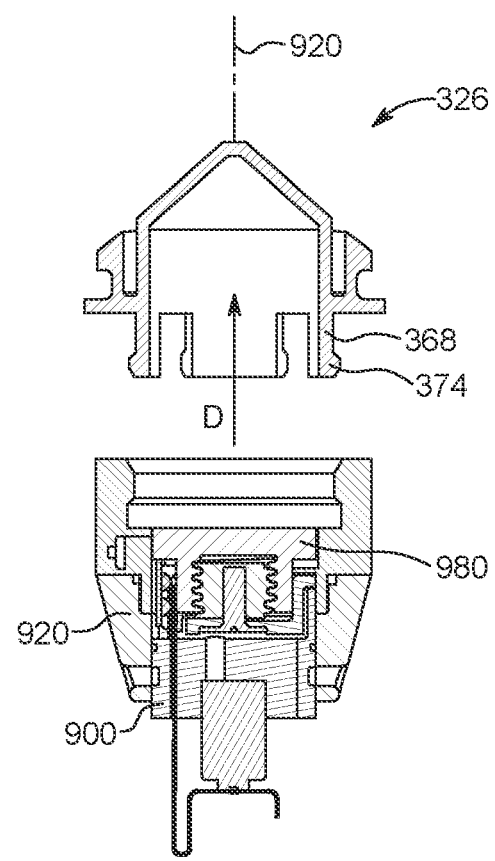

To unlock the syringe 12 from the syringe port 16 and disengage the plunger 326 from the piston 900, the locking member 980 is moved from the second position to the first position by moving axially in a direction of arrow C shown in FIG. 23F. With the locking member 980 in the first position, the plunger 326 can be disconnected from the piston 900 by moving the plunger 326, via the syringe 12, in a distal direction (arrow D in FIG. 23G) and/or moving the piston 900 in a proximal direction. Such relative movement between the piston 900 and the plunger 326 causes the angled release surface 369 of the retaining members 368 to engage the angled proximal surface 970 of the piston 900. Continued movement of the plunger 326 apart from the piston 900 causes the retaining members 368 to be deflected radially inward in order to clear the lip 950. After clearing the lip 950, retaining members 368 spring back in a radially outward direction, whereby plunger 326 is completely disengaged from piston 900.

Figure 24A:
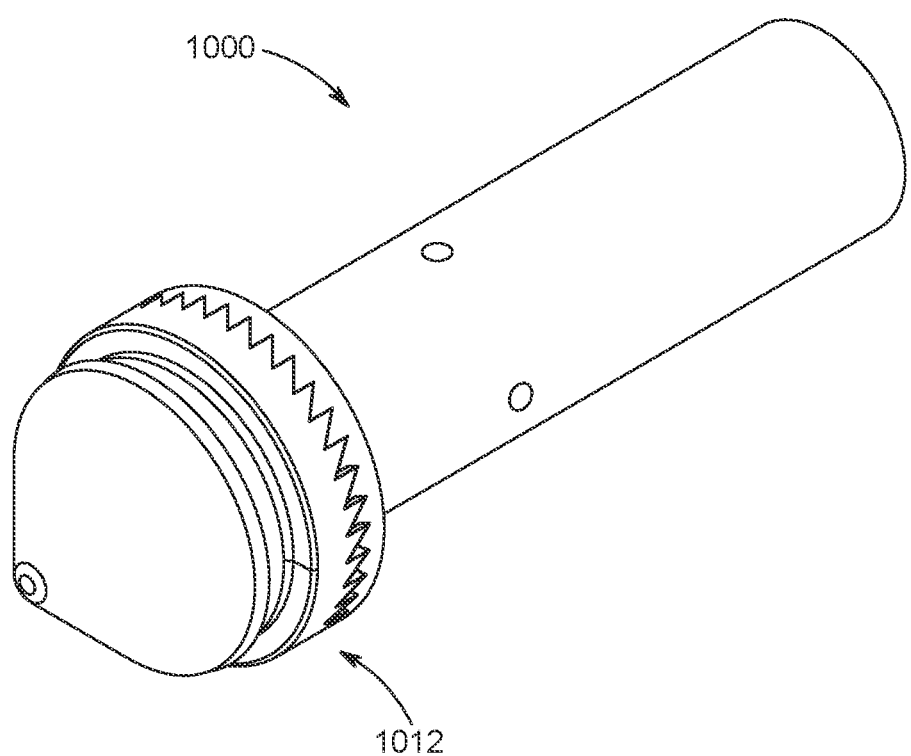
FIG. 24A is a perspective view of a piston having a plunger engagement mechanism according to another embodiment of the present disclosure.
Figure 24B:
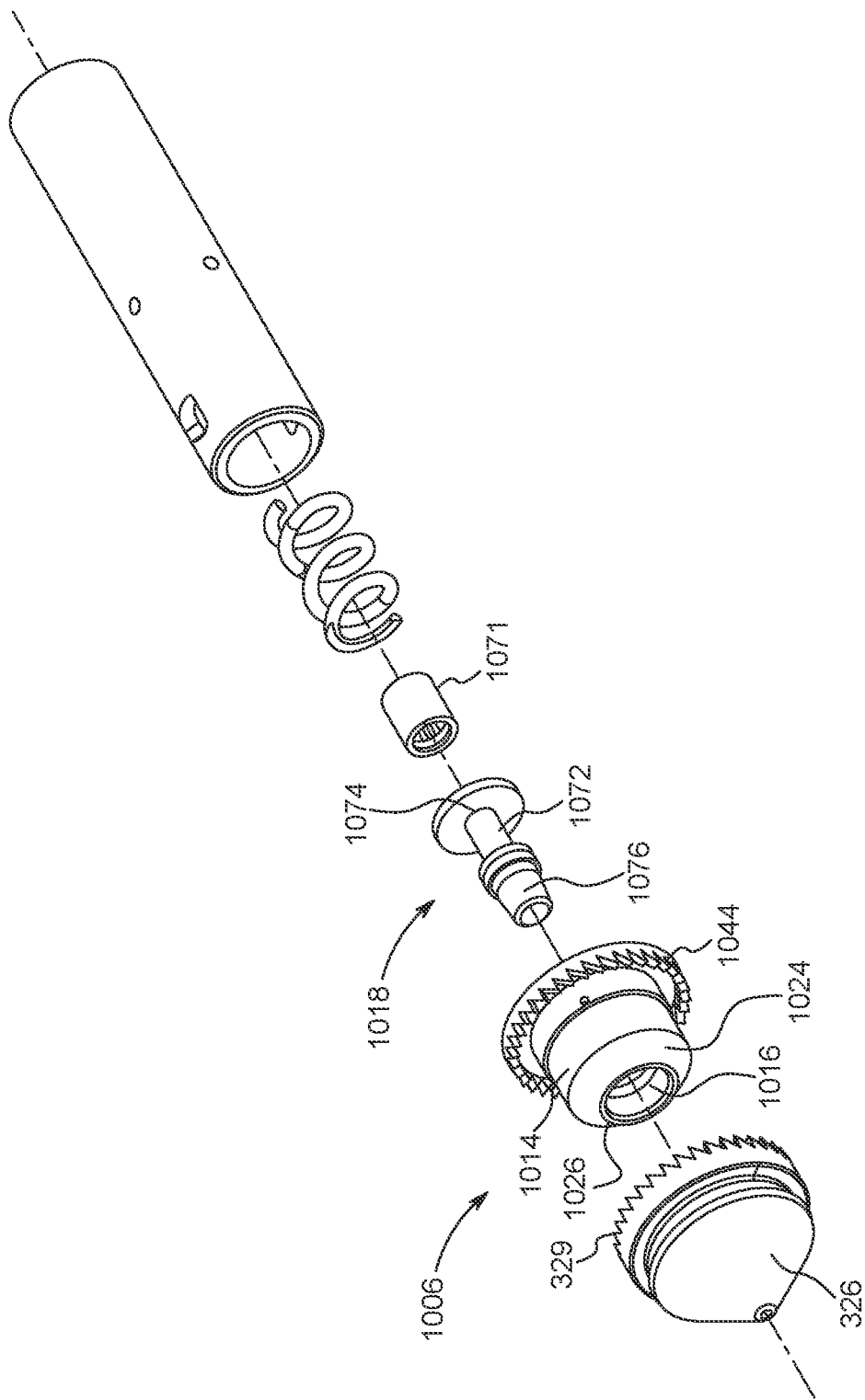
FIG. 24B is an exploded view of the plunger engagement mechanism of FIG. 24A.
Figure 24C:
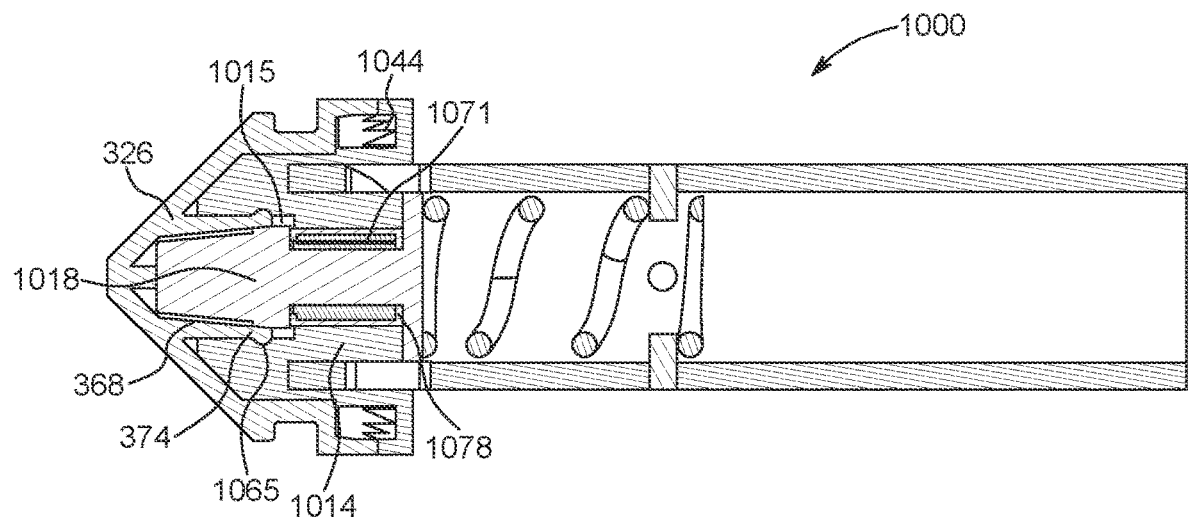
FIG. 24C is a cross-sectional view of the piston and plunger engagement mechanism of FIG. 24A.

With reference to FIGS. 24A-24C, a piston 1000 and a plunger engagement mechanism 1012 are shown in accordance with another embodiment of the present disclosure. The components of the piston 1000 and the plunger engagement mechanism 1012 shown in FIGS. 24A-24C are substantially similar or identical to the components of the piston 400 and the plunger engagement mechanism 412 described herein with reference to FIGS. 9-13J. Accordingly, reference numerals in FIGS. 24A-24C are used to illustrate identical components of the corresponding reference numerals in FIGS. 9-13J, with the exception that the leading number in reference numbers used in FIGS. 24A-24C has been changed from a "4" to a "10". As the previous discussion regarding the piston 400 and the plunger engagement mechanism 412 generally shown in FIGS. 9-13J is applicable to the piston 1000 and the plunger engagement mechanism 1012 shown in FIGS. 24A-24C, only the relative differences between the components shown in these figures are discussed hereinafter.

With reference to FIG. 24B, the plunger engagement mechanism 1012 has a plunger engagement sleeve 1014 having a central opening 1016 and a plunger engagement post 1018 that is reciprocally movable within the central opening 1016 of the plunger engagement sleeve 1014 along a direction of a longitudinal piston axis 1020. The plunger engagement post 1018 is reciprocally driven by an actuator, such as an actuator 422 shown in described herein with reference to FIG. 9 or the other embodiments of the plunger engagement mechanism described herein. The plunger engagement mechanism 1012 is operable between an engaged position or state, and a disengaged position or state. In the engaged position or state, the plunger engagement post 1018 may be positioned within the plunger engagement sleeve 1014 to capture at least one retaining member 368 associated with the plunger 326 in a receiving space 615 between the plunger engagement sleeve 1014 and the plunger engagement post 1018 (shown in FIG. 24C). Conversely, in the disengaged position or state, the plunger engagement post 1018 may be positioned relative to the plunger engagement sleeve 1014 to permit removal of the at least one retaining member 368 associated with the plunger 326 from the receiving space 1015 between the plunger engagement sleeve 1014 and plunger engagement post 1018.

With reference to FIG. 24B, plunger engagement sleeve 1014 has a hollow body 1024, wherein at least a portion of an outer surface of the hollow body 1024 defines at least a portion of the piston head 1006. A distal portion or end 1026 of the plunger engagement sleeve 1014 is shaped to be received within the interior cavity 340 of the plunger 326, while at least a portion of the plunger 326, such as the at least one retaining member 368, is configured to be received within the central opening 1016. The central opening 1016 extends through the hollow body 1024 of the plunger engagement sleeve 1014. An outer surface 1042 of the plunger engagement sleeve 1014 may have a toothed portion 1044. The toothed portion 1044 may be configured for interacting with a corresponding toothed portion 329 on the plunger 326 during rotation of the plunger 326 relative to the piston 1000.

The plunger engagement sleeve 1014 further includes at least one locking groove 1065 recessed into the inner surface of the central opening 1016. In some embodiments, the at least one groove 1065 may be configured to receive a catch 374 of the at least one retaining member 368 of the plunger 326 when the plunger 326 is connected to the plunger engagement sleeve 1014.

The plunger engagement post 1018 has a shaft 1072 having a proximal end 1074 and a distal end 1076. The distal end 1076 of the shaft 1072 has a tapered end surface 1078 configured for contacting the at least one retaining member 368 on the plunger 326 to flexibly deflect the at least one retaining member 368 in a radially inward direction as the piston 1000 contacts the plunger 326. When moved into the engaged position, the plunger engagement post 1018 prevents removal of the plunger 326 from the piston 1000 (shown in FIG. 24C), for example by locking catch 374 of the at least one retaining member 368 of the plunger 326 under locking groove 1065 on the plunger engagement sleeve 1014. The proximal end 1074 of the shaft 1072 is configured for connecting to an actuator, similar to the actuator 422 described herein with reference to FIGS. 9-13J for moving the plunger engagement post 1018 relative to the plunger engagement sleeve 1014 between an engaged position or state and a disengaged position or state.

With reference to FIG. 24C, the proximal end 1074 of the shaft 1072 is received within a rotating mechanism 1071 that is slidably mounted within the hollow body 1024 of the plunger engagement sleeve 1014. In some embodiments, the rotating mechanism 1071 may be configured for one-way rotation, such as in a clockwise or a counter-clockwise direction about the longitudinal piston axis 1020 as described according to various embodiments herein. For example, the rotating mechanism 1071 may be a one-way clutch.

Having described the structure of the plunger 326 and the piston 1000 in accordance with one non-limiting embodiment of the present disclosure, a method of engagement and disengagement of the plunger 326 with and from the piston 1000 will now be described.

FIG. 24C shows the piston 1000 with its plunger engagement mechanism 1012 in an engaged position or state with the plunger 326. As described herein with reference to FIGS. 13A-13J, the plunger 326 can be connected to the piston 1000 by moving the piston 1000 distally to permit insertion of the one or more retaining members 368 of the plunger 326 into the receiving space 1015 between the plunger engagement sleeve 1014 and the plunger engagement post 1018 such that the catch 374 is within the locking groove 1065. In some embodiments, the piston 1000 may be advanced distally using the drive mechanism 402 operated by the controller 200 (FIG. 2). In other embodiments, the piston 1000 can be manually moved in the distal direction.

The piston 1000 is advanced axially in a distal direction such that the at least one retaining member 368 of the plunger 326 is received within the central opening 1016 of the plunger engagement sleeve 1014 such that the at least one retaining member 368 is deflected radially inward due to the contact between the catch 374 and the inner surface of the plunger engagement sleeve 1014. In embodiments having a plurality of retaining members 368, each of the retaining members 368 is deflected in the radially inward direction.

During continued axial movement of the piston 1000 in a distal direction, the catch 374 is deflected radially outward into the locking groove 1065 of the piston engagement sleeve 1014. After the catch 374 is positioned within the locking groove 1065, distal movement of the piston 1000 relative to the plunger 326 is stopped, such as due to engagement between the toothed portion 329 on the plunger 326 with the toothed portion 1044 on the outer surface 1042 of the plunger engagement sleeve 1014. The plunger engagement post 1018 is in the disengaged position or state and the plunger 326 connected to the piston 1000, the toothed portion 329 on the plunger 326 is aligned with the toothed portion 1044 on the outer surface 1042 of the plunger engagement sleeve 1014.

With movement of the plunger engagement post 1018 from the disengaged state or position to the engaged state or position, the receiving space 1015 between the plunger engagement sleeve 1014 and the plunger engagement post 1018 is closed to prevent removal of the one or more retaining members 368 of the plunger 326 from the receiving space 1015 and the locking groove 1065. As the plunger engagement post 1018 is moved to the engaged position or state, the at least one retaining member 368 of the plunger 326 is captured between the plunger engagement sleeve 1014 and the outer surface of the plunger engagement post 418. The piston 1000 and the connected plunger 326 may then be moved reciprocally within the barrel 318 of the syringe 300. In some embodiments, the piston 1000 may be advanced distally to deliver the fluid from the syringe 300 or proximally to fill the syringe 300 with fluid using the drive mechanism 402 operated by the controller 200 (FIG. 2).

To unlock the syringe 300 from the syringe port of the injector and disengage the plunger 326 from the piston 1000, the syringe 300 is rotated clockwise or counter-clockwise about the syringe longitudinal axis, relative to the syringe port. Due to alignment of the toothed portion 329 on the plunger 326 with the toothed portion 1044 on the plunger engagement sleeve 1014, rotation of the plunger 326 also rotates the plunger engagement sleeve 1014. Because the plunger engagement post 1018 is connected to the plunger engagement sleeve 1014 via the rotating mechanism 1071, the plunger engagement post 1018 does not rotate with rotation of the plunger engagement sleeve 1014. In some embodiments, the plunger engagement post 1018 may be movable between an engaged position and a disengaged position via an actuator, such as an actuator 424 described herein with reference to FIGS. 9-13J.

Figure 25A:
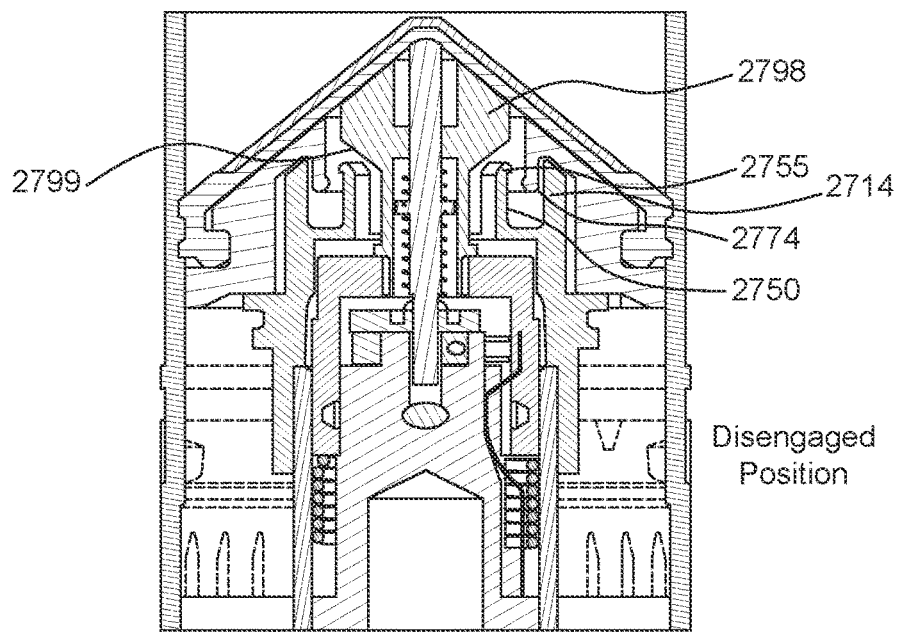
FIGS. 25A-25B are cross-sectional views of a piston of the operation of plunger engagement mechanism according to another embodiment of the present disclosure.
Figure 25B:
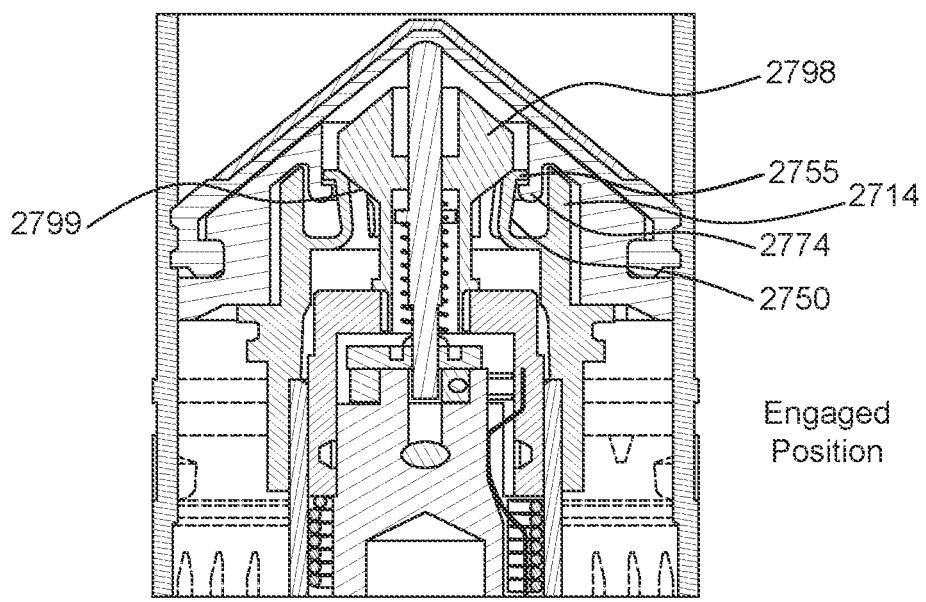

FIGS. 25A and 25B illustrate embodiments of a piston-plunger engagement system according to another embodiment. FIG. 25A shows the system in a disengaged position where the plunger comprises an inwardly facing engagement flange or catch 2774 extending proximally from an inner surface of a plunger base. The piston includes at least one flexible retaining member 2750 having at least one retaining catch 2755 configured for engaging the corresponding engagement flange or catch 2774 of the plunger base. In the disengaged position, movable locking member 2798 is configured in the distal, first position such that the locking member 2798 is not engaged with the at least one flexible retaining member 2750 of the piston 2700. As shown in FIG. 25B, the piston-plunger engagement system is in the engaged position, where movable locking member 2798 is moved in the proximal direction, for example by a motor, solenoid, or cam system. As locking member 2798 moves proximally, a proximal surface 2799, for example the angled surface illustrated in FIGS. 25A and 25B contacts and engages the at least one flexible retaining member 2750 flexing the retaining member 2750 in a radially outward direction. As the retaining member 2750 moves radially outward, the at least one retaining catch 2755 engages the at least one inwardly facing engagement flange or catch 2774, locking the plunger base to the piston. Generally, the at least one inwardly facing engagement flange or catch 2774 is substantially inflexible, for example due to structural strength or the outer surface of plunger engagement sleeve 2714 that prevents engagement flange or catch 2774 from flexing radially outward and disengaging from the at least one retaining catch 2755 of the at least one flexible retaining member 2750. Moving the locking member 2798 in the distal direction releases the force applied to the at least one flexible retaining member 2750 allowing the retaining member 2750 to return to the non-flexed, disengaged position, where the at least one retaining catch 2755 does not contact or engage the at least one inwardly facing engagement flange or catch 2774 and allows the plunger to be removed from the piston.

In some embodiments, a resiliently elastic member 2784 may be configured for biasing the locking member 2798 toward the disengaged position or the engaged position. For example, the resiliently elastic member 2784 may be a compression spring that is configured for biasing the locking member 2798 in a distal direction toward the disengaged position. In this manner, the locking member 2798 is in a normally-disengaged state such that, in the event of a power loss, the plunger can be disconnected from the locking member 2798. In other embodiments, the resiliently elastic member 2784 may be an extension spring that is configured for biasing the locking member 2798 in a proximal direction toward the engaged position. In such embodiments, the locking member 2798 is in a normally-engaged position and must be moved to the disengaged position, such as using an actuator 422 described herein with reference to FIG. 9 to permit removal of the plunger from the locking member 2798.

Figure 26:
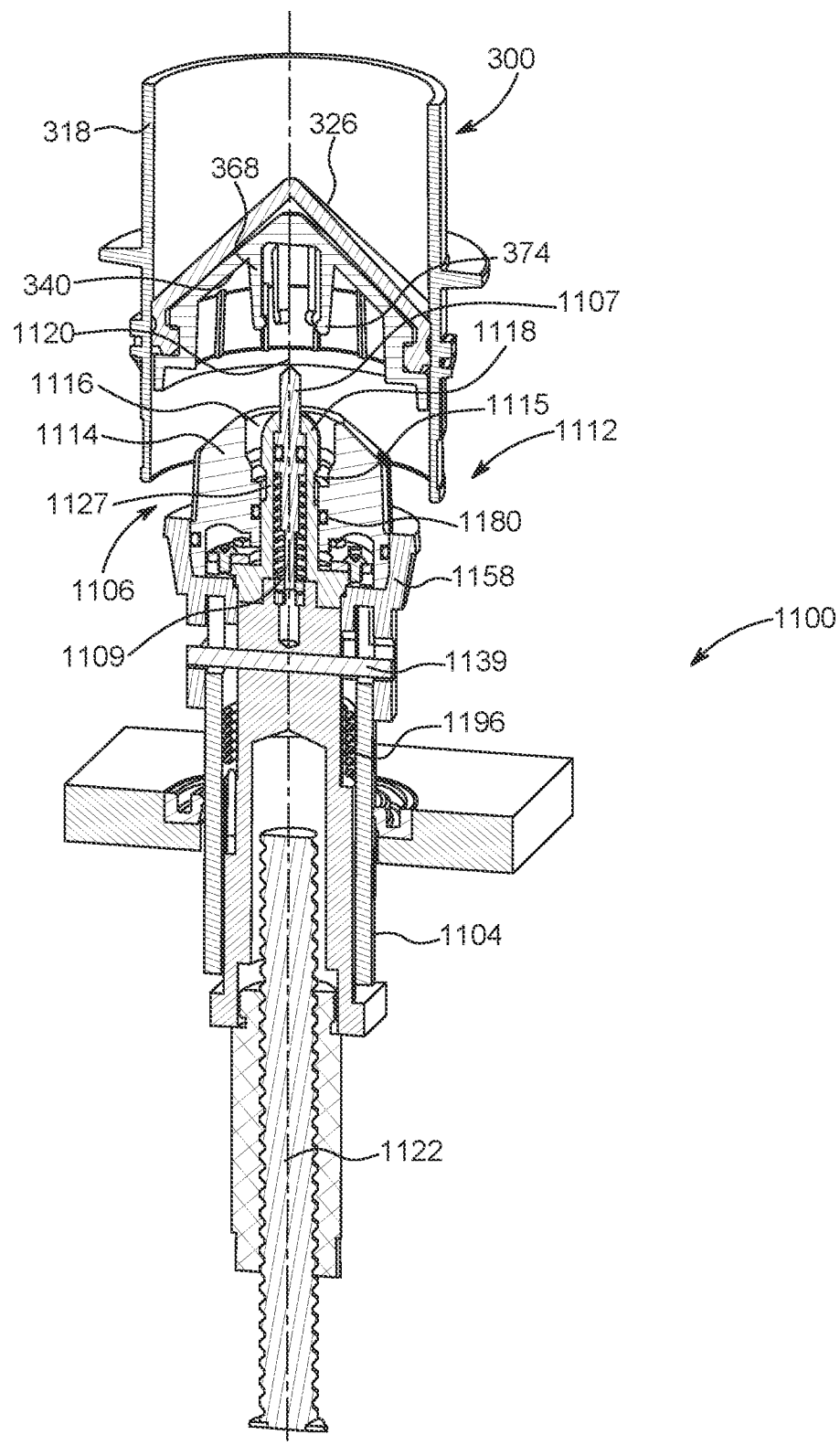
FIG. 26 is a perspective cross-sectional view of a piston of a fluid injector system having a plunger engagement mechanism according to another embodiment of the present disclosure.

Referring to FIG. 26, a piston 1100 having a plunger engagement mechanism 1112 is shown in accordance with another embodiment of the present disclosure. In some embodiments, the piston 1100 may be configured for use with injectors 10, 100 shown in FIGS. 1 and 3. In other embodiments, the piston 1100 may be configured for use with any fluid injector configured for medical use such as injection of contrast and saline in a contrast enhanced imaging procedure. The piston 1100 is configured for reciprocal movement within the housing of the injector via a drive mechanism. The drive mechanism may include, for example, an electric motor 402 (FIG. 2), hydraulic system, a pneumatic system, or any combination thereof. The controller 200 (FIG. 2) may be configured for controlling operation of the drive mechanism and, in turn, controlling reciprocal movement of the piston 1100.

The piston 1100 has a body 1104 and a piston head 1106 at a distal end of the body 1104. The piston head 1106 is configured for removably connecting to the plunger 326 of the syringe 300. The piston head 1106 has a substantially cylindrical structure with a partially conical distal end configured to be received inside at least a portion of the interior cavity 340 of the plunger 326. In some embodiments, at least a portion of the piston head 1106 and/or plunger 326 may be made from a transparent or translucent material that is configured to permit a passage of light emitted by one or more lights in the piston 1100 for illuminating at least a portion of the plunger 326 and/or the syringe 300.

Piston head 1106 has a plunger engagement mechanism 1112 configured for releasably engaging the plunger 326 to facilitate reciprocally driving the plunger 326 within the barrel of the syringe 300 and ready removal of syringe 300 and plunger 326 from the piston head 1106 and fluid injector at the end of an injection procedure. The plunger engagement mechanism 1112 has a plunger engagement sleeve 1114 having a central opening 1116 and a plunger engagement post 1118 that is reciprocally movable within the central opening 1116 of the plunger engagement sleeve 1114 along a direction of a longitudinal piston axis 1120. The plunger engagement post 1118 is reciprocally driven by an actuator 1122 of the fluid injector. The plunger engagement mechanism 1112 is operable between an engaged position or state, and a disengaged position or state. In the engaged position or state, the plunger engagement post 1118 may be positioned within the plunger engagement sleeve 1114 to capture at least one retaining member 368 associated with the plunger 326 in a receiving space 1115 between the plunger engagement sleeve 1114 and the plunger engagement post 1118. Conversely, in the disengaged position or state, the plunger engagement post 1118 may be positioned relative to the plunger engagement sleeve 1114 to permit removal of the at least one retaining member 368 associated with the plunger 1100 from the receiving space 1115 between the plunger engagement sleeve 1114 and the plunger engagement post 1118.

The actuator 1122 may be configured for having an engaged state for moving one of the plunger engagement sleeve 1118 and the plunger engagement post 1118 to the engaged position and a disengaged state for moving one of the plunger engagement sleeve and the plunger engagement post to the disengaged position. In some embodiments, the actuator 1122 may be automatically moved to the disengaged state, such as during power loss to the actuator 1122. In some embodiments, the actuator 1122 may be in the engaged state only during proximal movement of the piston 1100. In some embodiments, the actuator 1122 may be a solenoid configured to be predominantly in the disengaged state and may be in the engaged state only during connection of the plunger 326 to the piston 1100. In other embodiments, the actuator 1122 may be a rotary electric motor, a linear electric motor, or a linear actuator. In some embodiments, the actuator 1122 is a linear actuator that can be back driven manually in the event of a power loss to the injector. In various embodiments, moving one of the plunger engagement sleeve 1118 and the plunger engagement post 1118 to the disengaged state for removal of the plunger 326 from piston 1100 may be accomplished by rotation of the plunger 326 relative to the piston 1100 as described herein.

Figure 27A:
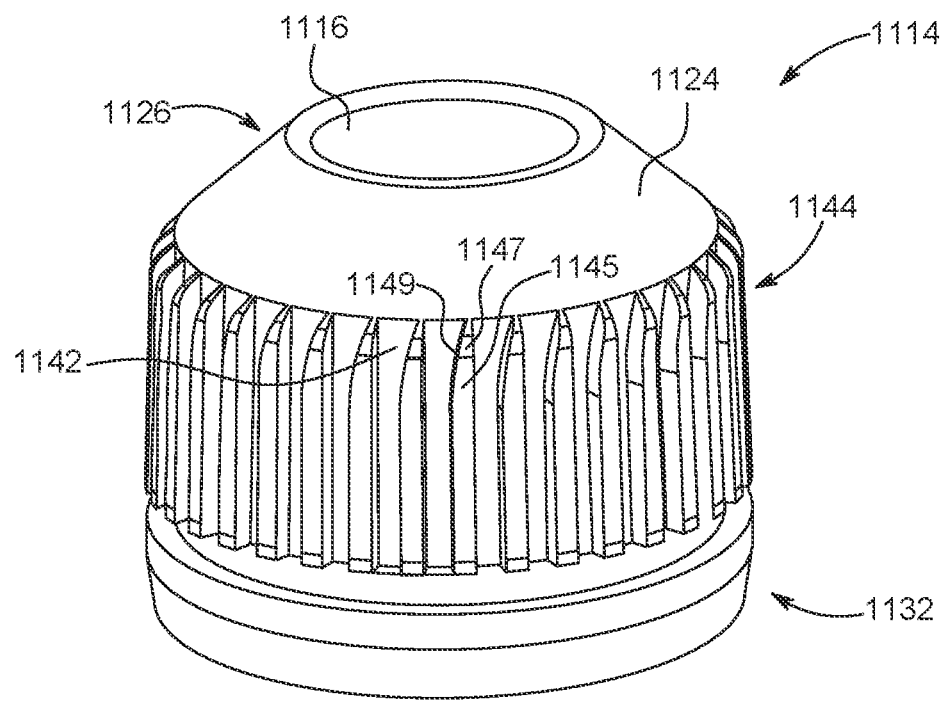
FIG. 27A-27B are a perspective view (FIG. 27A) and a perspective cross-sectional view (FIG. 27B) of a plunger engagement sleeve of the plunger engagement mechanism of FIG. 26.

With reference to FIG. 27A, a plunger engagement sleeve 1114 according to an embodiment is described. The plunger engagement sleeve 1114 has a hollow body 1124, wherein at least a portion of an outer surface of the hollow body 1124 defines at least a portion of the piston head 1106 (FIG. 26). In some embodiments, a distal portion or end 1126 of the hollow body 1124 may have a conical shape configured to correspond to the shape of interior cavity 340 of the conical-shaped portion of the plunger 326. At least a portion of the plunger 326, such as the at least one retaining member 368, is configured to be received within the central opening 1116. The central opening 1116 extends through the hollow body 1124 of the plunger engagement sleeve 1114. A proximal end or portion 1132 of the hollow body 1124 may be configured to be received within a plunger release sleeve 1158 (shown in FIG. 28).

At least a portion of an outer surface 1142 of the hollow body 1124 has a toothed portion 1144 that is configured for interacting with one or more release tabs 380 on the plunger 326 during attachment and removal of the plunger 326 from the plunger engagement mechanism 1112, as described herein. The toothed portion 1144 has one or more plunger release teeth 1145 protruding from the outer surface 1142. The one or more plunger release teeth 1145 may protrude radially outward from the outer surface 1142 of the hollow body 1124. The one or more plunger release teeth 1145 are separated from each other by portions of the outer surface 1142 of the hollow body 1124 such that grooves are formed between adjacent plunger release teeth 1145. In embodiments where more than two plunger release teeth 1145 are provided, the plunger release teeth 1145 may be evenly spaced apart from each other. In some embodiments, the plunger release teeth 1145 may have unequal angular extension and/or unequal angular spacing. The radial spacing of the plunger release teeth 1145 may be selected to correspond to the spacing between the one or more release tabs 380 on the plunger 326. A distal end 1147 of each of the plunger release teeth 1145 may have a pointed end 1149 that is configured for self-oriented guiding the one or more release tabs 380 on the plunger 326 during connection of the plunger 326 to the plunger engagement sleeve 1114. As described herein, the one or more plunger release teeth 1145 are configured for interacting with one or more release tabs 380 on the plunger 326 to effect a release of the plunger 326 from the piston upon rotation of the plunger 326 about its longitudinal axis 334, such as due to rotation of the syringe 300.

Figure 27B:
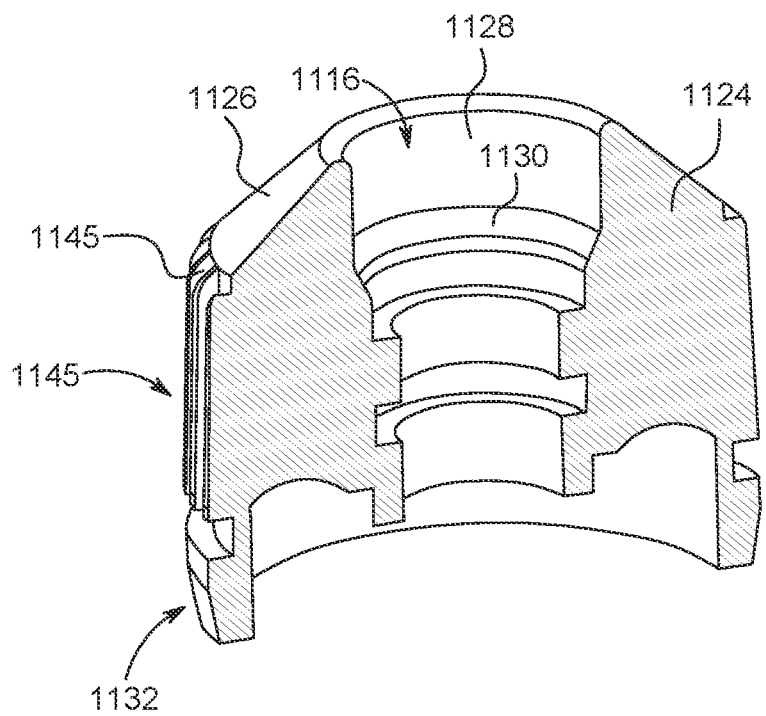

With reference to FIG. 27B, a portion of an inner surface 1128 of the central opening 1116 at the distal end of the opening 1116 may have a ramp 1130 such that an inner diameter of the opening 1116 narrows in a direction from the distal end 1126 of the hollow body 1124 toward a proximal portion or end 1132. in some embodiments, the ramp 1130 may be configured for deflecting at least a portion of the at least one retaining member 368 associated with the plunger 326 in a radially inward direction during connection of the plunger 326 to the distal portion or end 1126 of the plunger engagement sleeve 1114. In other embodiments, the ramp 1130 may define a clearance space for at least a portion of the at least one retaining member 368, such as the catch 374, during connection of the plunger 326 to the plunger engagement sleeve 1114. The inner surface 1128 of the central opening 1116 may have a ramped inner diameter that decreases in a direction from a distal end 1126 of the plunger engagement sleeve 1114 towards the proximal end of the plunger engagement sleeve 1114. For example, the opening 1116 may have a first inner diameter proximally of the ramp 1130 and a second diameter that is smaller than the first diameter distally of the ramp 1130. The inner surface 1128 of the central opening 1116 may be substantially cylindrical proximally of the ramp 1130. In other embodiments, one or both portions of the inner surface 1128 before and after ramp 1130 may have a slight incline angled in the same direction as ramp 1130.

Figure 28:
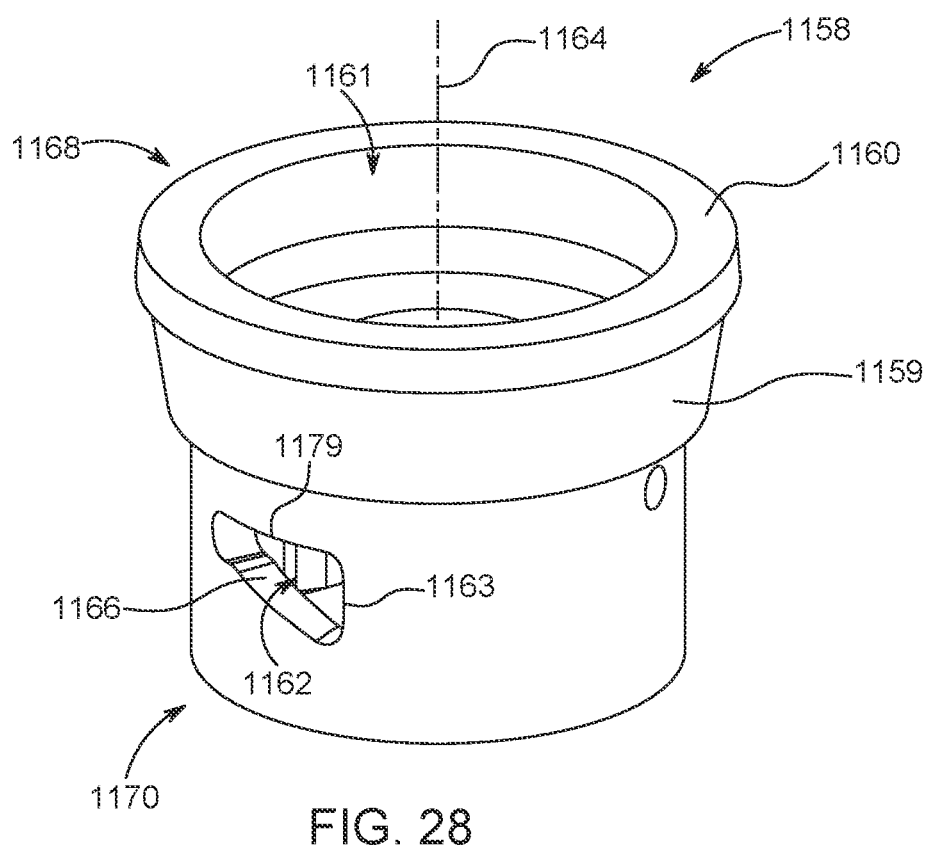
FIG. 28 is a perspective view of a plunger release sleeve of the plunger engagement mechanism of FIG. 26.

With reference to FIGS. 26 and 28, a plunger release sleeve 1158 surrounds at least a portion of the plunger engagement sleeve 1114. In some embodiments, the plunger release sleeve 1158 has a hollow body 1159 having an inner cavity 1161 configured for receiving the proximal end or portion 1132 of the plunger engagement sleeve 1114. In some embodiments, the plunger release sleeve 1158 has a cylindrical sidewall 1160 having an opening 1162 extending therethrough. The opening 1162 may have a longitudinal surface 1163 that is substantially parallel with a longitudinal axis 1164 of the plunger release sleeve 1158 and a ramped surface 1166 that is contiguous with the longitudinal surface 463 and is angled downward relative to the longitudinal axis 1164 of the plunger release sleeve 1158 in a direction from a distal end 1168 toward a proximal end 1170. As described herein, the longitudinal surface 1163 is configured to guide a guiding pin 1139 associated with the plunger engagement post 1118 during movement of the plunger engagement post 1118 in a longitudinal direction along the longitudinal axis 1120 of the piston 1100, while the ramped surface 1164 is configured to guide the guiding pin 1139 to move the plunger engagement post 1118 during rotational movement of the plunger 326 relative to the piston 1100, such as during removal of the plunger 326 from the piston 1100.

Figure 29:
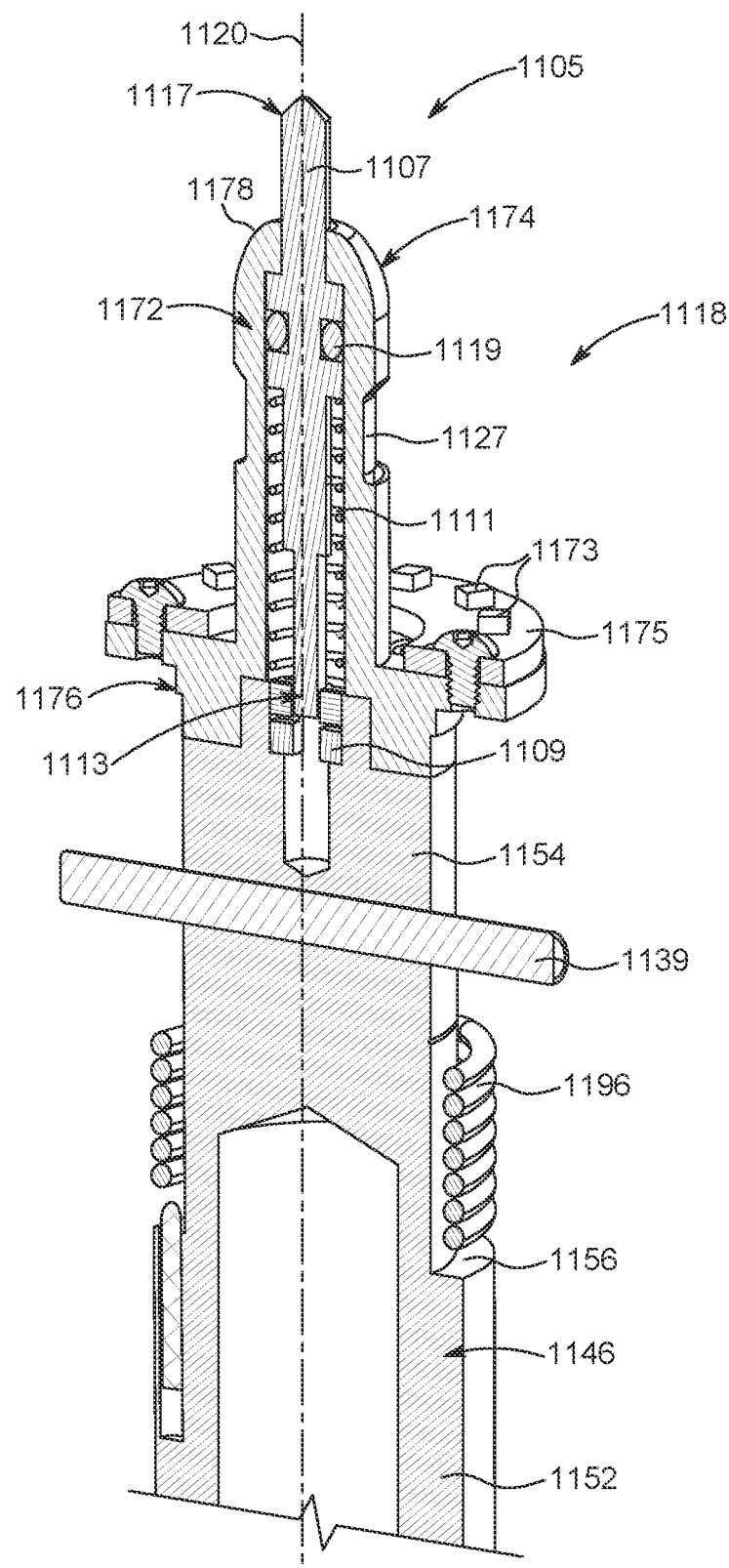
FIG. 29 is a perspective cross-sectional view of a plunger engagement post of the plunger engagement mechanism shown in FIG. 26.

With reference to FIG. 29, the plunger engagement mechanism 1112 further includes a housing 1146 configured for receiving the actuator 1122. The housing 1146 has a proximal portion 1152 connected to a distal portion 1154. In some embodiments, the distal portion 1154 may have a smaller outer diameter than the proximal portion 1152 such that a ledge 1156 is defined at a transition between the proximal portion 1152 and the distal portion 1154. In some embodiments, the ledge 1156 may be configured for supporting a proximal end of a biasing member 1196 configured for releasing the plunger 326 from the piston engagement mechanism 1112 during disengagement of the plunger 326 from the piston 1100. In some embodiments, the biasing member 1196 may be a torsion spring having a first end connected to the housing 1146 and a second end connected to the plunger release sleeve 1158.

With reference to FIG. 26, the plunger engagement sleeve 1114 and the plunger release sleeve 1158 are fixed from rotating relative to each other, but are both rotatable about the longitudinal piston axis 1120 relative to the plunger release post 1118 between a first position and a second position, as described herein with reference to FIGS. 30A-30D. In some embodiments, the plunger engagement sleeve 1114 and the plunger release sleeve 1158 may be rotatable in a clockwise direction and a counterclockwise direction, or one of the clockwise direction and a counterclockwise direction. The plunger engagement sleeve 1114 and the plunger release sleeve 1158 may be rotatable from the first position to the second position due to rotational movement of the plunger 326 around the longitudinal piston axis 1120. For example, the plunger engagement sleeve 1114 and the plunger release sleeve 1158 may be rotatable around the longitudinal axis 1120 due to interaction of the release tabs 380 on the plunger 326 with the toothed portion 1144 on the piston engagement sleeve 1114. The biasing member 1196 may be configured to bias the plunger engagement sleeve 1114 and the plunger release sleeve 1158 to the first position. In this manner, when the plunger engagement sleeve 1114 and the plunger release sleeve 1158 are rotated from the first position toward the second position, the biasing member 1196 builds potential energy therein, which is then used to assist in returning the plunger engagement sleeve 1114 and the plunger release sleeve 1158 toward the first position.

With reference to FIG. 29, the plunger engagement post 1118 is shown separate from the plunger engagement mechanism 1112. The plunger engagement post 1118 has a shaft 1172 having a proximal end 1176 and a distal end 1174. The proximal end 1176 of the shaft 1172 is connected to the housing 1146. The distal end 1174 of the shaft 1172 has a tapered or rounded end surface 1178 configured for contacting the at least one retaining member 368 on the plunger 326 to flexibly deflect the at least one retaining member 368 radially outward as it passes by the end surface 1178. A seal 1180 (FIG. 26) may be provided at the proximal end 1176 for sealing against the inner surface 1128 of the plunger engagement sleeve 1114. The seal 1180 may be an O-ring seal.

Plunger engagement post 1118 further includes the guiding pin 1139 that is configured for guiding the movement of the plunger engagement post 1118 relative to the plunger engagement sleeve 1112 and the plunger release sleeve 1158. In some embodiments, the guiding pin 1139 extends through the housing 1146 and is arranged substantially perpendicular to a longitudinal axis 1120 of the plunger engagement post 1118.

Plunger engagement post 1118 has a locking groove 1127 that is configured to receive the catch 374 of the at least one retaining member 368 of the plunger 326. The end surface 1178 may be shaped to deflect the at least one retaining member 368 in a radially outward direction due to contact of the catch 374 with an outer surface of the end surface 1178. In this manner, distal movement of the piston 1100 relative to the plunger 326 causes the at least one retaining member 368 to be deflected radially outward due to the contact between the catch 374 and the rounded or tapered outer surface of the end surface 1178.

Plunger engagement post 1118 has a sensing member 1105, such as a pin 1107 and a sensor 1109. The pin 1107 has a proximal end 1113 configured for contacting the sensor 1109 when a distal end 1117 of the pin 1107 is urged in a proximal direction, such as due to contact between the plunger 326 and the distal end 1117 of the pin 1107. The pin 1107 may extend along a longitudinal axis 1120 of the piston 1100 and may protrude through at least a portion of the piston head 1106. The pin 1107 may be operative for sensing contact with a surface, such as an inner surface of the plunger 326, and sending one or more signal to controller 200 of the fluid injector to control a movement of the piston 1100 based on the sensed condition. For example, an initial contact between the distal end 1117 of the pin 1107 and the plunger 326 may cause the pin 1107 to be retracted in a proximal direction such that it activates the sensor 1109. The sensor 1109 may be operatively connected to controller 200 which controls the drive mechanism of the piston 1100 such that, upon activation of the sensor 1109 by the pin 1107, the sensor 1109 controls the movement of the drive mechanism. For example, the drive mechanism may be stopped or slowed from a first rate to a second, slower rate. The pin 1107 may be biased to its distal position by a spring 1111. A seal 1119 may be provided between the pin 1107 and the plunger engagement post 1118 to prevent fluid ingress.

With continued reference to FIG. 29, one or more lights 1173 may be provided on a printed circuit board 1175 on the base of the plunger engagement post 1118. The one or more lights 1173 may be configured for illuminating at least a portion of the plunger 326 and the plunger engagement sleeve 1114, as described herein.

Having described the structure of the plunger 326 and the piston 1100 in accordance with one non-limiting embodiment of the present disclosure, a method of engagement of the plunger 326 with and from the piston 1100 will now be described with reference to FIGS. 30A-30D. FIGS. 31A-31D show the plunger engagement mechanism 1112 during various stages of disengagement of the plunger 326 from the piston 1100.

Figure 30A:
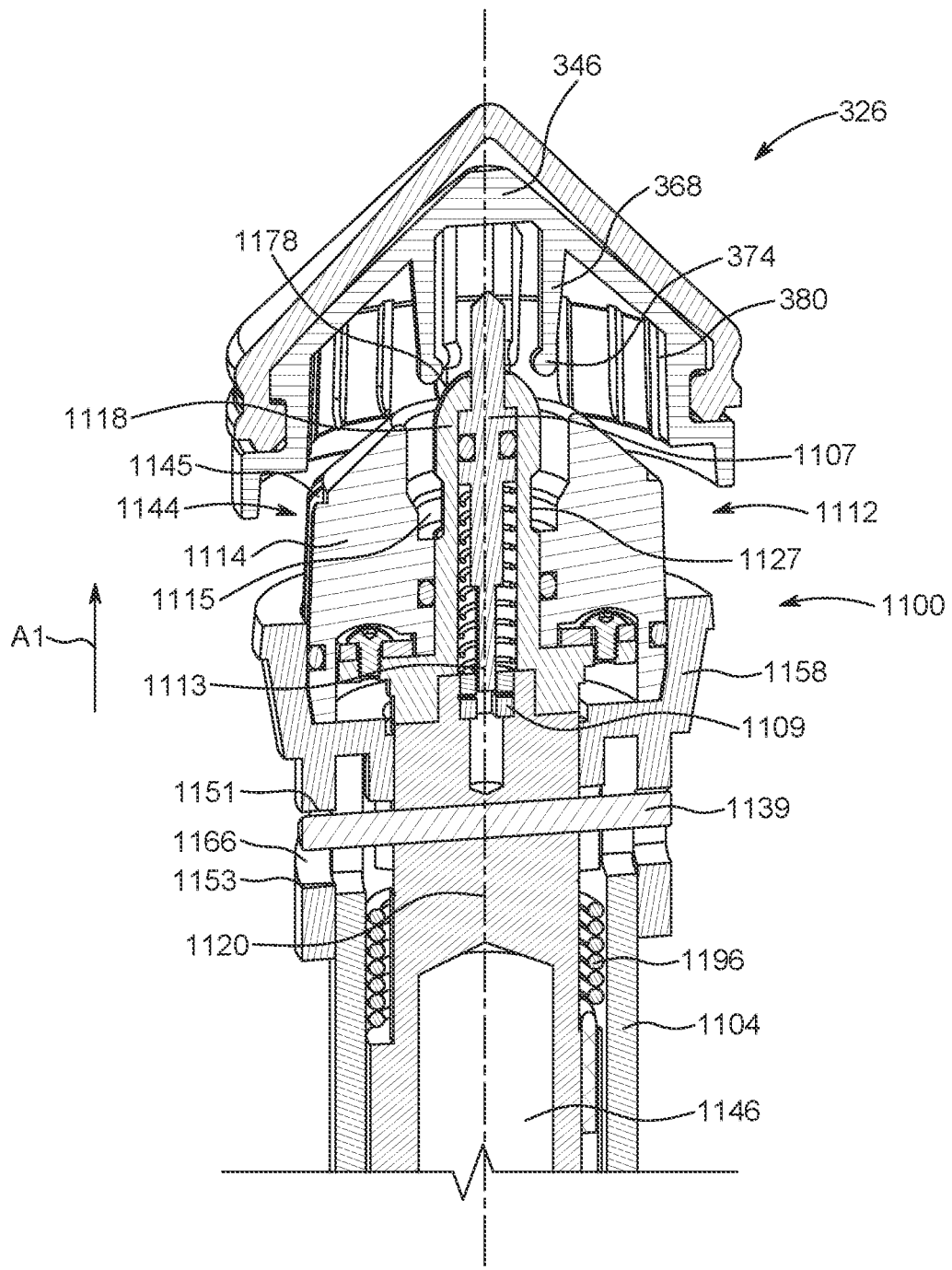
FIGS. 30A-30D are perspective cross-sectional views of the engagement operation of the piston and the plunger engagement mechanism of FIG. 26, with the plunger engagement mechanism shown in various stages during engagement of the plunger.

FIG. 30A shows the piston 1100 with its plunger engagement mechanism 1112 in a disengaged position or state and prior to connection with the plunger 326. In some embodiments, the default state of the plunger engagement mechanism 1112 may be the engaged position or state. In other embodiments, the default state of the plunger engagement mechanism 1112 may be the disengaged position or state. To connect the plunger 326 to the piston 1100, the syringe 300 is first connected to the injector. During connection of the syringe 300 to the injector, the piston 1100 is withdrawn in the housing of the injector. After connecting the syringe 300 to the injector, the piston 1100 can be advanced in a distal direction toward the plunger 326 within the bore of the syringe 300.

With reference to FIG. 30A, the actuator 1122 (shown in FIG. 26) is operated to its disengaged position or state, wherein the plunger engagement post 1118 is positioned at its distal position. Movement of the plunger engagement post 1118 in the distal direction opens the receiving space 1115 between the plunger engagement sleeve 1114 and the plunger engagement post 1118 to permit insertion of the one or more retaining members 368 of the plunger 326 into the receiving space 1115. The pin 1107 is in its distal position, while the guiding pin 1139 is at a distal end 1151 of the longitudinal surface 1163 of the opening 1162 (FIG. 28) on the plunger release sleeve 1158.

Figure 30B:
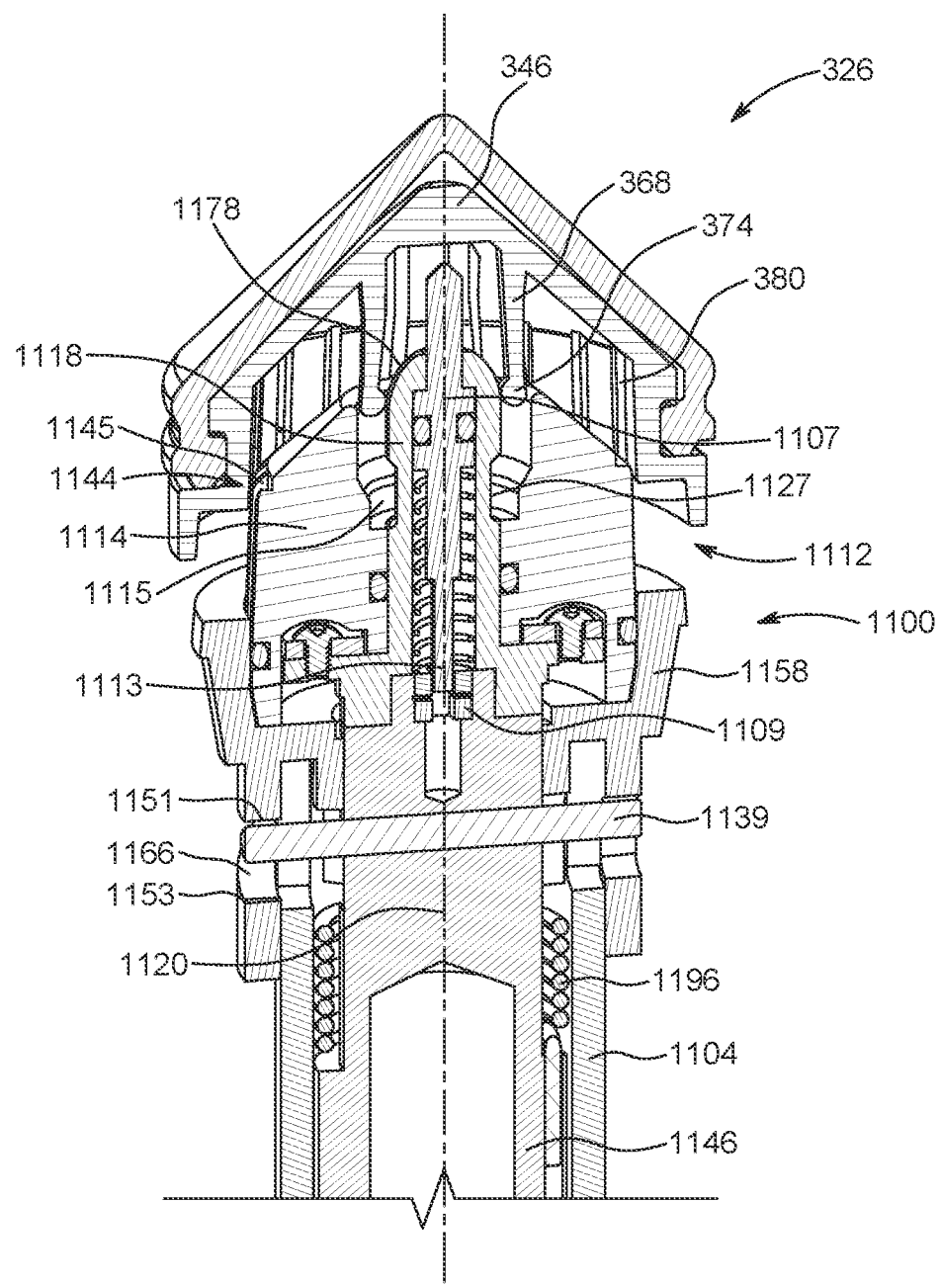

With reference to FIG. 30B, the piston 1100 is moved axially in a distal direction toward the plunger 326 (indicated by arrow A1). In some embodiments, the piston 1100 may be advanced distally using the drive mechanism 402 operated by the controller 200 (FIG. 2) of the injector. In other embodiments, the piston can be manually moved in the distal direction. The piston 1100 is advanced axially in a distal direction such that the at least one retaining member 368 of the plunger 326 is received within the central opening 1116 of the plunger engagement sleeve 1114. As the piston 1100 is advanced in the distal direction toward the plunger 326, at least a portion of the one or more retaining members 368 on the plunger 326 contacts the tapered end surface 1178 of the plunger engagement post 1118, which flexibly deflects the retaining members 368 in a radially outward direction. For example, because the catch 374 protrudes radially inward relative to the second end of each retaining member 368, the catch 374 contacts the tapered surface 1178 of the plunger engagement post 1118, which deflects the retaining members 368 in a radially outward direction. In embodiments having a plurality of retaining members 368, each of the retaining members 368 is deflected in the radially outward direction.

Figure 30C:
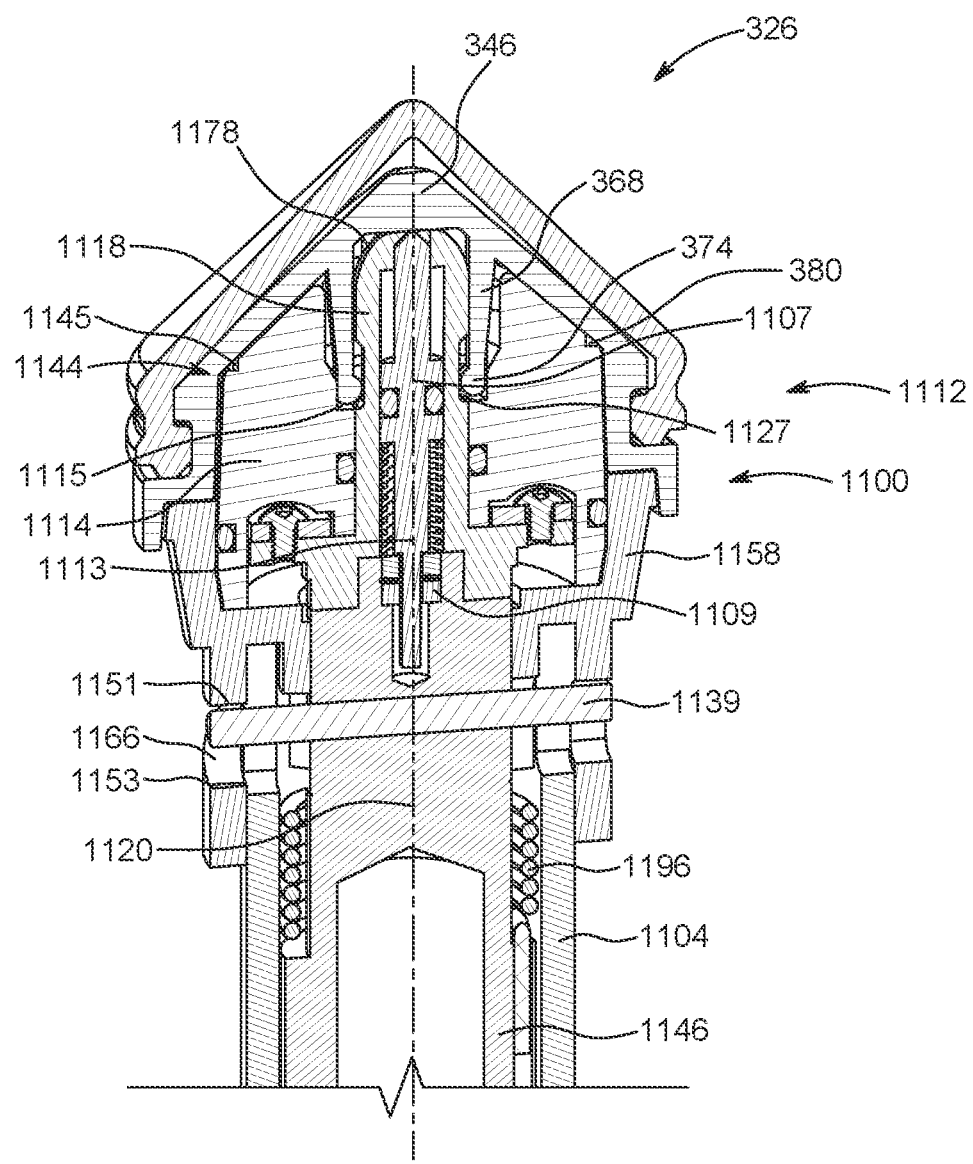

With reference to FIG. 30C, during continued axial movement of the piston 1100 in the distal direction, the retaining member 328 is positioned such that the catch 374 can deflect into the locking groove 1127 of the piston engagement post 1118. After the catch 374 is positioned in the locking groove 1127, e at least one retaining member 368 can elastically deflect in a radially inward direction and the retaining member 328 may ride up ramp 1130 on the inner surface 1128 of the central opening 1116 and into the second diameter of inner surface 1128. While the at least one retaining member 368 is in the position shown in FIG. 30C, the plunger 326 is not in a locked engagement with the piston 1100 because the at least one retaining member 368 can be deflected in a radially outward direction with proximal movement of the piston 1100 or distal movement of the plunger 326 (such as due to removal of the syringe from the injector), and catch 374 may move out of the locking groove 1127. With the plunger 326 connected to the piston 1100, the one or more release tabs 380 on the plunger 326 are aligned with the toothed portion 1144 on the outer surface 1142 of the plunger engagement sleeve 1114 (FIG. 30A). The pin 1107 of the sensing member 1105 is moved axially in a proximal direction due to contact with the plunger 326 such that the proximal end 1113 of the pin 1107 can be detected by the sensor 1109, signaling controller 200 to stop further distal movement of the piston 1100.

Figure 30D:
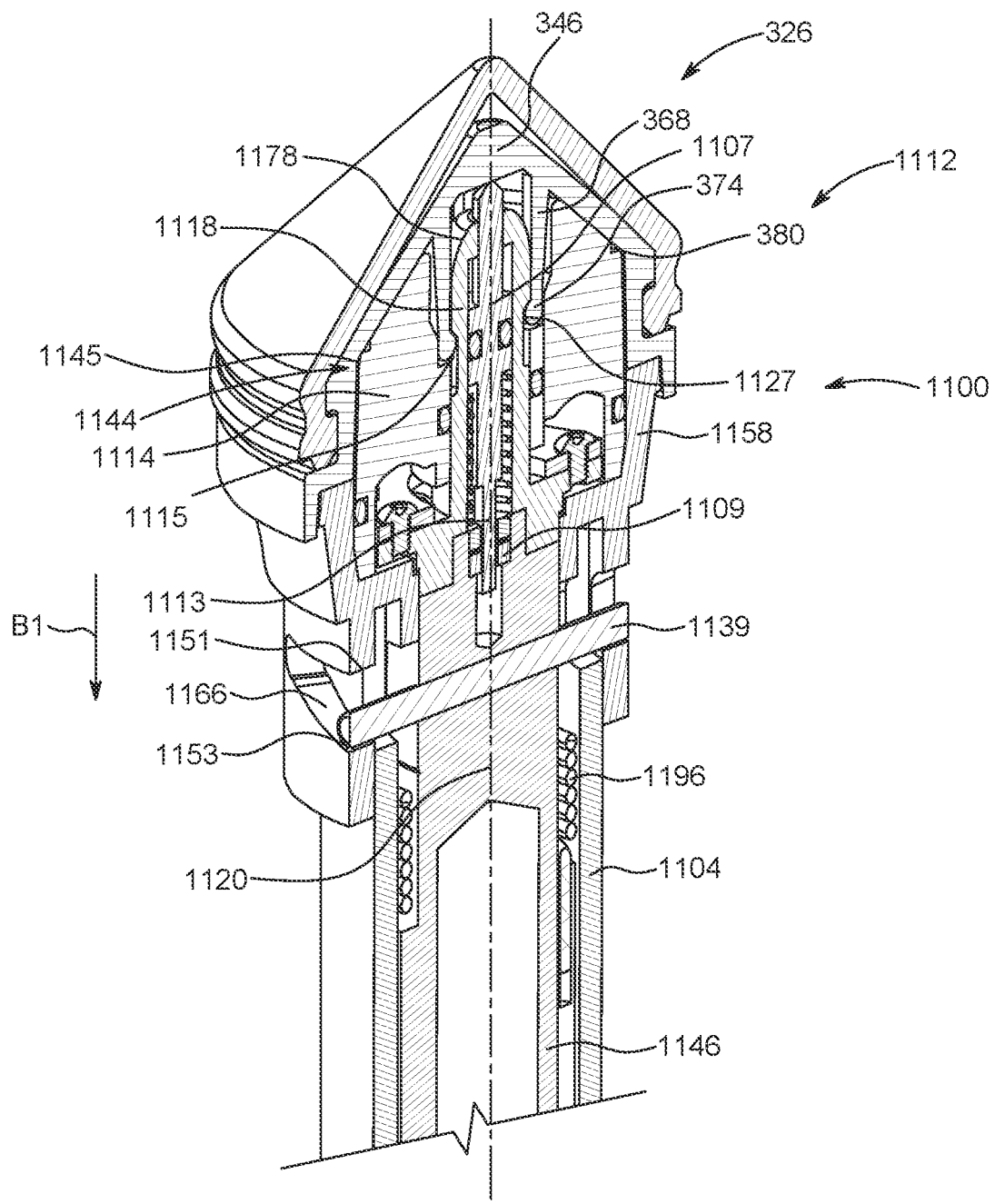

With reference to FIG. 30D, the actuator 1122 (FIG. 26) is operated to move the plunger engagement post 1118 in a proximal direction indicated by arrow B1 from a disengaged position or state to an engaged position or state. Movement of the plunger engagement post 1118 in the distal direction closes the receiving space 1115 between the plunger engagement sleeve 1114 and the plunger engagement post 1118 locking the catch 374 within locking groove 1127 to prevent removal of the one or more retaining members 368 of the plunger 326 from disengaging and moving out of the receiving space 1115. Once the plunger engagement post 1118 is moved to the engaged position or state, the at least one retaining member 368, including the catch 374, of the plunger 326 is captured between the plunger engagement sleeve 1114 and the plunger engagement post 1118 such that axial movement of the piston 1100 results in a corresponding axial movement of the plunger 326 within the syringe barrel. As the plunger engagement post 1118 is moved in the proximal direction, the guiding pin 1139 moves axially in the proximal direction from a distal end 1151 of the longitudinal surface 1163 of the opening 1162 (FIG. 28) on the plunger release sleeve 1158 to a proximal end 1153.

The piston 1100 and the connected plunger 326 may then be moved reciprocally within the barrel 318 of the syringe 300. In some embodiments, the piston 1100 may be advanced distally to deliver the fluid from the syringe 300 or proximally to fill the syringe 300 with fluid using the drive mechanism 402 operated by the controller 200 (FIG. 2).

With reference to FIGS. 31A-31D, to unlock the syringe 300 from the syringe port of the injector and disengage the plunger 326 from the piston 1100, the syringe 300 may be rotated clockwise or counter-clockwise about the syringe longitudinal axis 315 (FIG. 5B), relative to the syringe port. Because the plunger 326 is substantially free from rotation within the syringe barrel 318 due to frictional contact therebetween, rotation of the syringe 300 also causes the plunger 326 to rotate relative to the piston 1100 about the longitudinal piston axis 1120. Due to alignment of the one or more release tabs 380 on the plunger 326 with the plunger release teeth 1145 on the toothed portion 1144 of the plunger engagement sleeve 1114, rotation of the plunger 326 also rotates the plunger engagement sleeve 1114 and the plunger release sleeve 1158 relative to the plunger engagement post 1118 from the first position to the second position. Because the guiding pin 1139 on the plunger engagement post 1118 is received within the opening 1162 on the plunger release sleeve 1158, and because the plunger engagement post 1118 is free from rotation about the longitudinal piston axis 1120, rotation of the plunger engagement sleeve 1114 causes the guiding pin 439 to be guided along the ramped surface 1166 of the plunger release sleeve 1158 (see, also, FIG. 28) from a first position shown in FIG. 30D to a second position shown in FIG. 31A (e.g., from a proximal end of the ramped surface 1166 toward a distal end of the ramped surface 1166). In addition, rotation of plunger engagement sleeve 1114 about longitudinal piston axis 1120 builds potential energy in the biasing member 1196.

Figure 31A:
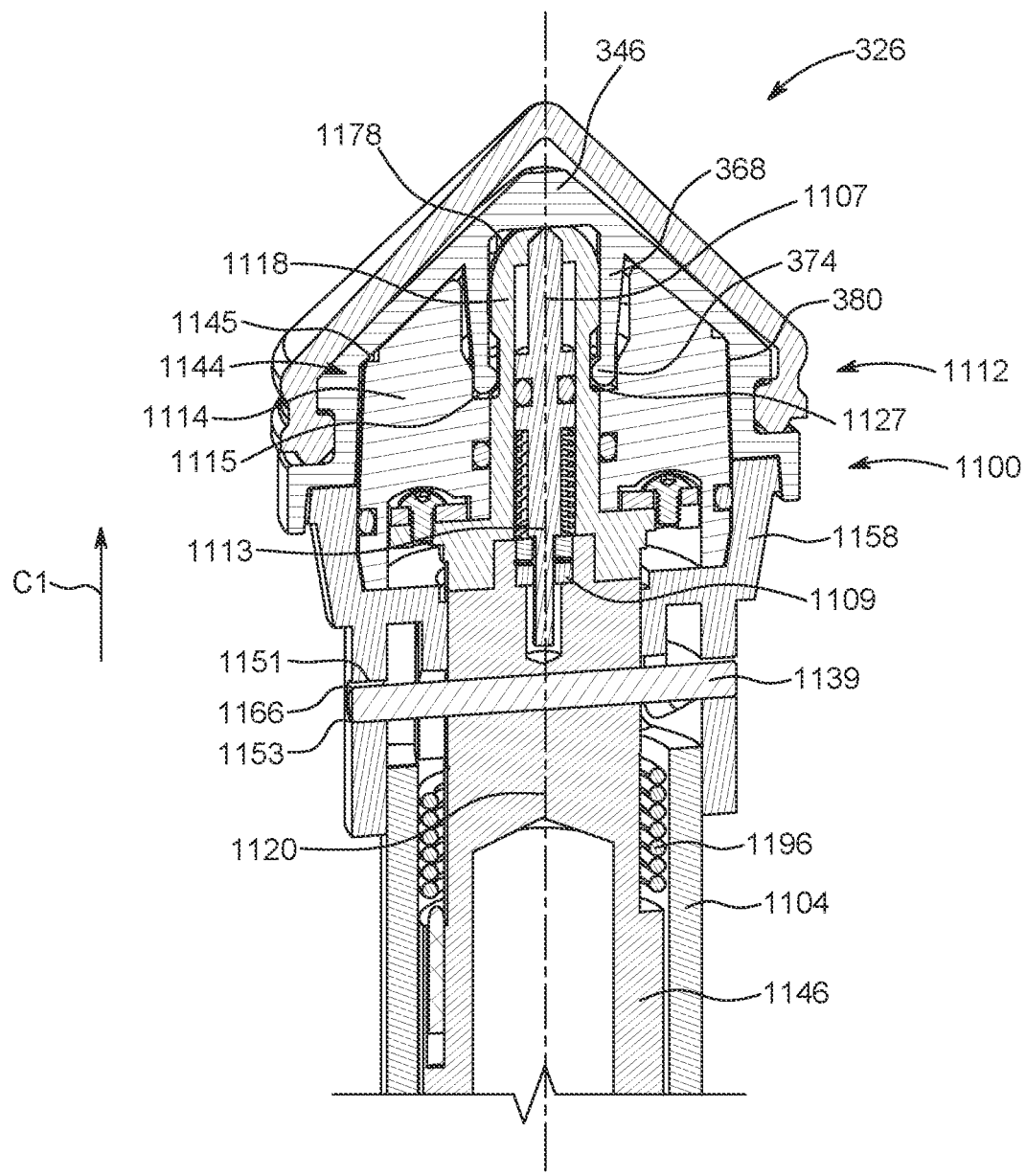
FIGS. 31A-31D are perspective cross-sectional views of the disengagement operation of the piston and the plunger engagement mechanism of FIG. 26, with the plunger engagement mechanism shown in various stages during disengagement of the plunger.
Figure 31B:
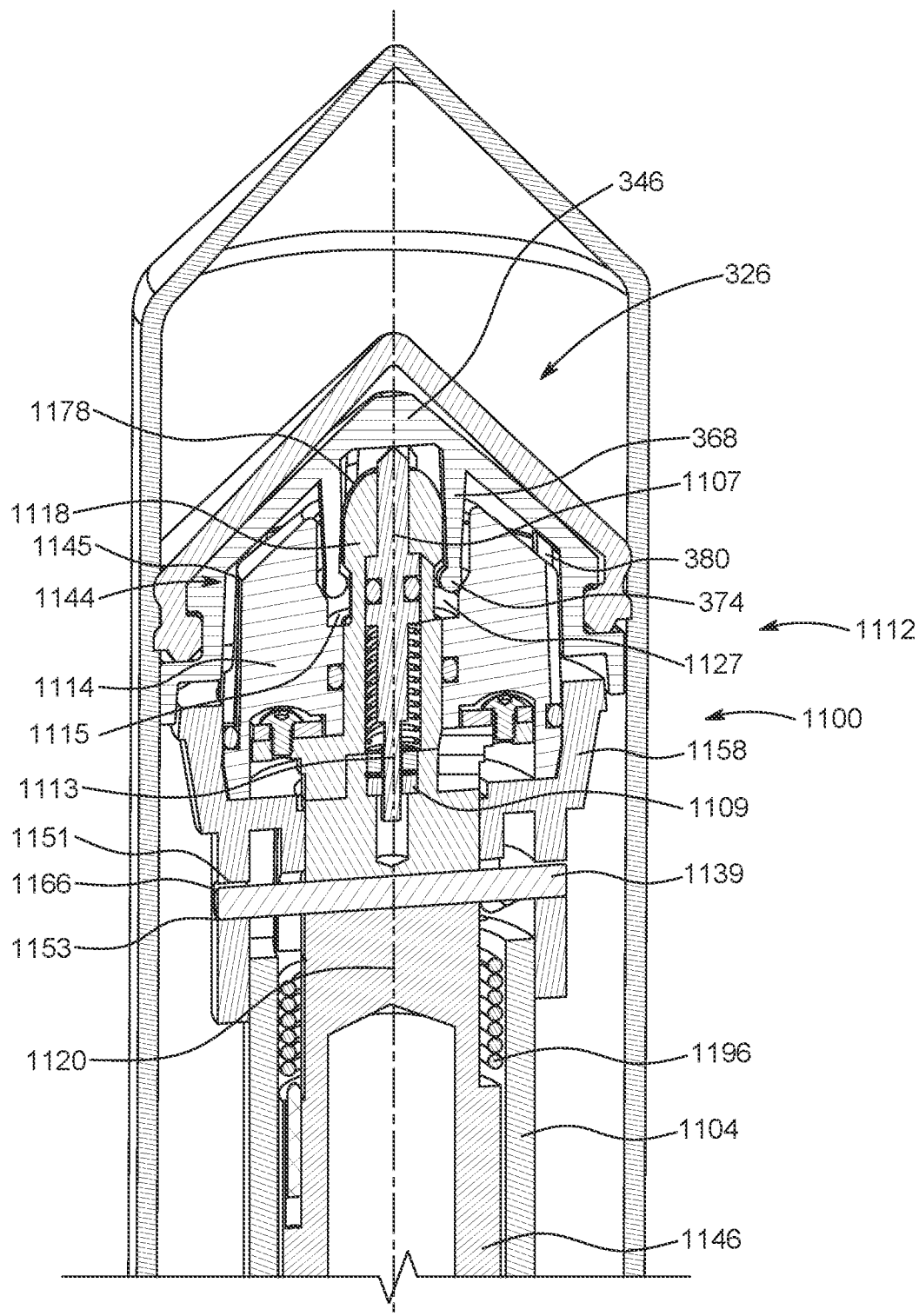

With continued reference to FIG. 31A, movement of the guiding pin 1139 along the ramped surface 1166 of the plunger release sleeve 1158 causes the plunger engagement post 1118 to be moved axially from the engaged position or state to the disengaged position or state in a distal direction of arrow C1. Movement of the plunger engagement post 1118 in the distal direction opens the receiving space 1115 between the plunger engagement sleeve 1114 and the plunger engagement post 1118 to permit distal movement of the one or more retaining members 368 of the plunger 326 from the receiving space 1115 (see FIG. 31B).

Figure 31C:
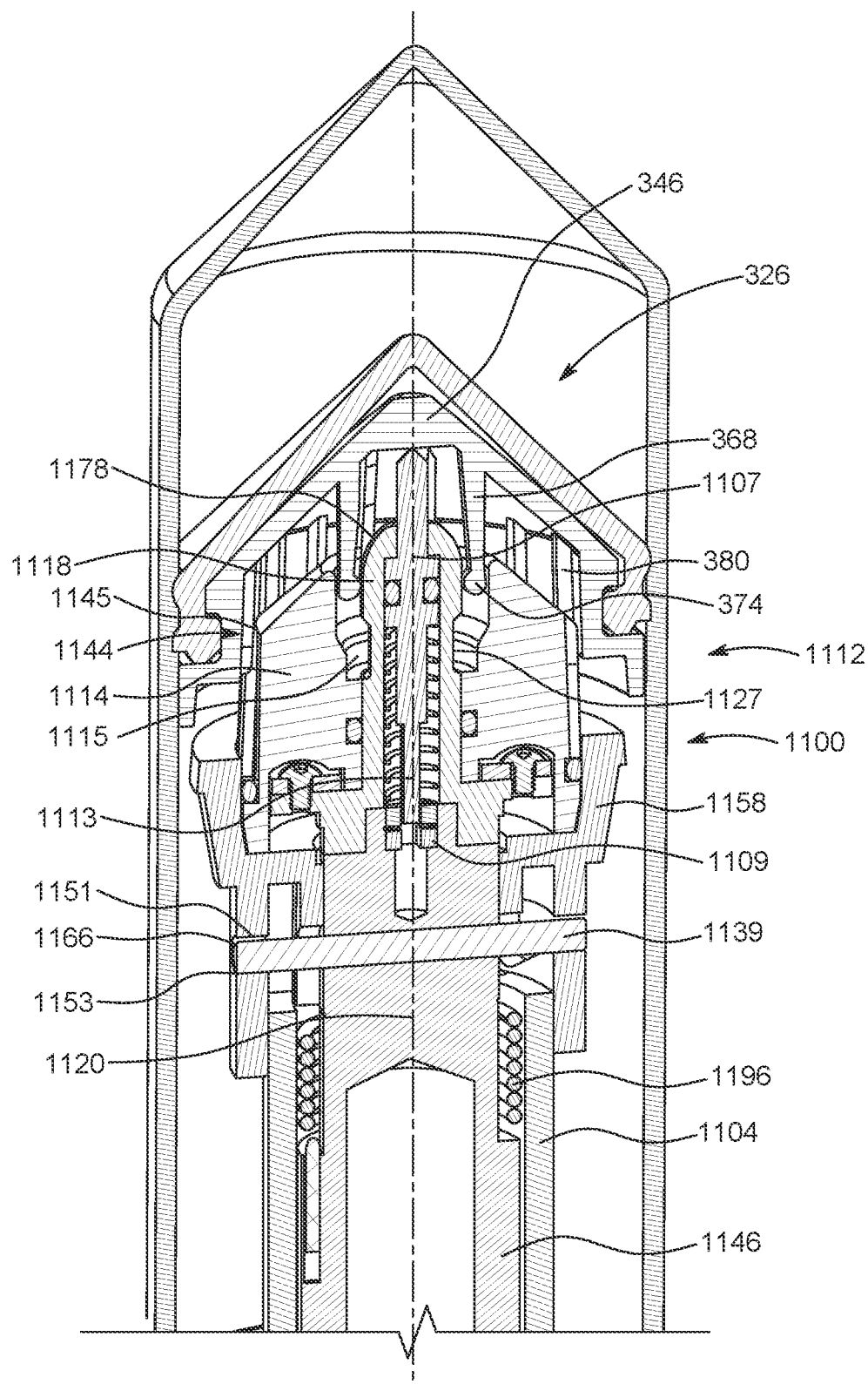

With the plunger engagement mechanism 1112 in the disengaged position or state, the syringe 300 can be pulled in the distal direction or the piston 1100 can be retracted in the proximal direction to remove the plunger 326 from the piston 1100. During such relative movement of the piston 326 to the plunger 1100 in a direction away from each other, the catch 374 of each of the at least one retaining members 368 engages the plunger engagement post 1118 distally of the locking groove 1127 such that each retaining member 368 is flexibly deflected in a radially outward direction (FIG. 31C). Continued movement of the piston 1000 relative to the plunger 326 allows the plunger 326 to be freely pulled away from the piston 1100, such as shown in FIG. 31D, allowing removal of the syringe 300 from the injector port.

Figure 31D:
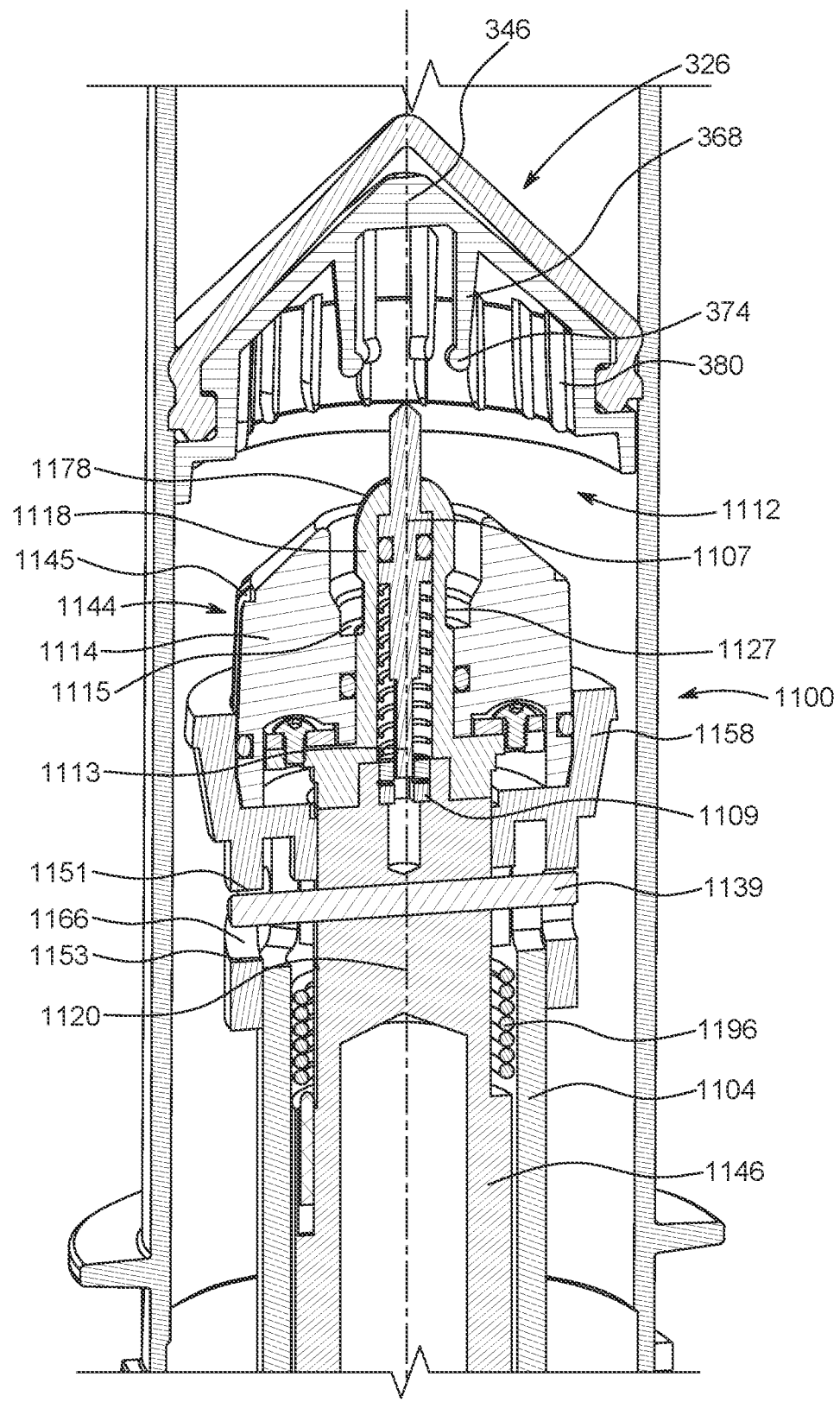

With reference to FIG. 31D, after the plunger 326 is removed from the piston 1100, the plunger engagement sleeve 1114 and the plunger engagement post 1118 are automatically rotated about the longitudinal axis 1120 from the second position to the first position due to the restoring force provided by the biasing member 1196. With movement of the plunger engagement sleeve 1114 and the plunger engagement post 1118 to the first position, the guiding pin 1129 is guided along a top surface 1179 within the opening 1162 of the plunger release sleeve 1158 due to the restoring force provided by the biasing member 1196.

Next, referring to FIGS. 32-35B, an injector assembly 2000 in accordance with another aspect of the present disclosure is shown. Injector assembly 2000 comprises a housing 2002, which houses an automated or powered fluid injector. The fluid injector is adapted to interface with and actuate one or more syringes, wherein each syringe may be independently filled with a medical fluid such as contrast media, saline solution, or any desired medical fluid, as is similarly described above with respect to FIG. 1 or FIG. 3. For example, injector housing 2002 is configured to hold syringes 2006a, 2006b, each containing a medical fluid therein.

As is known in the art, syringes 2006a, 2006b are often made of polypropylene or a similar material having a certain minimum wall thickness. During certain procedures, such as angiography imaging procedures, syringes 2006a, 2006b may be subject to pressures of up to 1200 psi when used to inject fluid into a patient, and thus wall thickness and resilience of the syringe are important in ensuring that the syringe does not radially expand, burst, disengage from the injector, or leak. To further combat possible radial expansion of syringes 2006a, 2006b when subject to high pressure injection, respective pressure jackets 2004a, 2004b may be utilized to enclose and retain syringes 2006a, 2006b. Pressure jackets 2004a, 2004b act to limit radial expansion of the syringe barrels. That is, during an injection procedure, exterior walls of syringes 2006a, 2006b expand against an interior wall of respective pressure jackets 2004a, 2004b, thereby limiting the radial expansion of the exterior walls of syringes that could otherwise lead to bursting or leakage.

Pressure jackets 2004a, 2004b may be separate elements or may be formed in a one-piece, monolithic design. Pressure jackets 2004a, 2004b are retained on an injector head of housing 2002 via respective attachment interfaces 2010a, 2010b. Suitable nonlimiting examples of pressure jackets including syringe retention features for use in a CV injection procedure are described in International PCT Application PCT/US2020/049885, incorporated herein by reference.

In addition to radial forces acting on syringes 2006a, 2006b and pressure jackets 2004a, 2004b, significant axial movement during high pressure injection is also possible due to the elastic nature of the structural components restraining syringes 2006a, 2006b. For example, a single 150 ml syringe having a cross-sectional area of 1.6 in$^2$ at 1200 psi may require a force of 2400 psi to restrain forward motion of the syringe. To restrict this axial motion of syringes 2006a, 2006b, respective caps 2008a, 2008b may be used to partially encapsulate the distal end of syringes 2006a, 2006b and retain syringes 2006a, 2006b within the injector and within pressure jackets 2004a, 2004b during high-pressure injection. Caps 2008a, 2008b may have an opening formed on a distal end thereof to allow at least a portion of a neck 2009a, 2009b of syringes 2006a, 2006b to protrude therethrough, thereby allowing syringes 2006a, 2006b to be connected to fluid lines leading to the patient.

Due to the axial forces imparted on syringes 2006a, 2006b, it is desirable for the attachment interfaces between the pressure jackets 2004a, 2004b and the housing 2002 and/or between the caps 2008a, 2008b and the pressure jackets 2004a, 2004b to be of sufficient strength to resist undo axial movement or inadvertent detachment. However, while strength is key, it is also important for an operator to be able to easily remove the caps 2008a, 2008b and/or pressure jackets 2004a, 2004b, as it is necessary to remove or insert syringes 2006a, 2006b. Accordingly, it is desirable for the connection interface between pressure jackets 2004a, 2004b and housing 2002 to be sufficiently secure, yet allow for easy attachment and removal. Similarly, it is desirable for the connection interface between caps 2008a, 2008b and pressure jackets 2004a, 2004b to also be secure, yet allow for easy attachment and removal.

Figure 32:
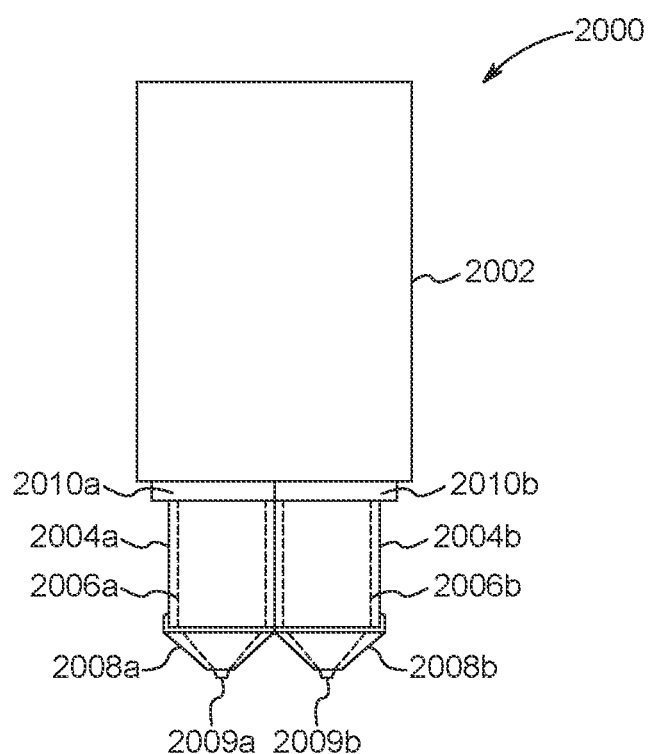
FIG. 32 is a top view of a system including a fluid injector and pressure jackets according to another embodiment of the present disclosure.

In order to achieve these desired attributes, attachment interfaces 2010a, 2010b of pressure jackets 2004a, 2004b may have connector features similar to those of the plunger 326 shown and described with respect to FIGS. 6-8C, while attachment interfaces 2020a, 2020b of housing 2002, shown in FIG. 32, may have connector features similar to those of various embodiments of the plunger engagement mechanisms shown and described with reference to FIGS. 9-31D. That is, attachment interfaces 2010a, 2010b may comprise one or more resiliently flexible retaining members having a catch, similar to the resiliently flexible retaining members 368 and the catch 374 shown and described with reference to FIGS. 6-8C, that are positioned circumferentially about an opening on the proximal end of pressure jackets 2004a, 2004b. Similarly, attachment interfaces 2020a, 2020b of housing 2002 may comprise one or more features, similar to the plunger engagement sleeve and plunger engagement post shown and described with respect to FIGS. 9-31D.

In operation, attachment interfaces 2010a, 2010b, and 2020a, 2020b are configured to interact in manner substantially similar to the interaction between the plunger 326 and the plunger engagement mechanism, as shown and described in detail with respect to FIGS. 9-31D. That is, as attachment interfaces 2010a, 2010b are axially directed toward respective attachment interfaces 2020a, 2020b such that respective attachment interfaces 2010a, 2010b and attachment interfaces 2020a, 2020b interact to enable the pressure jackets 2004a, 2004b to be secured to housing 2002. One or more retaining members within attachment interfaces 2020a, 2020b, which in certain embodiments may protrude inwardly from a distal end of attachment interfaces 2020a, 2020b, are then configured to engage a lip of an engagement ring within each of attachment interfaces 2010a, 2010b to securely attach the pressure jackets 2004a, 2004b to housing 2002.

To detach pressure jackets 2004a, 2004b from housing 2002, pressure jackets 2004a, 2004b can be rotated (together or separately) relative to housing 2002. Rotation of pressure jackets 2004a, 2004b allows the attachment interfaces 2010a, 2010b to interact with attachment interfaces 2020a, 2020b, similar to that which is described above with respect to FIGS. 9-31D. This interaction of acts to push the at least one retaining member radially outward or inward such that the at least one retaining member no longer engages the corresponding structure on the attachment interfaces 2010a, 2010b, at which point the pressure jackets 2004a, 2004b can be axially detached from housing 2002.

Alternatively, upon insertion, the proximal end of the body of syringes 2006a, 2006b in pressure jackets 2004a, 2004b may act analogously to the plunger engagement post, locking the catches of the corresponding flexible retaining members of the pressure jackets in corresponding locking grooves or lips in the pressure jacket ports on the injector. Removal of syringes 2006a, 2006b from pressure jackets 2004a, 2004b, for example after completion of an injection protocol, may disengage the flexible retaining members of the pressure jackets from corresponding locking grooves or lips in the pressure jacket ports, allowing removal of the pressure jackets from the ports.

In accordance with an alternative aspect of the disclosure, the structural details of attachment interfaces 2010a, 2010b and 2020a, 2020b described above could be reversed. That is, attachment interfaces 2010a, 2010b of pressure jackets 2004a, 2004b could comprise, for example, the at least one retaining member and corresponding features, while the attachment interfaces 2020a, 2020b could comprise the features of the plunger engagement mechanism described herein with reference to FIGS. 9-31D.

Figure 33:
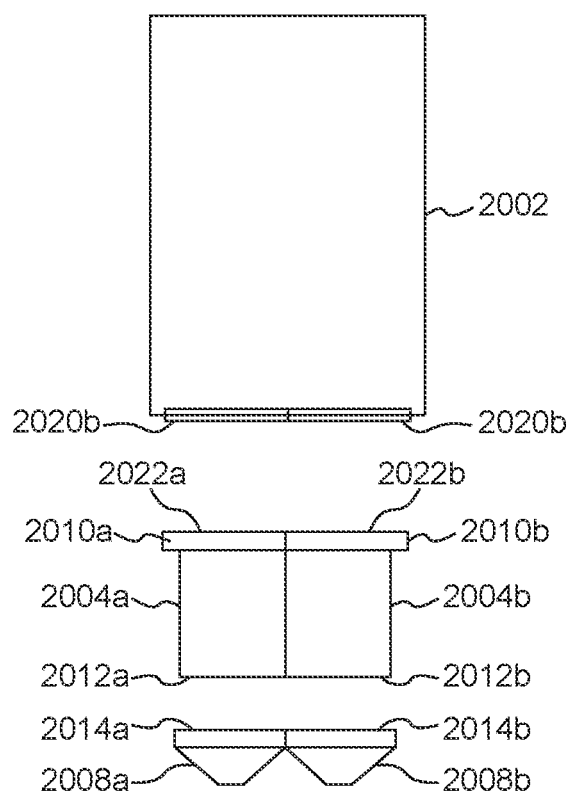
FIG. 33 is an exploded top view of the system of FIG. 32.
Figure 34:
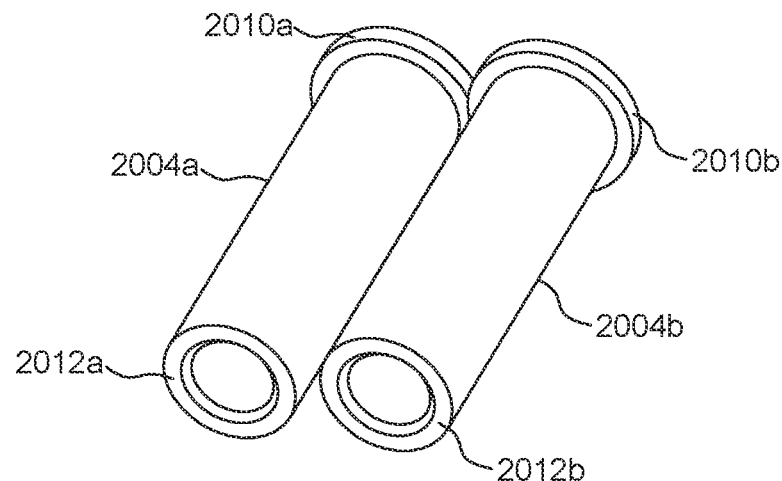
FIG. 34 is a perspective view of a pair of pressure jackets according to another embodiment of the present disclosure.
Figure 35A:
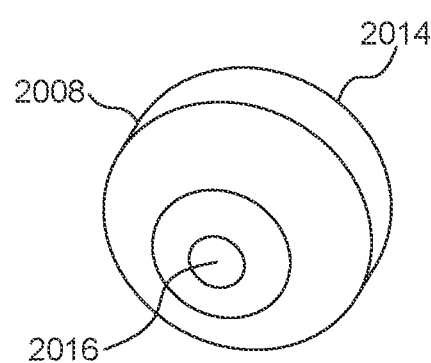
FIG. 35A is a perspective view of a syringe cap according to another embodiment of the present disclosure.
Figure 35B:
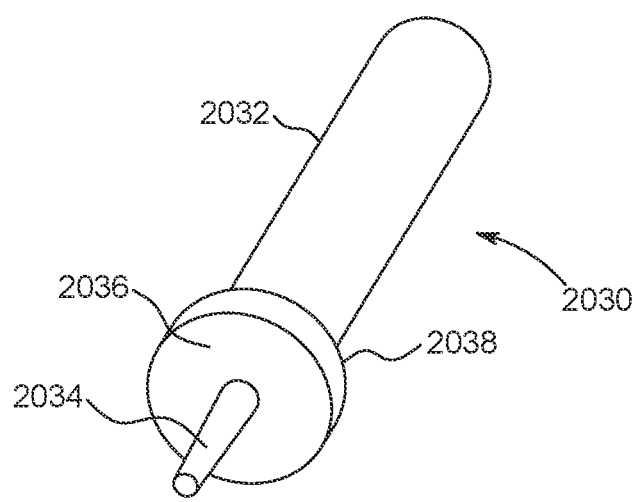
FIG. 35B is a perspective view of a syringe assembly according to another embodiment of the present disclosure.

Next, referring to FIG. 34, FIG. 35A, and FIG. 35B, an alternative aspect of the disclosure is shown. As discussed above with respect to FIGS. 32-33, caps 2008a, 2008b may generally be disposed about a distal end of respective pressure jackets 2004a, 2004b so as to axially retain the respective syringes therein. As shown in FIG. 35A, a cap 2008 may have an attachment interface 2014 for attachment to a pressure jacket, as well as an opening 2016 formed therein to allow a portion of the distal end of the syringe to extend therethrough.

To obtain a secure connection between pressure jackets 2004a, 2004b and caps 2008a, 2008b, it would be advantageous to configure the respective interfaces between pressure jackets 2004a, 2004b and caps 2008a, 2008b such that they interact in manner substantially similar to the interaction between various embodiments of the plunger 326 and various embodiments of the plunger engagement mechanisms shown and described in detail with respect to FIGS. 9-31D. As shown in FIG. 33, pressure jackets 2004a, 2004b may have respective attachment interfaces 2012a, 2012b at distal ends thereof for engagement with respective caps 2008a, 2008b. Attachment interfaces 2012a, 2012b may include one or more plunger engagement mechanisms as shown and described with respect to FIGS. 9-31D. Similarly, attachment interface 2014 of cap 2008 shown in FIG. 35A may include one or more resiliently deflectable retaining members 368 along with a corresponding catch 374, as shown and described with reference to FIGS. 6-8C. The engagement between attachment interfaces 2012a, 2012b of the pressure jackets 2004a, 2004b and the attachment interface 2014 of respective caps 2008 may be identical or substantially similar to the engagement between the plunger 326 and the plunger engagement mechanisms described above with respect to FIGS. 9-31D. In this way, caps 2008a, 2008b may be securely engageable with, and readily detachable from, the distal end of pressure jackets 2004a, 2004b.

As an alternative to a cap 2008 separate from and surrounding a portion of a syringe, FIG. 35B shows a syringe assembly 2030 having a syringe body 2032 with a cap 2036 integrated therewith. That is, cap 2036 may be molded or formed directly with syringe body 2032. A neck portion 2034 extends from a distal surface of cap 2036 to provide a connection point for fluid lines leading to the patient. An attachment interface 2038, similar to attachment interface 2014 shown and described with respect to FIG. 35A, is formed in cap 2038. As similarly described above with respect to FIGS. 32 and 35A, attachment interface 2038 may include features which interact with one of corresponding attachment interface 2012a, 2012a of pressure jackets 2004a, 2004b. Again, the engagement between attachment interfaces 2012a, 2012b of the pressure jackets 2004a, 2004b and the attachment interface 2038 of respective syringe assemblies 2030 may be identical or substantially similar to that described above with respect to FIGS. 9-31D.

In accordance with an alternative aspect of the disclosure, the structural details of attachment interfaces 2012a, 2012b, and 2014 described above could be reversed. That is, attachment interfaces 2012a, 2012b of pressure jackets 2004a, 2004b could comprise, for example, the at least one retaining member and corresponding features, while the attachment interface 2014 of each cap 2008 could comprise the corresponding features associated with the plunger engagement mechanism described herein with reference to FIGS. 9-31D. Likewise, structural details of attachment interfaces 2012a, 2012b, and 2038 described above could be reversed.

While shown and described as being integrated with pressure jackets 2004a, 2004b, one or both of attachment interfaces 2010a, 2010b and 2012a, 2012b of pressure jackets 2004a, 2004b may alternatively be formed of a separate component attachable to the proximal or distal end of pressure jackets 2004a, 2004b. In this way, a conventional pressure jacket could be adapted with one or more separate attachment interfaces to enable the pressure jacket to securely interface with an appropriately-equipped housing, a cap similar to cap 2008, and/or a syringe assembly having an integrated cap, similar to syringe assembly 2030 discussed above.

Although the disclosure has been described in detail for the purpose of illustration based on what are currently considered to be the most practical and preferred embodiments, it is to be understood that such detail is solely for that purpose and that the disclosure is not limited to the disclosed embodiments, but, on the contrary, is intended to cover modifications and equivalent arrangements. For example, it is to be understood that the present disclosure contemplates that, to the extent possible, one or more features of any embodiment can be combined with one or more features of any other embodiment.

What is claimed is:

1. A plunger for use with a syringe, the plunger comprising:
a plunger body defining a central longitudinal axis and having a proximal end, a distal end, and a circumferential sidewall connecting the proximal end and the distal end; and
at least one retaining member associated with and extending proximally from the plunger body, the at least one retaining member comprising:
a first end connected to the plunger body;
a second end proximal to the first end and radially and resiliently deflectable relative to the first end; and
at least one catch on the second end,
wherein the at least one retaining member has an outer surface configured to engage a plunger engagement sleeve of a plunger engagement mechanism on a piston of a fluid injector system when the plunger is in a locked state with the piston,
wherein the at least one retaining member has an inner surface configured to engage a plunger engagement post of the plunger engagement mechanism when the plunger is in the locked state with the piston,
wherein the at least one catch is configured to fixedly engage a locking feature on one of the plunger engagement sleeve and the plunger engagement post when the plunger is in the locked state with the piston to prevent axial movement of the plunger relative to the piston,
wherein the at least one catch has a first rounded or angled proximal surface at a proximal end of the at least one catch for flexibly engaging a distal end of the locking feature on one of the plunger engagement sleeve and the plunger engagement post during engagement of the plunger to the piston, and a second rounded or angled distal surface at a distal end of the at least one catch for flexibly engaging a proximal end of the locking feature on one of the plunger engagement sleeve and the plunger engagement post during disengagement of the plunger from the piston; and
wherein in an unlocked state of the plunger engagement mechanism the first rounded proximal surface and the second rounded distal surface of the at least one catch are configured to radially deflect the second end of the at least one retaining member upon axial movement of the piston relative to the plunger due to a flexing interaction of the at least one catch with the locking feature on one of the plunger engagement sleeve and the plunger engagement post.

2. The plunger according to claim 1, wherein the at least one retaining member comprises a plurality of retaining members spaced apart around the central longitudinal axis.

3. The plunger according to claim 1, wherein the at least one retaining member extends proximally in a direction parallel with the central longitudinal axis.

4. The plunger according to claim 1, wherein the plunger is configured to engage the plunger engagement mechanism regardless of angular orientation of the plunger relative to the piston of the fluid injector system.

5. The plunger according to claim 1, wherein the at least one catch protrudes radially inward from the inner surface of the at least one retaining member in a direction toward the central longitudinal axis.

6. The plunger according to claim 1, wherein the at least one catch protrudes radially outward from the outer surface of the at least one retaining member in a direction away from the central longitudinal axis.

7. The plunger according to claim 1, wherein the at least one catch defines a locking recess for receiving at least a portion of the plunger engagement mechanism when the plunger is connected to the piston.

8. The plunger according to claim 1, wherein the at least one catch protrudes radially inward from the inner surface of the at least one retaining member in a direction toward the central longitudinal axis, and wherein the at least one catch is configured to be received within the locking feature that is shaped as a locking groove protruding radially inward from an outer surface of the plunger engagement post when the plunger is in the locked state with the piston.

9. The plunger according to claim 1, wherein the plunger body has conical-shaped portion at the distal end and a cylindrical-shaped portion at the proximal end.

10. The plunger according to claim 9, wherein the at least one retaining member protrudes proximally from an inner surface of the conical-shaped portion.

11. The plunger according to claim 10, further comprising a plurality of release tabs protruding radially inward from an inner surface of the cylindrical-shaped portion or proximally from the inner surface of the cylindrical-shaped portion, each of the plurality of release tabs configured for interacting with the plunger engagement sleeve to effect a release of the plunger from the piston upon rotation of the plunger about the central longitudinal axis.

12. The plunger according to claim 11, wherein a proximal end of each of the plurality of release tabs has a pointed guide surface.

13. The plunger according to claim 1, wherein when the plunger is in the locked state with the piston, the at least one catch protrudes radially outward from the outer surface of the at least one retaining member in a direction away from the central longitudinal axis, and wherein the at least one catch is configured to be received within the locking feature that is shaped as a locking groove protruding radially outward form an inner surface of the plunger engagement sleeve.

* * * * *

UNITED STATES PATENT AND TRADEMARK OFFICE
CERTIFICATE OF CORRECTION

PATENT NO. : 11,998,718 B2  
APPLICATION NO. : 17/999592  
DATED : June 4, 2024  
INVENTOR(S) : Cowan et al.

Page 1 of 1

It is certified that error appears in the above-identified patent and that said Letters Patent is hereby corrected as shown below:

In the Specification

In Column 5, Lines 19-20, delete "having a barrel having a barrel" and insert -- having a barrel --, therefor.
In Column 7, Line 1, delete "actuator" and insert -- actuator is --, therefor.
In Column 7, Lines 64-65, delete "having: a barrel having a barrel" and insert -- having a barrel --, therefor.
In Column 8, Line 5, delete "is" and insert -- axis --, therefor.
In Column 27, Line 62, delete "away" and insert -- away from --, therefor.
In Column 35, Lines 41-42, delete "disengaged" and insert -- disengagement --, therefor.
In Column 41, Line 14, delete "shown in described" and insert -- shown and described --, therefor.
In Column 43, Line 47, delete "300)." and insert -- 300. --, therefor.
In Column 52, Line 53, delete "shown in described" and insert -- shown and described --, therefor.

In the Claims

In Column 67, Line 18, in Claim 9, delete "has" and insert -- has a --, therefor.
In Column 68, Line 19, in Claim 13, delete "form" and insert -- from --, therefor.

Signed and Sealed this  
First Day of July, 2025

Coke Morgan Stewart  
*Acting Director of the United States Patent and Trademark Office*